US 8,257,356 B2

(12) United States Patent
Bleich et al.

(10) Patent No.: US 8,257,356 B2
(45) Date of Patent: Sep. 4, 2012

(54) GUIDEWIRE EXCHANGE SYSTEMS TO TREAT SPINAL STENOSIS

(75) Inventors: Jeffrey L. Bleich, Palo Alto, CA (US); Gregory P. Schmitz, Los Gatos, CA (US); Roy Leguidleguid, Union City, CA (US); Jefferey Bleam, Boulder Creek, CA (US)

(73) Assignee: Baxano, Inc., San Jose, CA (US)

( * ) Notice: Subject to any disclaimer, the term of this patent is extended or adjusted under 35 U.S.C. 154(b) by 1029 days.

(21) Appl. No.: 12/127,535

(22) Filed: May 27, 2008

(65) Prior Publication Data

US 2008/0275458 A1 Nov. 6, 2008

Related U.S. Application Data

(63) Continuation-in-part of application No. 11/251,199, filed on Oct. 15, 2005, and a continuation-in-part of application No. 11/468,247, filed on Aug. 29, 2006, now Pat. No. 7,857,813.

(60) Provisional application No. 60/685,190, filed on May 27, 2005, provisional application No. 60/681,719, filed on May 16, 2005, provisional application No. 60/681,864, filed on May 16, 2005, provisional application No. 60/622,865, filed on Oct. 28, 2004, provisional application No. 60/619,306, filed on Oct. 15, 2004.

(51) Int. Cl.
*A61B 17/00* (2006.01)

(52) U.S. Cl. ........................................................ 606/79

(58) Field of Classification Search .................... 606/79, 606/85, 103, 110, 119, 131, 163, 171–176, 606/167

See application file for complete search history.

(56) References Cited

U.S. PATENT DOCUMENTS

| 184,804 A | 11/1876 | Stohlmann |
| 289,104 A | 11/1883 | How |
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |

(Continued)

FOREIGN PATENT DOCUMENTS

DE 3209403 A1 9/1983

(Continued)

OTHER PUBLICATIONS

Garabedian et al.; U.S. Appl. No. 12/824,043; entitled "Surgical Tools for Treatment of Spinal Stenosis"; filed Jun. 25, 2010.

(Continued)

*Primary Examiner* — Kevin T Truong
*Assistant Examiner* — Sameh Boles
(74) *Attorney, Agent, or Firm* — Shay Glenn LLP

(57) ABSTRACT

Guidewire exchange systems, devices and methods, for positioning and actuating surgical devices in a desired position between two tissues in a patient's body are described. A guidewire may be coupled to a surgical device for positioning and actuating (e.g., urging against a target tissue). The guidewire may be exchanged between different surgical devices during the same procedure, and the guidewire and surgical devices may be releaseably or permanently coupled. The surgical device generally includes one or more guidewire coupling members. A system may include a guidewire and a surgical device having a guidewire coupling member. Methods, devices and systems may be used in open, less-invasive or percutaneous surgical procedures.

12 Claims, 43 Drawing Sheets

U.S. PATENT DOCUMENTS

| | | | |
|---|---|---|---|
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |

| Patent | Date | Inventor |
|---|---|---|
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,928,159 A | 7/1999 | Eggers et al. |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter et al. |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,859 B1 | 7/2002 | Foley et al. |
| 6,425,887 B1 | 7/2002 | McGuckin et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | Skladnev et al. |
| 6,488,636 B2 | 12/2002 | Bryan et al. |
| 6,491,646 B1 | 12/2002 | Blackledge |
| 6,500,128 B2 | 12/2002 | Marino |
| 6,500,189 B1 | 12/2002 | Lang et al. |
| 6,512,958 B1 | 1/2003 | Swoyer et al. |
| 6,516,223 B2 | 2/2003 | Hofmann |
| 6,520,907 B1 | 2/2003 | Foley et al. |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,562,033 B2 | 5/2003 | Shah et al. |
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |
| 6,575,979 B1 | 6/2003 | Cragg |
| 6,579,291 B1 | 6/2003 | Keith et al. |
| 6,584,345 B2 | 6/2003 | Govari |
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Cory et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |

| | | |
|---|---|---|
| 6,682,536 B2 | 1/2004 | Vardi et al. |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,815 B2 | 5/2004 | Ginn |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,772,012 B2 | 8/2004 | Ricart et al. |
| 6,776,765 B2 | 8/2004 | Soukup et al. |
| 6,788,966 B2 | 9/2004 | Kenan et al. |
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,189,240 B1 * | 3/2007 | Dekel ............................ 606/85 |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0023190 A1 | 1/2003 | Cox |
| 2003/0045808 A1 | 3/2003 | Kaula et al. |
| 2003/0045937 A1 * | 3/2003 | Ginn ........................ 623/17.11 |
| 2003/0074037 A1 | 4/2003 | Moore et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0098074 A1 | 5/2004 | Erickson et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |

| | | | | | |
|---|---|---|---|---|---|
| 2004/0181150 A1 | 9/2004 | Evans et al. | 2006/0264994 A1 | 11/2006 | Schomer et al. |
| 2004/0199084 A1 | 10/2004 | Kelleher et al. | 2006/0276720 A1 | 12/2006 | McGinnis et al. |
| 2004/0199159 A1 | 10/2004 | Lee et al. | 2006/0276802 A1 | 12/2006 | Vresilovic et al. |
| 2004/0199166 A1 | 10/2004 | Schmieding et al. | 2006/0276836 A1 | 12/2006 | Bergin et al. |
| 2004/0225233 A1* | 11/2004 | Frankowski et al. ......... 600/585 | 2007/0010717 A1 | 1/2007 | Cragg |
| 2004/0260358 A1 | 12/2004 | Vaughan et al. | 2007/0016097 A1 | 1/2007 | Farquhar et al. |
| 2005/0027199 A1 | 2/2005 | Clarke | 2007/0016185 A1 | 1/2007 | Tullis et al. |
| 2005/0033393 A1 | 2/2005 | Daglow | 2007/0027464 A1 | 2/2007 | Way et al. |
| 2005/0049592 A1 | 3/2005 | Keith et al. | 2007/0027514 A1 | 2/2007 | Gerber |
| 2005/0060006 A1 | 3/2005 | Pflueger et al. | 2007/0049962 A1 | 3/2007 | Marino et al. |
| 2005/0075578 A1 | 4/2005 | Gharib et al. | 2007/0055215 A1 | 3/2007 | Tran et al. |
| 2005/0149034 A1 | 7/2005 | Assell et al. | 2007/0055262 A1 | 3/2007 | Tomita et al. |
| 2005/0149035 A1 | 7/2005 | Pimenta et al. | 2007/0055263 A1 | 3/2007 | Way et al. |
| 2005/0149154 A1 | 7/2005 | Cohen et al. | 2007/0073356 A1 | 3/2007 | Rooney et al. |
| 2005/0171587 A1 | 8/2005 | Daglow et al. | 2007/0106219 A1 | 5/2007 | Grabinsky |
| 2005/0182454 A1 | 8/2005 | Gharib et al. | 2007/0123766 A1 | 5/2007 | Whalen, III et al. |
| 2005/0187537 A1 | 8/2005 | Loeb et al. | 2007/0123888 A1 | 5/2007 | Bleich et al. |
| 2005/0197661 A1 | 9/2005 | Carrison et al. | 2007/0123890 A1 | 5/2007 | Way et al. |
| 2005/0203599 A1 | 9/2005 | Garabedian et al. | 2007/0162044 A1 | 7/2007 | Marino |
| 2005/0209610 A1 | 9/2005 | Carrison | 2007/0162061 A1 | 7/2007 | Way et al. |
| 2005/0209617 A1 | 9/2005 | Koven et al. | 2007/0162062 A1 | 7/2007 | Norton et al. |
| 2005/0209622 A1 | 9/2005 | Carrison | 2007/0166345 A1 | 7/2007 | Pavcnik et al. |
| 2005/0216023 A1 | 9/2005 | Aram et al. | 2007/0198019 A1 | 8/2007 | Schomer et al. |
| 2005/0222598 A1 | 10/2005 | Ho et al. | 2007/0213583 A1 | 9/2007 | Kim et al. |
| 2005/0234425 A1 | 10/2005 | Miller et al. | 2007/0213584 A1 | 9/2007 | Kim et al. |
| 2005/0256423 A1 | 11/2005 | Kirsner | 2007/0213733 A1 | 9/2007 | Bleich et al. |
| 2005/0261692 A1 | 11/2005 | Carrison et al. | 2007/0213734 A1 | 9/2007 | Bleich et al. |
| 2005/0277942 A1 | 12/2005 | Kullas et al. | 2007/0213735 A1 | 9/2007 | Saadat et al. |
| 2005/0283148 A1 | 12/2005 | Janssen et al. | 2007/0225703 A1 | 9/2007 | Schmitz et al. |
| 2005/0283204 A1 | 12/2005 | Buhlmann et al. | 2007/0255162 A1 | 11/2007 | Abboud et al. |
| 2006/0004369 A1 | 1/2006 | Patel et al. | 2007/0255369 A1 | 11/2007 | Bonde et al. |
| 2006/0015035 A1 | 1/2006 | Rock | 2007/0260252 A1 | 11/2007 | Schmitz et al. |
| 2006/0025702 A1 | 2/2006 | Sterratino et al. | 2007/0270795 A1 | 11/2007 | Francischelli et al. |
| 2006/0025703 A1 | 2/2006 | Miles et al. | 2007/0270865 A1 | 11/2007 | Arnin et al. |
| 2006/0025797 A1 | 2/2006 | Lock et al. | 2007/0276286 A1 | 11/2007 | Miller |
| 2006/0030854 A1 | 2/2006 | Haines | 2007/0276390 A1 | 11/2007 | Solsberg et al. |
| 2006/0036211 A1 | 2/2006 | Solsberg et al. | 2007/0282217 A1 | 12/2007 | McGinnis et al. |
| 2006/0036271 A1 | 2/2006 | Schomer et al. | 2007/0299403 A1 | 12/2007 | Crowe et al. |
| 2006/0036272 A1 | 2/2006 | Solsberg et al. | 2007/0299459 A1 | 12/2007 | Way et al. |
| 2006/0058732 A1 | 3/2006 | Harp | 2008/0033465 A1 | 2/2008 | Schmitz et al. |
| 2006/0064101 A1 | 3/2006 | Arramon | 2008/0051812 A1 | 2/2008 | Schmitz et al. |
| 2006/0079919 A1 | 4/2006 | Harp | 2008/0058874 A1 | 3/2008 | Westlund et al. |
| 2006/0085048 A1 | 4/2006 | Cory et al. | 2008/0086034 A1 | 4/2008 | Schmitz et al. |
| 2006/0085049 A1 | 4/2006 | Cory et al. | 2008/0086114 A1 | 4/2008 | Schmitz et al. |
| 2006/0089609 A1 | 4/2006 | Bleich et al. | 2008/0091227 A1 | 4/2008 | Schmitz et al. |
| 2006/0089633 A1 | 4/2006 | Bleich et al. | 2008/0097465 A1 | 4/2008 | Rollins et al. |
| 2006/0089640 A1 | 4/2006 | Bleich et al. | 2008/0103504 A1 | 5/2008 | Schmitz et al. |
| 2006/0089650 A1 | 4/2006 | Nolde | 2008/0119711 A1 | 5/2008 | Nikumb et al. |
| 2006/0089688 A1 | 4/2006 | Panescu | 2008/0125621 A1 | 5/2008 | Gellman et al. |
| 2006/0094976 A1 | 5/2006 | Bleich | 2008/0125709 A1 | 5/2008 | Chang et al. |
| 2006/0095026 A1 | 5/2006 | Ricart et al. | 2008/0140153 A1 | 6/2008 | Burdulis |
| 2006/0095028 A1 | 5/2006 | Bleich | 2008/0140169 A1 | 6/2008 | Imran |
| 2006/0095059 A1 | 5/2006 | Bleich et al. | 2008/0146867 A1 | 6/2008 | Gellman et al. |
| 2006/0100651 A1 | 5/2006 | Bleich | 2008/0147084 A1 | 6/2008 | Bleich et al. |
| 2006/0122458 A1 | 6/2006 | Bleich | 2008/0161809 A1 | 7/2008 | Schmitz et al. |
| 2006/0122620 A1 | 6/2006 | Kim | 2008/0161810 A1 | 7/2008 | Melkent |
| 2006/0122653 A1 | 6/2006 | Bradley et al. | 2008/0197024 A1 | 8/2008 | Simpson et al. |
| 2006/0122654 A1 | 6/2006 | Bradley et al. | 2008/0200912 A1 | 8/2008 | Long et al. |
| 2006/0135882 A1 | 6/2006 | Bleich | 2008/0221383 A1 | 9/2008 | Way et al. |
| 2006/0142753 A1 | 6/2006 | Francischelli et al. | 2008/0221586 A1 | 9/2008 | Garcia-Bengochea et al. |
| 2006/0149278 A1 | 7/2006 | Abdou | 2008/0288005 A1 | 11/2008 | Jackson |
| 2006/0161189 A1 | 7/2006 | Harp | 2008/0319459 A1 | 12/2008 | Al-najjar |
| 2006/0173374 A1 | 8/2006 | Neubardt et al. | 2009/0018610 A1 | 1/2009 | Gharib et al. |
| 2006/0184175 A1 | 8/2006 | Schomer et al. | 2009/0054804 A1 | 2/2009 | Gharib et al. |
| 2006/0195107 A1 | 8/2006 | Jones et al. | 2009/0054936 A1 | 2/2009 | Eggen et al. |
| 2006/0200153 A1 | 9/2006 | Harp | 2009/0054941 A1 | 2/2009 | Eggen et al. |
| 2006/0200154 A1 | 9/2006 | Harp | 2009/0062871 A1 | 3/2009 | Chin et al. |
| 2006/0200155 A1 | 9/2006 | Harp | 2009/0062872 A1 | 3/2009 | Chin et al. |
| 2006/0206115 A1 | 9/2006 | Schomer et al. | 2009/0105604 A1 | 4/2009 | Bertagnoli et al. |
| 2006/0206117 A1 | 9/2006 | Harp | 2009/0118709 A1 | 5/2009 | Sand et al. |
| 2006/0206118 A1 | 9/2006 | Kim et al. | 2009/0124934 A1 | 5/2009 | Rabbitte et al. |
| 2006/0206178 A1 | 9/2006 | Kim | 2009/0138056 A1 | 5/2009 | Anderson et al. |
| 2006/0224060 A1 | 10/2006 | Garell et al. | 2009/0143807 A1 | 6/2009 | Sand |
| 2006/0224078 A1 | 10/2006 | Hoey et al. | 2009/0143829 A1 | 6/2009 | Shluzas |
| 2006/0235451 A1 | 10/2006 | Schomer et al. | 2009/0177112 A1 | 7/2009 | Gharib et al. |
| 2006/0235452 A1 | 10/2006 | Schomer et al. | 2009/0177144 A1 | 7/2009 | Masmanidis et al. |
| 2006/0241648 A1* | 10/2006 | Bleich et al. ............... 606/103 | 2009/0182382 A1 | 7/2009 | Justis et al. |
| 2006/0258951 A1 | 11/2006 | Bleich et al. | 2009/0209879 A1 | 8/2009 | Kaula et al. |
| 2006/0264952 A1 | 11/2006 | Nelson et al. | 2009/0216284 A1 | 8/2009 | Chin et al. |

| | | | |
|---|---|---|---|
| 2010/0057087 A1 | 3/2010 | Cha | |
| 2010/0094231 A1 | 4/2010 | Bleich et al. | |
| 2010/0274250 A1 | 10/2010 | Wallace et al. | |
| 2010/0331883 A1 | 12/2010 | Schmitz et al. | |
| 2010/0331900 A1 | 12/2010 | Garabedian et al. | |
| 2011/0004207 A1 | 1/2011 | Wallace et al. | |
| 2011/0046613 A1 | 2/2011 | Schmitz et al. | |
| 2011/0060314 A1 | 3/2011 | Wallace et al. | |
| 2011/0112539 A1 | 5/2011 | Wallace et al. | |
| 2011/0160731 A1 | 6/2011 | Bleich et al. | |
| 2011/0190772 A1 | 8/2011 | Saadat | |
| 2011/0196257 A1 | 8/2011 | Schmitz et al. | |
| 2011/0224709 A1 | 9/2011 | Bleich | |
| 2011/0224710 A1 | 9/2011 | Bleich | |
| 2012/0016368 A1 | 1/2012 | Bleich et al. | |

FOREIGN PATENT DOCUMENTS

| | | | |
|---|---|---|---|
| DE | 4036804 A1 | 5/1992 | |
| EP | 359883 A1 | 3/1990 | |
| EP | 1304080 A2 | 4/2003 | |
| EP | 1340467 A2 | 9/2003 | |
| EP | 1207794 B1 | 5/2004 | |
| EP | 1315463 B1 | 5/2005 | |
| EP | 1611851 A1 | 1/2006 | |
| EP | 1006885 B1 | 9/2006 | |
| FR | 2706309 | 12/1994 | |
| JP | 2960140 B2 | 10/1999 | |
| JP | 24065380 A2 | 3/2004 | |
| RU | 2107459 | 3/1998 | |
| WO | WO-96/22057 | 7/1996 | |
| WO | WO9734536 A2 | 9/1997 | |
| WO | WO9918866 A1 | 4/1999 | |
| WO | WO99/21500 A1 | 5/1999 | |
| WO | WO00/67651 A1 | 11/2000 | |
| WO | WO 01/08571 | 2/2001 | |
| WO | WO0108571 A1 | 2/2001 | |
| WO | WO01/62168 A2 | 8/2001 | |
| WO | WO0207901 A1 | 1/2002 | |
| WO | WO0234120 A2 | 5/2002 | |
| WO | WO02076311 A2 | 10/2002 | |
| WO | WO03/026482 A2 | 4/2003 | |
| WO | WO03/066147 A1 | 8/2003 | |
| WO | WO2004002331 A1 | 1/2004 | |
| WO | WO2004028351 A2 | 4/2004 | |
| WO | WO2004/043272 A1 | 5/2004 | |
| WO | WO2004056267 A1 | 7/2004 | |
| WO | WO2004/078066 A2 | 9/2004 | |
| WO | WO2004080316 A1 | 9/2004 | |
| WO | WO2004096080 A2 | 11/2004 | |
| WO | WO2005/009300 A1 | 2/2005 | |
| WO | WO2005057467 A2 | 6/2005 | |
| WO | WO2005077282 A1 | 8/2005 | |
| WO | WO2005089433 A2 | 9/2005 | |
| WO | WO2006009705 A2 | 1/2006 | |
| WO | WO2006015302 A1 | 2/2006 | |
| WO | WO2006017507 A2 | 2/2006 | |
| WO | WO2006039279 A2 | 4/2006 | |
| WO | WO2006042206 A2 | 4/2006 | |
| WO | WO2006044727 A2 | 4/2006 | |
| WO | WO2006047598 A1 | 5/2006 | |
| WO | WO2006058079 A3 | 6/2006 | |
| WO | WO2006058195 A2 | 6/2006 | |
| WO | WO2006062555 A2 | 6/2006 | |
| WO | WO2006086241 A2 | 8/2006 | |
| WO | WO2006099285 A2 | 9/2006 | |
| WO | WO2006102085 A2 | 9/2006 | |
| WO | WO2007008709 A2 | 1/2007 | |
| WO | WO2007021588 A1 | 2/2007 | |
| WO | WO2007022194 A2 | 2/2007 | |
| WO | WO2007059343 A2 | 2/2007 | |
| WO | WO2007067632 A2 | 6/2007 | |
| WO | WO2008008898 A2 | 1/2008 | |
| WO | WO2009/012265 A2 | 1/2009 | |
| WO | WO2009/018220 A1 | 2/2009 | |
| WO | WO2009/021116 A2 | 2/2009 | |
| WO | WO2009/036156 A1 | 3/2009 | |
| WO | WO2009/046046 A1 | 4/2009 | |
| WO | WO2009/058566 A1 | 5/2009 | |
| WO | WO2009/151926 A2 | 12/2009 | |

OTHER PUBLICATIONS

Schmitz et al.; U.S. Appl. No. 12/816,729 entitled Access and Tissue Modification Systems and Methods, filed Jun. 16, 2010.
Wallace et al.; U.S. Appl. No. 12/724,315 entitled "Flexible Neural Localization Devices and Methods," filed Mar. 15, 2010.
Wallace et al.; U.S. Appl. No. 12/773,595 entitled "Tissue Modification Devices and Methods," filed May 4, 2010.
Schmitz et al.; U.S. Appl. No. 12/324,147 entitled "Tissue modification devices," filed Nov. 26, 2008.
Schmitz et al.; U.S. Appl. No. 12/352,385 entitled "Devices, methods and systems for neural localization," filed Jan. 12, 2009.
Bleich et al.; U.S. Appl. No. 12/352,978 entitled "Multiple pathways for spinal nerve rood decompression from a single access point," filed Jan. 13, 2009.
Bleich, Jeffrey; U.S. Appl. No. 12/357,289 entitled "Devices and methods for selective surgical removal of tissue, "filed Jan. 21, 2009.
Arcenio et al.; U.S. Appl. No. 12/980,165 entitled "Systems and Methods for Performing Spinal Fusion", filed Dec. 28, 2010.
Bleich et al.; U.S. Appl. No. 12/984,162 entitled "Devices and Methods for Tissue Access", filed Jan. 4, 2011.
Schmitz et al.; U.S. Appl. No. 12/917,253; entitled "Tissue Access Guidewire System and Method"; filed Nov. 1, 2010.
Wallace et al.; U.S. Appl. No. 12/911,537 entitled "Devices and Methods for Treating Tissue", filed Oct. 25, 2010.
Wallace et al.; U.S. Appl. No. 13/007,381 entitled "Tissue Modification Devices", filed Jan. 14, 2011.
Bleich et al.; U.S. Appl. No. 12/428,369 entitled "Devices and methods for tissue modification," filed Apr. 22, 2009.
Bleich et al.; U.S. Appl. No. 12/504,545 entitled "Spinal access and neural localization," filed Jul. 16, 2009.
Schmitz et al.; U.S. Appl. No. 12/496,094 entitled "Access and tissue modification systems and methods," filed Jul. 1, 2009.
Saadat et al.; U.S. Appl. No. 13/078,376 entitled "Powered Tissue Modification Devices and Methods", filed Apr. 1, 2011.
Schmitz et al.; U.S. Appl. No. 13/090,944 entitled "Method, System and Apparatus for Neural Localization", filed Apr. 20, 2011.
US Surgical Kerrison Spinal Rongeur K943116 [online] Retrieved from the internet: <URL: http://www.ussurg.com/uss/index.html>. Jul. 27, 1994.
Zeppelin Laminectomy Rongeur K901372, [online] Retrieved from the internet: <URL: http://www.zeppelin-medical.com/download/instruments.pdf>. Oct. 24, 2006.
Ellman Int. Disc-FX System Accessories K052241 [online] Retrieved from the Internet: <URL: http://www.ellman.com/ medical/ >. Feb. 27, 2006.
Ohta et al., "Superimposed Mechanomygraphic Response at Different Contraction Intensity in Medial Gastrocnemius and Soleus Muscles," International Journal of Sport and Health Science: vol. 5, 63-70, 2007.
Schwieger et al., "Abrasive Water Jet Cutting as a New Procedure for Cutting Cancellous Bone—In Vitro Testing in Comparison with the Oscillating Saw," Wiley Interscience, www.interscience,wiley.com, Sep. 20, 2004, 223-228.
Mopec Bone-Cutting tool, Product brochure, Total pp. 4. First accessed Dec. 15, 2005.
Codman Laminectomy Shaver (a Johnson & Johnson company www.codman.com) catalogue, pp. 416-431, [online] Retrieved from the internet: <URL: http:llwww.codman.com/PDFs/Catalog_04_R.pdf>. First accessedOct. 24, 2006.
Integra Ruggles TM Kerrison Rongeurs [online] Retrieved from the internet: <URL: http://www.integra-ls.com/products!? product=22>. First accessedOct. 24, 2006.
Bleich et al.; U.S. Appl. No. 13/112,886 entitled "Methods, Systems and Devices for Carpal Tunnel Release", filed May 20, 2011.
Bleich et al.; U.S. Appl. No. 13/112,918 entitled "Methods, Systems and Devices for Carpal Tunnel Release", filed May 20, 2011.
Bleich et al.; U.S. Appl. No. 13/312,272 entitled "Multiple Pathways for Spinal Nerve Root Decompression From a Single Access Point," filed Dec. 6, 2011.
Schmitz et al.; U.S. Appl. No. 13/232,882 entitled "Tissue Modification Devices," filed Sep. 14, 2011.

Schmitz et al.; U.S. Appl. No. 13/267,683 entitled "Flexible Tissue Removal Devices and Methods," filed Oct. 6, 2011.
Sun et al.; U.S. Appl. No. 13/340,363 entitled "Flexible Neural Localization Devices and Methods," filed Dec. 29, 2011.
Wallace et al.; U.S. Appl. No. 13/338,103 entitled "Tissue Modification Devices and Methods," filed Dec. 27, 2011.
Wallace et al.; U.S. Appl. No. 13/338,134 entitled "Surgical Tools for Treatment of Spinal Stenosis." filed Dec. 27, 2011.
Barer Malvin, "Instrument to Enhance Passage of the Gigli Saw," Journal of Pediatric Orthopedics, Raven Press, New York, 1984, 4:762-763.
Baumgart et al., "Indikation and Technik der Knochendurchtrennung," Der Chirurg, 1998, vol. 69:1188-1196. (in German with Eng Summary).
Bohinski et al., "Novel use of a threadwire saw for high sacral amputation," Journal of neurosurgery: Spine, 2005, vol. 3, 71R78.
Brunori et al., "Celebrating the centennial (1894-1994): Leonardo Gigli and his wire saw," J. Neurosurg, 1995, 82:1086-1090.
Burrows, Harold, "Surgical instruments and appliances used in operations," Faber and Faber, London, 1937, total pp. 4.
Dammann, Gordon, Pictorial Encyclopedia of Civil War Medical Instruments and Equipment, Pictorial Histories Publishing Company, Missoula, Montana, 1983, Total pp. 2.
Edwards et al; "T-Saw Laminoplasty for the Management of Cervical Spondylotic Myelopathy," Spine, Lippincott Williams & Wilkins, Inc., 2000, vol. 25 (14): 1788R1794.
Eralp et al., "A comparison of two osteotomy techniques for tibial lengthening," Archives of orthopaedic and trauma surgery, 2004, vol. 124:298R300.
Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar_stenosis/lumbarStenosis.swf.
Fujita et al., "Chordoma in the Cervical Spine Managed with En Bloc Excision," Spine, Lippincott Williams & Wilkins, Inc., 1999, 24 (17), 1848-1851.
Goel, Atul, "Neurosurgical forum, Supraorbital Craniotomy," Journal of Neurosurgery, 1994, vol. 81, 642-643.
Gore Smoother User Manual, W. L. Gore & Associates, Inc. Flagstaff, AZ, Dec. 1999,Total pp. 3.
Hara et al., "En Bloc Laminoplasty Performed with Threadwire Saw: Technical Note," Neurosurgery, Jan. 2001, vol. 48, No. 1, pp. 235-239.
Hata et al; "A less invasive surgery for rotator cuff tear: Mini-open repair," Journal of Shoulder and Elbow Surgery, 2001, vol. 10 No. 1, 11-16.
Honl et al; "The Use of Water-Jetting Technology in Prostheses Revision Surgery R First Results of Parameter Studies on Bone and Bone Cement," J. Biomed Mater Res (Applied Biomaterials), John Wiley & Sons, Inc, 2000, 53, 6: 781-790.
Jun, Byung-Yoon, "Posterior Lumbar Interbody Fusion With Restoration of Lamina and Facet Fusion," Spine, Lippincott Williams & Wilkins, Inc., 2000, vol. 25 No. 8, 917R922.
Kawahara et al., "Recapping T-Saw Laminoplasty for Spinal Cord Tumors," Spine, 1999, vol. 24 No. 13, pp. 1363-1370.
Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680R684.
Miyamoto et al., "Kyphectomy Using a Surgical Threadwire (T-saw) for Kyphotic Deformity in a Child With Myelomeningocele," Spine, Lippincott Williams & Wilkins, Inc., 2003, vol. 28 No. 10, E187RE190.
Abdel-Wanis et al., "Tumor growth potential after tumoral and instrumental contamination: an in-vivo comparative study of T-saw, Gigli saw, and scalpel," Journal of orthopaedic science, 2001, vol. 6, 424R429.
Nakagiri et al., "Thoracoscopic Rib Resection Using a Gigli Saw," The Annals of Thoracic Surgery, 2005, vol. 80, 755R756.
Osaka et al., "Clinical significance of a wide excision policy for sacrococcygeal chordoma," J Cancer Res Clin Oncol, 2005, Total pp. 6.
Paley et al., "Percutaneous Osteotomies," Orthopedic Clinics of North America, 1991, vol. 22 No. 4, 613-624.
Pancoast, Joseph, "A Treatise on Operative Surgery," Carey and Hart, Philadelphia, 1844, Total pp. 11.
Park et al; "Cases of the Excision of Carious Joints," John Scrymgeour, Glasgow, 1806, Total pp. 6.
Peavy et al., "Comparison of Cortical Bone Ablations by Using Infrared Laser Wavelengths 2.9 to 9.2 μm, Lasers in Surgery and Medicine," 1999, vol. 26, 421R434.
Peltier, Leonard Orthopedics: A History and Iconography, Norman Publishing, San Francisco, 1993, Total pp. 3.
Reckling Frederick, "Modified Stethoscope Earpiece Makes Excellent Gigli Saw Guide," J Bone and Joint Surgery Am, Dec. 1972, 54-A(8), 1787-1788.
Rutkow, Ira, "Surgery An Illustrated History," Mosby'Year Book, Inc., St. Louis, 1993, Total pp. 4.
Schwieger et al., "Abrasive Water Jet Cutting as a New Procedure for Cutting Cancellous Bone'In Vitro Testing in Comparison with the Oscillating Saw," Wiley Interscience, www.interscience,wiley.com, Sep. 20, 2004, 223-228.
Sen, Cengiz, Tibia proksimalinde Gigli testeresi ile yapilanperkütan osteotominin güvenilirligi: Kadavra calismasi, Acta orthopaedica et traumatologica turcica, 2002, vol. 36, 136-140; (in Russian w/ Eng Summary).
Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672.
Shiraishi T., "A new technique for exposure of the cervical spine laminae," Journal of neurosurgery. Spine, 2002, vol. 96(1), 122-126.
Shiraishi T., Skip laminectomy—a new treatment for cervical spondylotic myelopathy, preserving bilateral muscular attachments to the spinous processes: a preliminary report, Spine, 2002, vol. 2(2), 108-115.
Skippen et al., "The Chain Saw R A Scottish Invention," Scottish Medical Journal, 2004, vol. 49(2), 72-75.
Stevens et al., "Calvarial Bone Graft Harvest Using the Gigli Saw," Journal of Oral and Maxillofacial Surgery, 1998, vol. 56, 798-799.
Takada et al., "Unusual Metastasis to the Cauda Equina From Renal Cell Carcinoma," Spine, Lippincott Williams & Wilkins, Inc., 2003, vol. 28 No. 6, E114RE117.
Paktiss et al., "Afghan Percutaneous Osteotomy," Journal of Pediatric Orthopaedics, Raven Press Ltd, New York, 1993, vol. 13 No. 4, 531-533.
Tomita et al., "Expansive Midline T-Saw Laminoplasty (Modified Spinour Process-Splitting) for the Management of Cervical Myelopathy," Spine, Lippincott Williams & Wilkins, Inc, 1998, 23(1), 32-37.
Tomita et al., "The Threadwire Saw: a New Device for Cutting Bone," The Journal of Bone and Joint Surgery, 1996, vol. 78, 1915-1917.
Tomita et al., "The Use of the T-Saw for Expansive Midline laminoplasty in the Treatment of Cervical Myelopathy," Orthopedics and Traumatology, No. 3, pp. 169-178, 2002.
Tomita et al., "Total en bloc spondylectomy and circumspinal decompression for solitary spinal metastasis," Paraplegia, 1994, 32:36-46.
Tomita K. et al., "Total en bloc spondylectomy for solitary spinal metastases," International Orthopaedics (SICOT), 1994, 18: 291-298.
Truax, Charles, "The Mechanics of Surgery," Chicago, IL; 1899, Total pp. 3.
Wilkins, Robert H, "Neurosurgical Classics," Johnson Reprint Corporation, New York, 1965, 377-382.
Schmitz et al; U.S. Appl. No. 12/060,229 entitled "Method, system, and apparatus for neural localization," filed Mar. 31, 2008.
Bleich, et al.; U.S. Appl. No. 12/140,201 entitled "Devices and methods for measuring the space around a nerve root," filed Jun. 16, 2008.
Schmitz et al.; U.S. Appl. No. 12/170,392 entitled "Spinal access system and method," filed Jul. 9, 2008.

\* cited by examiner

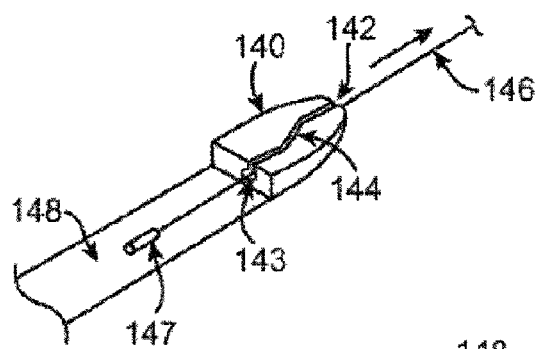
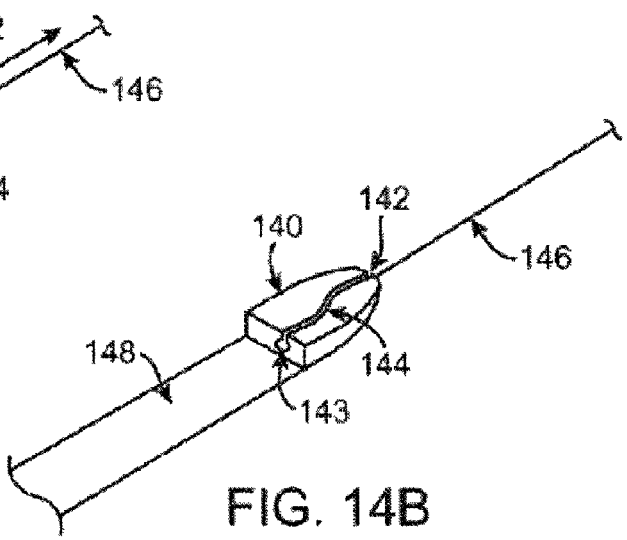
FIG. 14A
FIG. 14B
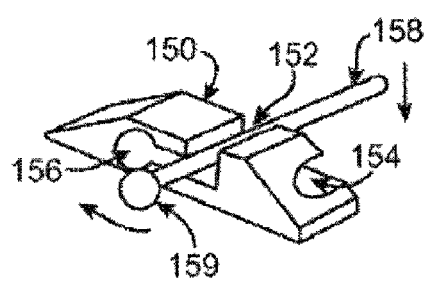
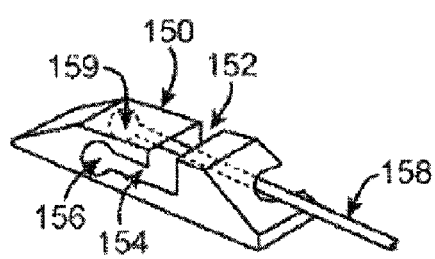
FIG. 15A
FIG. 15C
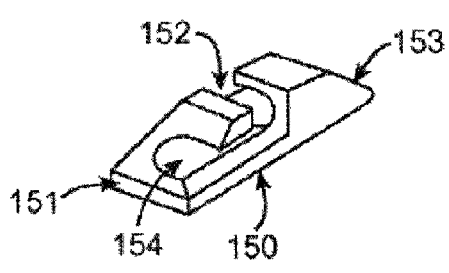
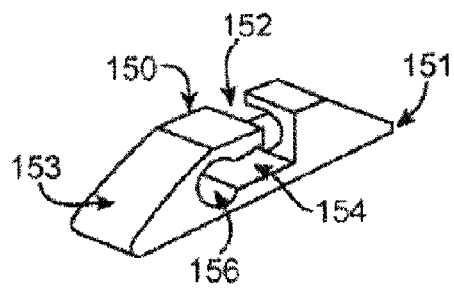
FIG. 15E
FIG. 15F
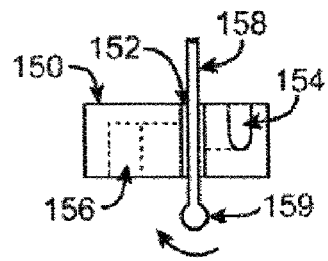
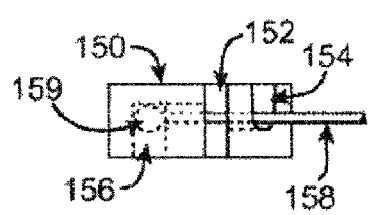
FIG. 15B
FIG. 15D

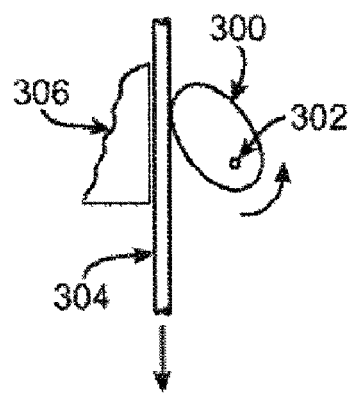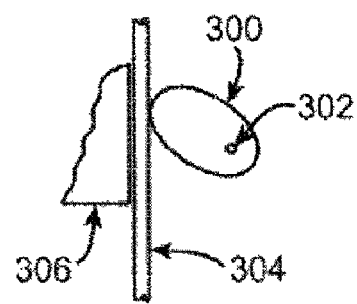
FIG. 18A    FIG. 18B
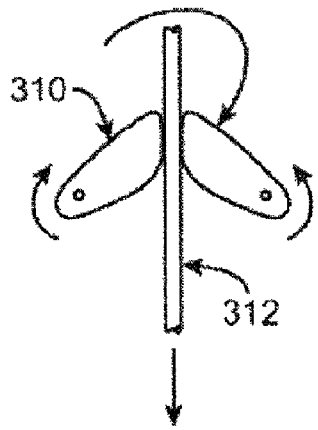
FIG. 19
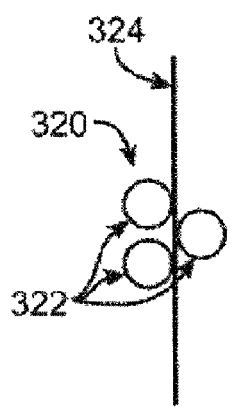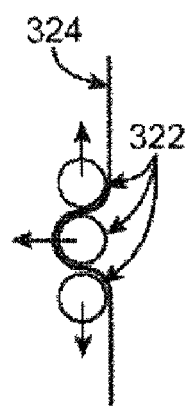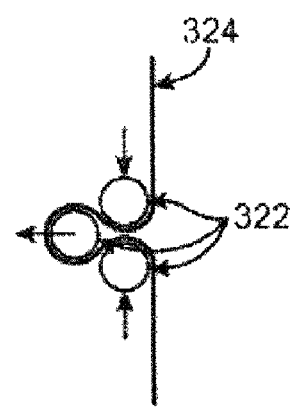
FIG. 20A    FIG. 20B    FIG. 20C

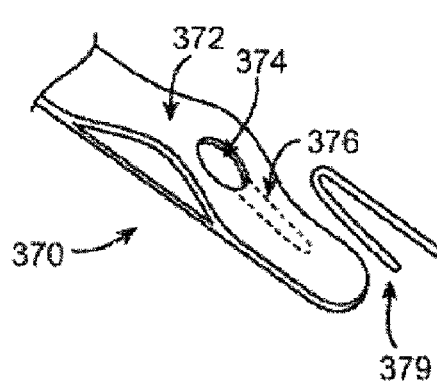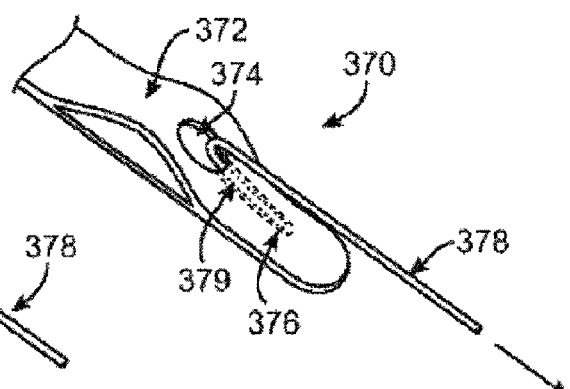
FIG. 25A  FIG. 25B
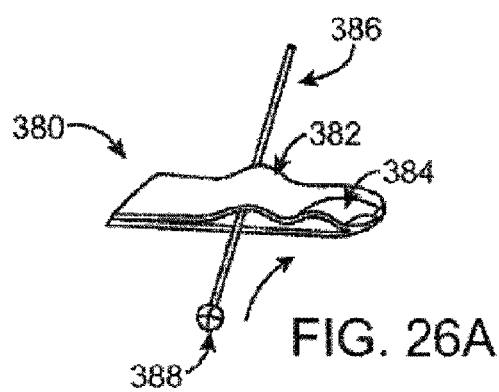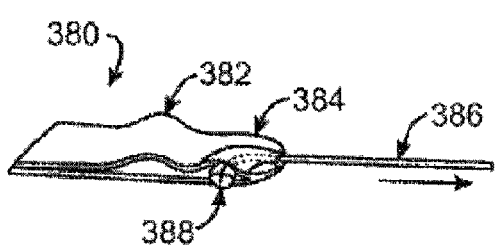
FIG. 26A  FIG. 26B
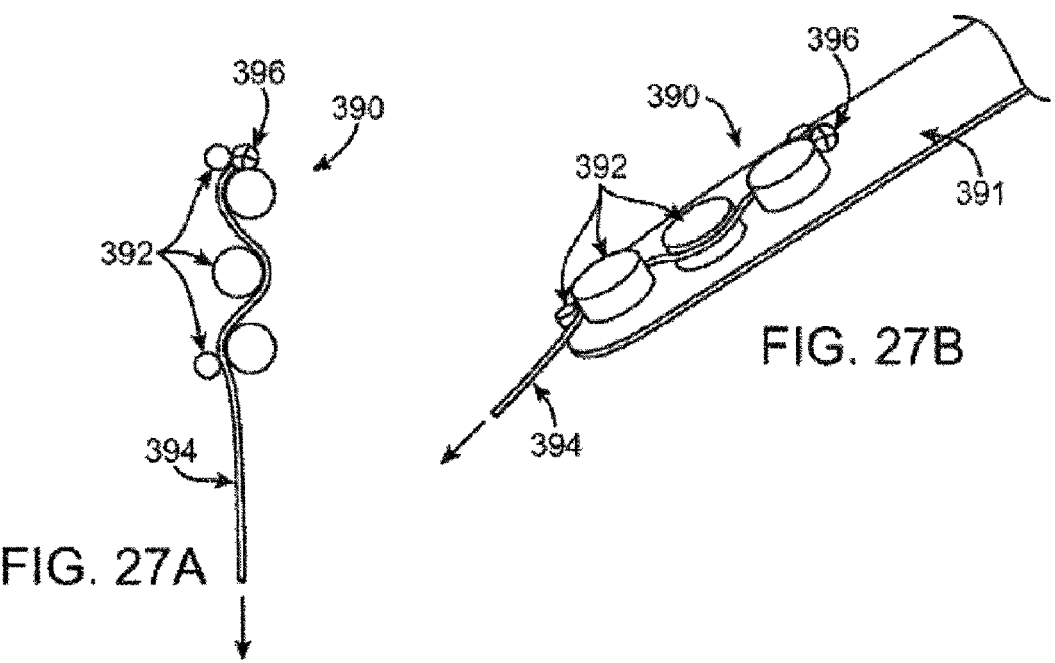
FIG. 27A  FIG. 27B

GUIDEWIRE EXCHANGE SYSTEMS TO TREAT SPINAL STENOSIS

CROSS-REFERENCE TO RELATED APPLICATIONS

This application is claims the benefit as a continuation-in-part of pending U.S. patent application Ser. No. 11/251,199, filed on Oct. 15, 2005, titled "Devices and Methods for Tissue Modification"; which claims the benefit of U.S. Provisional Patent Application Ser. No. 60/685,190, filed on May 27, 2005, titled "Methods and Apparatus for Selective Surgical Removal of Tissue"; U.S. Provisional Patent Application Ser. No. 60/681,719, filed May 16, 2005, titled "Methods and Apparatus for Selective Surgical Removal of Tissue"; U.S. Provisional Patent Application Ser. No. 60/681,864, filed May 16, 2005, titled "Methods and Apparatus for Selective Surgical Removal of Tissue"; U.S. Provisional Patent Application Ser. No. 60/622,865, filed Oct. 28, 2004, titled "Methods and Apparatus for Selective Surgical Removal of Tissue"; and U.S. Provisional Patent Application Ser. No. 60/619,306, filed Oct. 15, 2004, titled "Methods and Apparatus for the Treatment of Tissue Impingement in the Spine".

This application also claims the benefit as a continuation-in-part of pending U.S. patent application Ser. No. 11/468,247, filed on Aug. 29, 2006, titled "Tissue Access Guidewire System and Method." Each of these patent applications is herein incorporated by reference in their entirety.

BACKGROUND OF THE INVENTION

The devices, methods and systems described herein relate generally to medical/surgical devices and methods. More specifically, they may relate to guidewire systems and methods for advancing one or more surgical devices between tissues in a patient.

In recent years, less invasive (or "minimally invasive") surgical techniques have become increasingly more popular, as physicians, patients and medical device innovators have sought to achieve similar or improved outcomes, relative to conventional surgery, while reducing the trauma, recovery time and side effects typically associated with conventional surgery. Developing less invasive surgical methods and devices, however, can pose many challenges. For example, some challenges of less invasive techniques include working in a smaller operating field, working with smaller devices, and trying to operate with reduced or even no direct visualization of the structure (or structures) being treated. These challenges are compounded by the fact that target tissues to be modified often reside very close to one or more vital, non-target tissues, which the surgeon hopes not to damage. One of the initial obstacles in any given minimally invasive procedure, therefore, is positioning a minimally invasive surgical device in a desired location within the patient to perform the procedure on one or more target tissues, while avoiding damage to nearby non-target tissues.

Examples of less invasive surgical procedures include laparoscopic procedures, arthroscopic procedures, and minimally invasive approaches to spinal surgery, such as a number of less invasive intervertebral disc removal, repair and replacement techniques.

One area of spinal surgery in which a number of less invasive techniques have been developed is the treatment of spinal stenosis. Spinal stenosis occurs when neural and/or neurovascular tissue in the spine becomes impinged by one or more structures pressing against them, causing one or more symptoms. This impingement of tissue may occur in one or more of several different areas in the spine, such as in the central spinal canal, or more commonly in the lateral recesses of the spinal canal and/or one or more intervertebral foramina.

FIGS. 1-3 show various partial views of the lower (lumbar) region of the spine. FIG. 1 shows an approximate top view of a vertebra with the cauda equina (the bundle of nerves that extends from the base of the spinal cord through the central spinal canal) shown in cross section and two nerve roots exiting the central spinal canal and extending through intervertebral foramina on either side of the vertebra. The spinal cord and cauda equina run vertically along the spine through the central spinal canal, while nerve roots branch off of the spinal cord and cauda equina between adjacent vertebrae and extend through the intervertebral foramina. Intervertebral foramina may also be seen in FIGS. 2 and 3, and nerves extending through the foramina may be seen in FIG. 2.

One common cause of spinal stenosis is buckling and thickening of the ligamentum flavum (one of the ligaments attached to and connecting the vertebrae), as shown in FIG. 1. (Normal ligamentum flavum is shown in cross section in FIG. 3) Buckling or thickening of the ligamentum flavum may impinge on one or more neurovascular structures, dorsal root ganglia, nerve roots and/or the spinal cord itself. Another common cause of neural and neurovascular impingement in the spine is hypertrophy of one or more facet joints (or "zygopophaseal joints"), which provide articulation between adjacent vertebrae. (Two vertebral facet superior articular processes are shown in FIG. 1. Each superior articular process articulates with an inferior articular process of an adjacent vertebra to form a zygopophaseal joint. Such a joint is labeled in FIG. 3.) Other causes of spinal stenosis include formation of osteophytes (or "bone spurs") on vertebrae, spondylolisthesis (sliding of one vertebra relative to an adjacent vertebra), facet joint synovial cysts, and collapse, bulging or herniation of an intervertebral disc into the central spinal canal. Disc, bone, ligament or other tissue may impinge on the spinal cord, the cauda equina, branching spinal nerve roots and/or blood vessels in the spine to cause loss of function, ischemia and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stenosis include systemic medications and physical therapy. Epidural steroid injections may also be utilized, but they do not provide long lasting benefits. When these approaches are inadequate, current treatment for spinal stenosis is generally limited to invasive surgical procedures to remove ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIGS. 1 and 2) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints). In cases where a bulging intervertebral disc contributes to neural impingement, disc material may be removed surgically in a discectomy procedure.

Removal of vertebral bone, as occurs in laminectomy and facetectomy, often leaves the affected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Discectomy procedures require entering through an incision in the patient's abdomen and navigating through the abdominal anatomy to arrive at the spine. Thus, while laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients. Although a number of less invasive techniques and devices for spinal stenosis surgery have been developed, these techniques still typically require removal of significant amounts of vertebral bone and, thus, typically require spinal fusion.

Therefore, it would be desirable to have less invasive surgical methods and systems for treating spinal stenosis. For example, it would be desirable to have devices or systems for positioning a less invasive device in a patient for performing a less invasive procedure. Ideally, such systems and devices would be less invasive than currently available techniques and thus prevent damage to non-target vertebral bone and neural and neurovascular structures. Also ideally, such systems and devices would also be usable (or adaptable for use) in positioning a surgical device in parts of the body other than the spine, such as in joints for performing various arthroscopic surgical procedures, between a cancerous tumor and adjacent tissues for performing a tumor resection, and the like.

In particular, it would be useful to provided devices, systems and methods for gaining access using a guidewire that could be easily exchanged to position and apply tension to a plurality of devices, including surgical devices such as tissue localization devices, tissue modification devices, or the like. Described herein are devices, methods and system which may address these needs.

SUMMARY OF THE INVENTION

Described herein are devices, systems and method for positioning, actuating and exchanging various tissue access, treatment, and localization devices. In particular, described herein are exchange systems using a guidewire which may be used to both position and/or actuate a variety of such devices, while allowing exchange of such devices. Systems including these guidewires may be referred to herein as "exchange systems", "guidewire systems," "guidewire exchange systems" or the like.

For example, described herein are methods of exchanging a surgical device while treating a patient. These methods may include the steps of advancing a guidewire at least partially around a target tissue in a patient so that the proximal end of the guidewire extends from a first site on the patient and the distal end of the guidewire extends from a second site on the patient, coupling the proximal end of the guidewire on or near the distal end of a first surgical device, positioning the first surgical device by pulling the distal end of the guidewire, de-coupling the proximal end of the guidewire from the first surgical device, coupling the proximal end of the guidewire to a second surgical device, and positioning the second surgical device by pulling the distal end of the guidewire.

In some variations, the method may also include the step of withdrawing the first surgical device from the patient by pulling on the proximal end of the first surgical device. For example, the surgical device may be a relatively elongate device having a flexible distal end. The distal region of the device is preferably low-profile, and may be flat or thin. Surgical devices appropriate for use with the methods and systems described herein may be pulled into the subject using the guidewire, so that the proximal end of the surgical device (or a connector connected to the proximal end) remains outside of the patient. Thus, the first surgical device comprises an elongate surgical device having a flexible distal end. For example, the surgical device may be a tissue modification device (e.g., having a surface including one or more tissue modification elements).

The method may also include the step of urging the first surgical device against the target tissue by applying tension to either or both of the first surgical device extending from the first site and the guidewire extending from the second site. Similarly, the method may also include the step of urging the second surgical device against the target tissue by applying tension to either or both of the second surgical device extending from the first site and the guidewire extending from the second site.

The step of advancing the guidewire may include advancing the guidewire through a spinal foramen, particularly an intervertebral foramen.

Neural tissue localization may also be included as a part of the methods described herein. It may be particularly beneficial to confirm that neural tissue (e.g., a nerve) is not located between the target tissue and the guidewire before performing a procedure on the target tissue. Any appropriate tissue localization step may be used. For example, the tissue adjacent to the pathway of the guidewire may be directly visualized (using an endoscope, etc.), or indirectly visualized (using a medical imaging technology). Electrical tissue stimulation may be used. Examples of tissue localization methods, devices and systems that may be used can be found in U.S. patent application Ser. No. 12/060,229 (titled "SYSTEM AND APPARATUS FOR NEURAL LOCALIZATION"), filed Mar. 31, 2008, herein incorporated by reference in its entirety. In some variations, an electrical current is applied to the tissue adjacent the pathway of the guidewire to stimulate a nerve. Stimulation can be detected (e.g., by muscle twitch, EMG, etc.). Thus, the step of advancing the guidewire may include the step of confirming that a non-target nerve is not between the target tissue and the path of the guidewire, and in some variations the step of confirming that a non-target nerve is not between the target tissue and the path of the guidewire comprises applying electrical energy to the tissue.

Also described herein are methods of exchanging a surgical device while treating a patient that include the steps of: advancing a guidewire through an intervertebral foramen and at least partially around a target tissue in a patient so that the proximal end of the guidewire extends from a first site on the patient and the distal end of the guidewire extends from a second site on the patient, coupling the proximal end of the guidewire on or near the distal end of a first surgical device, pulling the distal end of the guidewire to position the first surgical device adjacent the target tissue, removing the first surgical device from the patient while leaving the guidewire in the patient, de-coupling the proximal end of the guidewire from the first surgical device, coupling the proximal end of the guidewire to a second surgical device, and pulling the distal end of the guidewire to position the second surgical device.

Also described herein are methods of treating a patient, the method including the step of advancing a distal end of a guidewire into the patient's body from a first site, advancing the distal end at least partially around a target tissue, extending the distal end of the guidewire out of the body from a second site, while maintaining a proximal end of the guidewire outside the body at the first site, coupling the proximal end of the guidewire on or near a distal end of a surgical device, and pulling the distal end of the guidewire to guide at least a portion of the surgical device to a desired position adjacent to the target tissue.

In many of the methods described herein, the guidewire is inserted through the patient's body so that both the proximal and distal ends of the guidewire extend from the body, typically (but not necessarily) from separate entry and exit sites. The path that the guidewire takes is curved or bent, and the bend occurs adjacent to the target tissue. This may allow the guidewire or a device attached to the guidewire to be urged specifically against the target tissue by applying tension. For example, one or both ends of the guidewire (or a device attached to the guidewire) may be pulled, urging the device against the target tissue. Thus, the method may include the step of urging the surgical device against the target tissue by applying tension to either or both of the surgical device extending from the first site and the guidewire extending from the second site.

The step of coupling the proximal end of the guidewire on or near the distal end of the surgical device may include coupling the proximal end of the guidewire to the surgical device with at least one coupling member. For example, the step may include engaging a guidewire coupling member on the surgical device with the distal end of the guidewire.

In some variations, the method also includes the step of locking the proximal end of the guidewire on or near a distal end of a surgical device. The guidewire may be permanently or releasably locked to the surgical device. For example, the guidewire may be permanently locked by crimping the coupling member or be lodging the guidewire (e.g., the shaped proximal end of the guidewire) within the coupling member of the surgical device.

The method may also include the step of performing a surgical procedure on the target tissue using the surgical device. For example, the step of performing a surgical procedure may include reciprocating the surgical device by pulling on either or both of the surgical device extending from the first site and the guidewire extending from the second site.

The method may also include the step of withdrawing the surgical device proximally from the patient. In some variations, the method also includes de-coupling the proximal end of the guidewire from the surgical device and coupling the proximal end of the guidewire on or near a distal end of a second surgical device.

Also described herein are methods for guiding at least a portion of a surgical device to a desired position between two tissues in a patient's body. These methods may include the steps of: advancing a distal end of a guidewire into the patient's body, between two tissues, and out of the body, while maintaining a proximal end of the guidewire outside the body, coupling the proximal end of the guidewire with at least one coupling member on or near a distal end of a surgical device, and pulling the distal end of the guidewire to guide at least a portion of the surgical device to a desired position between the two tissues.

Also described herein are methods for performing a procedure on a target tissue in a patient's body. These methods may include coupling a proximal end of a guidewire with at least one coupling member on or near a distal end of a surgical device, pulling a distal end of the guidewire to guide at least a portion of the surgical device to a desired position between the two tissues, such that an active portion of the surgical device faces target tissue and an atraumatic portion of the surgical device faces non-target tissue, and performing a procedure on the target tissue, using the surgical device.

INCORPORATION BY REFERENCE

All publications and patent applications mentioned herein are hereby incorporated by reference in their entirety as if each individual publication or patent application was specifically and individually indicated to be incorporated by reference.

BRIEF DESCRIPTION OF THE DRAWINGS

FIGS. 14A and 14B are perspective views of a distal end of a tissue modification device with guidewire coupling member and a shaped guidewire.

FIGS. 15A and 15C are perspective views of a guidewire coupling member and a shaped guidewire, demonstrating a method for coupling the two.

FIGS. 15B and 15D are top views of the guidewire coupling member and shape guidewire of FIGS. 15A and 15C.

FIGS. 15E and 15F are different perspective views of the guidewire coupling member of FIGS. 15A and 15C, without the shaped guidewire.

FIGS. 18A and 18B are top views of a single-cam guidewire coupling member.

FIG. 19 is a top view of a double-cam guidewire coupling member.

FIGS. 20A-20C are top views of a movable-piece guidewire coupling member.

FIGS. 25A and 25B are perspective views of a hooked guidewire and receiving guidewire coupling member.

FIGS. 26A and 26B are perspective views of a ball-and-socket guidewire and guidewire coupling member.

FIGS. 27A and 27B are top and perspective views, respectively, of a spool trap guidewire coupling member.

DETAILED DESCRIPTION OF THE INVENTION

In general, the guidewire systems described herein includes a guidewire and at least one surgical device that are configured so that the proximal end of the guidewire couples to the distal end of the guidewire. The guidewire typically has a distal end that is configured to extend from a subject's body and be manipulated, and a proximal end that includes a coupling member for coupling to the surgical device. The coupling member may be referred to as a device coupling member and may be located at or near the proximal end of the guidewire. Any appropriate surgical device or devices may be included as part of the guidewire system. The surgical device typically includes a coupling member on or near its distal end that is configured to mate with the coupling member on or near the proximal end of the guidewire. The device-side coupling member may be referred to as a guidewire coupling member.

Methods of using these systems, and particularly methods of quickly exchanging surgical devices during a procedure, are described in greater detail below.

Various embodiments of a guidewire system and method for positioning one or more surgical devices in a patient are provided. Although the following description and accompanying drawing figures generally focus on positioning various surgical devices in a spine, in alternative embodiments, guidewire systems and methods of the present invention may be used to position any of a number of devices in other anatomical locations in a patient's body.

Figure 1:
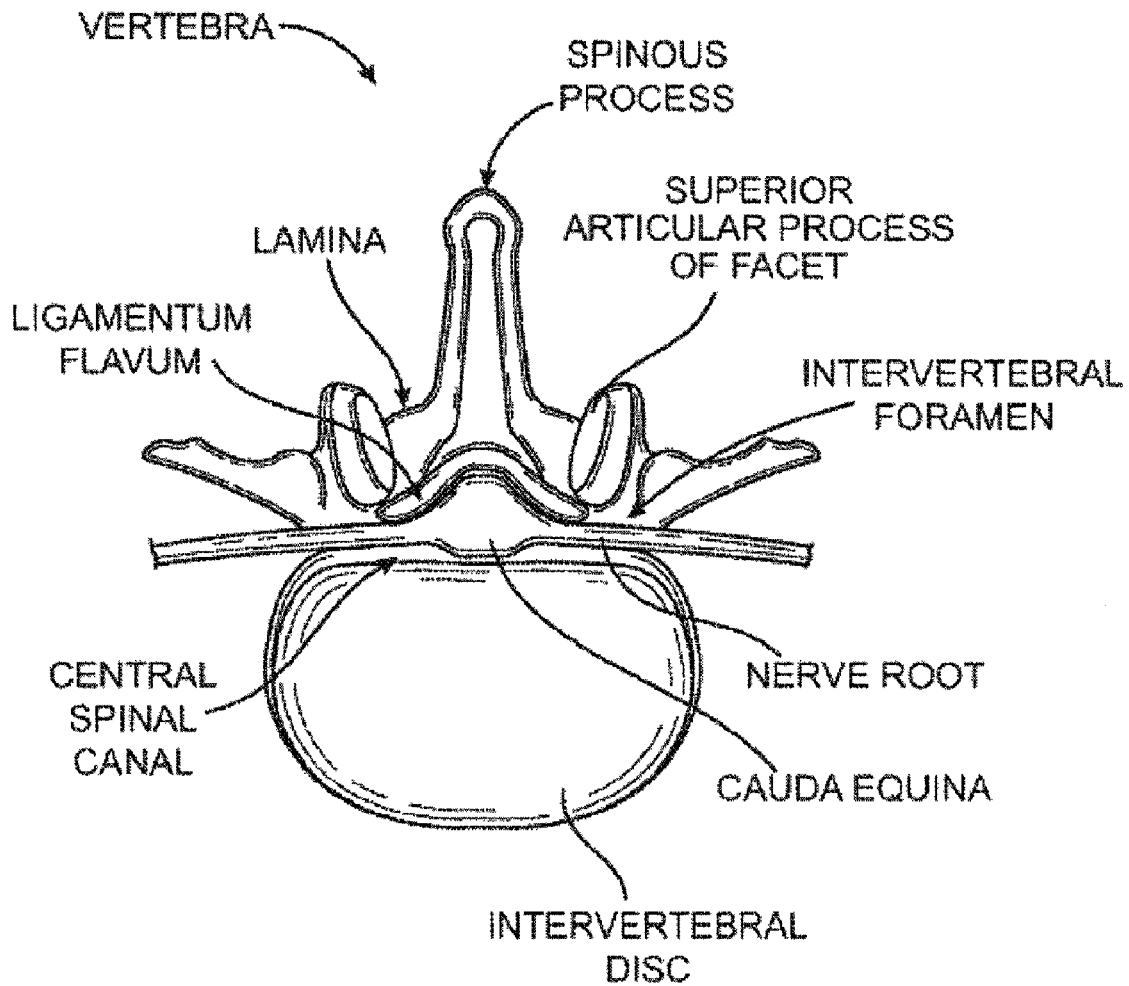
FIG. 1 is cross-sectional view of a spine, showing a top view of a lumbar vertebra, a cross-sectional view of the cauda equina, and two exiting nerve roots.
Figure 2:
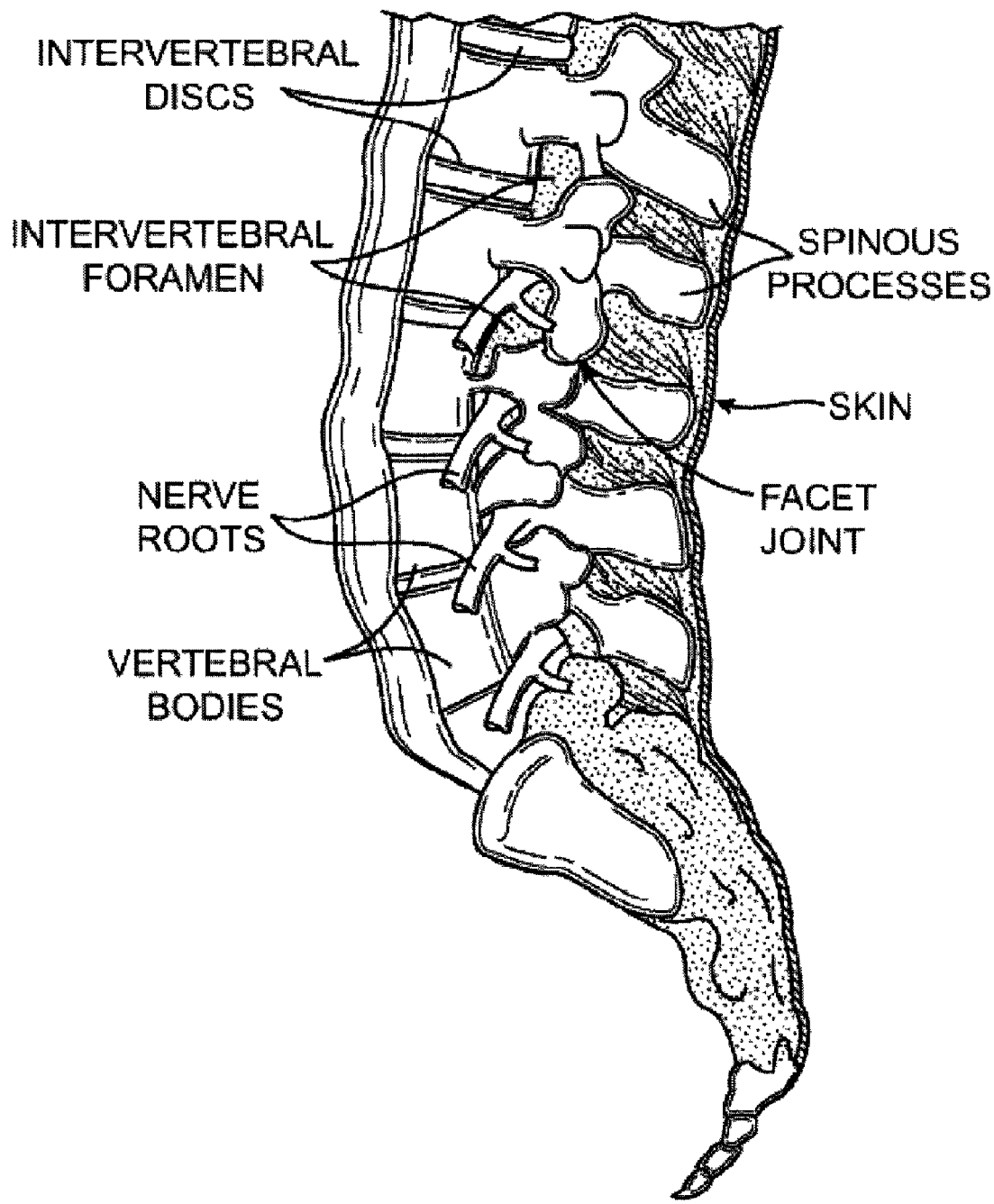
FIG. 2 is a left lateral view of the lumbar portion of a spine with sacrum and coccyx.
Figure 3:
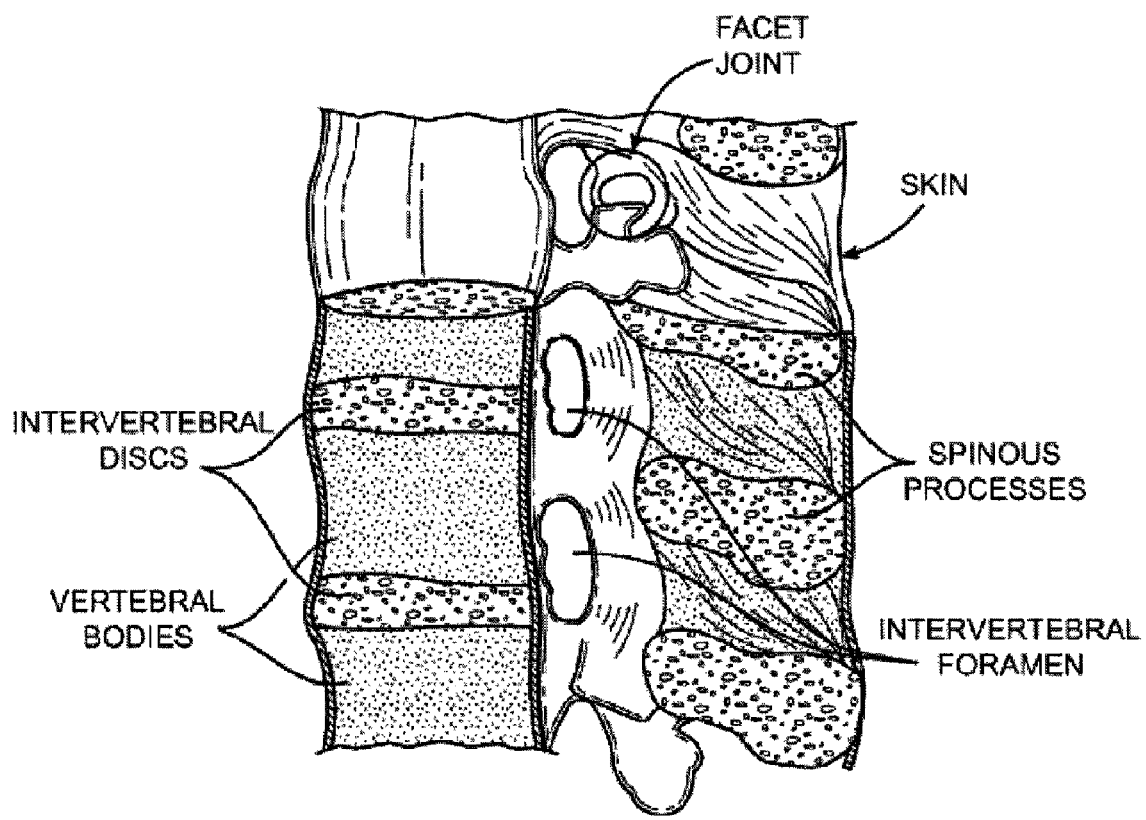
FIG. 3 is a left lateral view of a portion of the lumbar spine, showing only bone and ligament tissue and partially in cross section.
Figure 4:
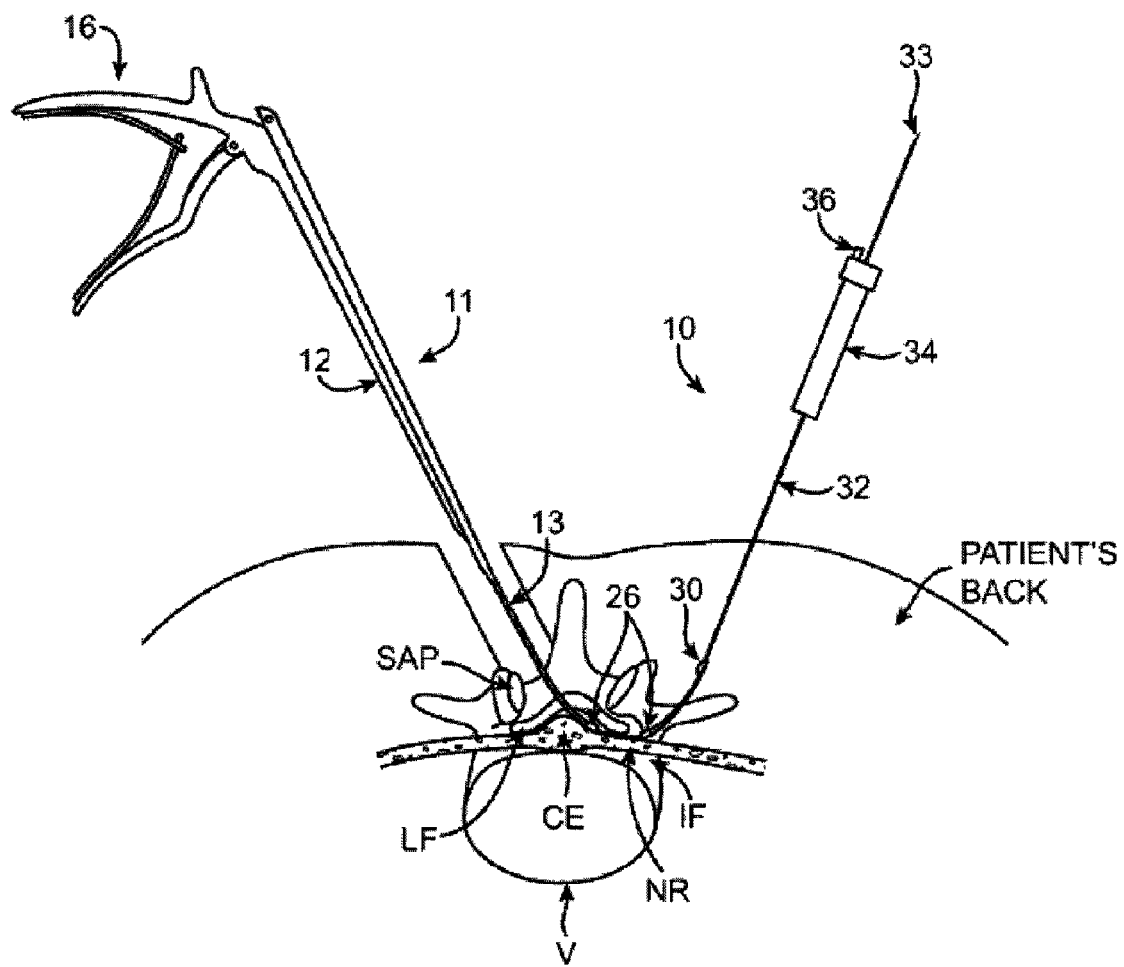
FIG. 4 is a cross-sectional view of a patient's back and spine with a side view of a guidewire and tissue modification system in place for performing a tissue removal procedure.

Referring to FIG. 4, one embodiment of a guidewire system 10 is shown coupled with a tissue cutting device 11 in position within a patient's spine. Further description of various embodiments of cutting device 11 may be found in U.S. patent application Ser. No. 11/461,740, entitled "Multi-Wire Tissue Cutter", and filed Aug. 1, 2006, the full disclosure of which is hereby incorporated by reference. A number of alternative embodiments of cutting devices, many of which may be used (or adapted for use) with guidewire system 10, are further described in U.S. patent application Ser. No.

11/375,265, entitled "Methods and Apparatus for Tissue Modification", and filed Mar. 13, 2006; Ser. No. 11/405,848, entitled "Mechanical Tissue Modification Devices and Methods", and filed Apr. 17, 2006; Ser. No. 11/406,486, entitled "Powered Tissue Modification Devices and Methods", and filed Apr. 17, 2006; and Ser. No. 11/429,377, entitled "Flexible Tissue Rasp", and filed May 4, 2006. The full disclosures of all of the foregoing references are hereby incorporated by reference.

As described in further detail in U.S. patent application Ser. No. 11/461,740, tissue cutting device 11 may include a shaft 12, a proximal handle 16, a flexible distal portion 13, two or more cutting blades 26 and a guidewire coupling member 30. Guidewire system 10 may include a guidewire 32 having a sharpened tip 33 (often referred to herein as the "sharpened distal tip") for facilitating advancement of guidewire 32 through tissue. Optionally, guidewire 32 may also include a device coupling member that is configured as a shaped member (not visible in FIG. 4) at the end opposite sharpened tip 33 (often referred to herein as the guidewire "proximal end") for coupling with coupling member 30. Guidewire system 10 may also include a guidewire handle 34 (or "distal handle") for coupling with guidewire 32, which in some cases may include a tightening member 36 for securing a portion of guidewire 32 within guidewire handle 34.

In some embodiments, cutting device 11 may be advanced into a patient's back through an incision 20, which is shown in FIG. 4 as an open incision but which may be a minimally invasive or less invasive incision in alternative embodiments. In some embodiments, device 11 may be advanced by coupling guidewire connector 30 with guidewire 32 that has been advanced between target and non-target tissues, and then pulling guidewire 32 to pull device 11 between the tissues. Various embodiments of such a method for delivering a device are described in further detail below. Generally, guidewire system 10 may be used to pull flexible distal portion 13 into place between tissues in hard-to-reach or tortuous areas of the body, such as between a nerve root (NR) and facet joint and through an intervertebral foramen (IF). Generally, flexible portion 13 may be advanced to a position such that blades 26 face tissue to be cut in a tissue removal procedure ("target tissue") and a non-cutting surface (or surfaces) of flexible portion 13 faces non-target tissue, such as nerve and/or neurovascular tissue. In the embodiment shown in FIG. 4, blades 26 are positioned to cut ligamentum flavum (LF) and may also cut hypertrophied bone of the facet joint, such as the superior articular process (SAP). (Other anatomical structures depicted in FIG. 4 include the vertebra (V) and cauda equina (CE)). In various alternative embodiments, flexible portion 13 may be replaced with a curved, rigid portion, a steerable portion, a straight portion with a distal extension or the like. The configuration, dimensions, flexibility, steerability, materials and the like of flexible portion 13 may be adjusted, in alternative embodiments, depending on a type of tissue or anatomical structure to be accessed or modified.

Before or after blades 26 are located in a desired position, guidewire 32 may be removably coupled with guidewire handle 34, such as by passing guidewire 32 through a central bore in handle 34 and moving tightening member 36 to secure a portion of guidewire 32 within handle 34. A physician (or two physicians or one physician and an assistant) may then pull on proximal handle 16 and distal handle 34 to apply tensioning force to guidewire 32 and cutting device 11 and to urge the cutting portion of device 11 against ligamentum flavum (LF), superior articular process (SAP), or other tissue to be cut. Proximal handle 16 may then be actuated, such as by squeezing in the embodiment shown, to cause one or both blades 26 to move toward one another to cut tissue. Proximal handle 16 may be released and squeezed as many times as desired to remove a desired amount of tissue. When a desired amount of tissue has been cut, guidewire 32 may be released from distal handle 34, and cutter device 11 and guidewire 32 may be removed from the patient's back.

With reference now to FIGS. 5A-5I, one embodiment of a method for advancing a tissue modifying device into a patient's body using a guidewire delivery system is shown. Although this method is shown in reference to placement of a device in a spine, in various alternative embodiments, such a method may be used to place similar or alternative tissue modification devices in other locations in a human body, such as between tissues in a joint space, in the abdominal cavity, or in the carpal tunnel of the wrist, between bone and soft tissue in other parts of the body, and the like.

Figure 5A:
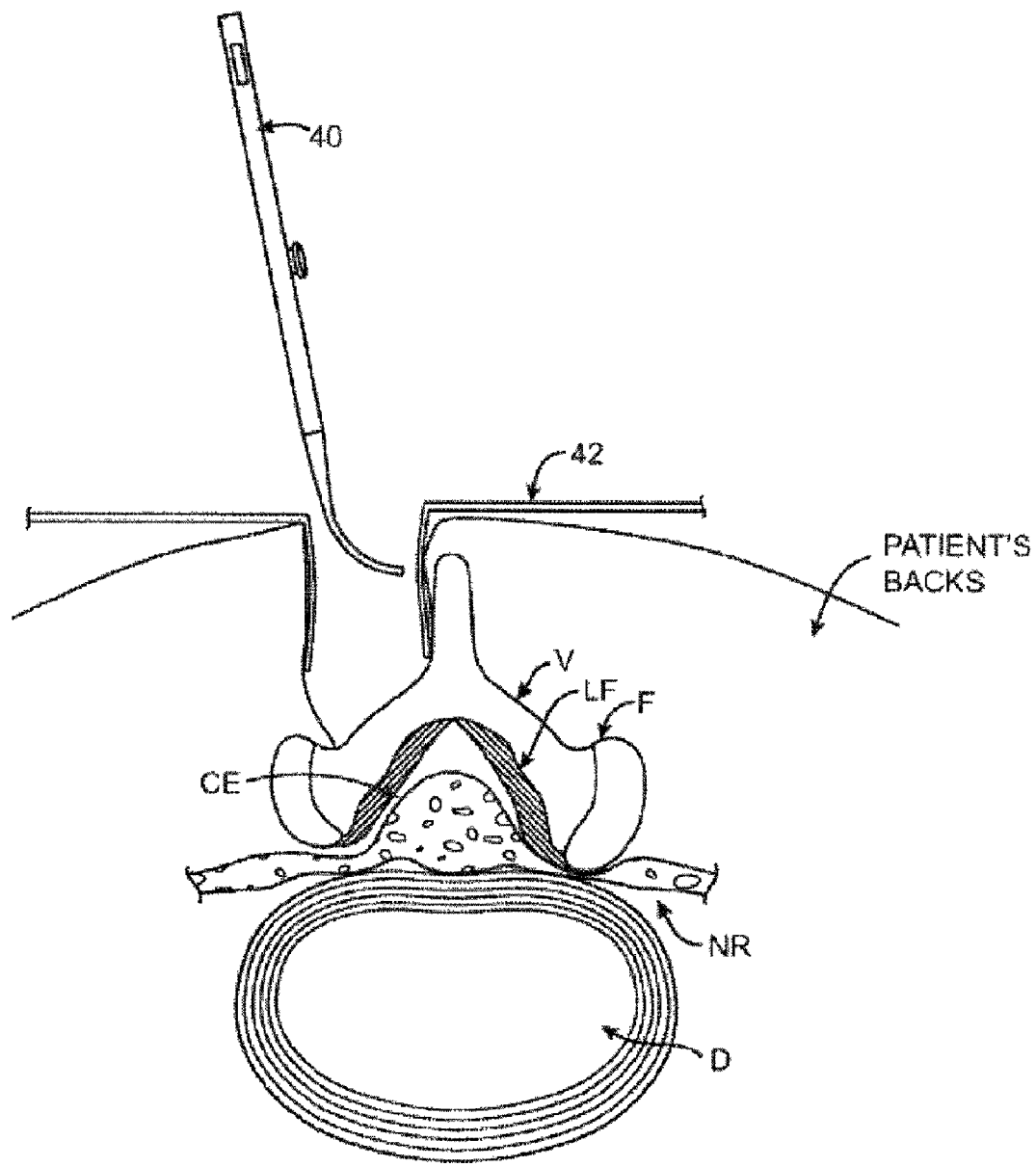
FIGS. 5A-5I illustrate one variation of a method for advancing a tissue modifying device into a patient's body using a guidewire delivery system.
Figure 5B:
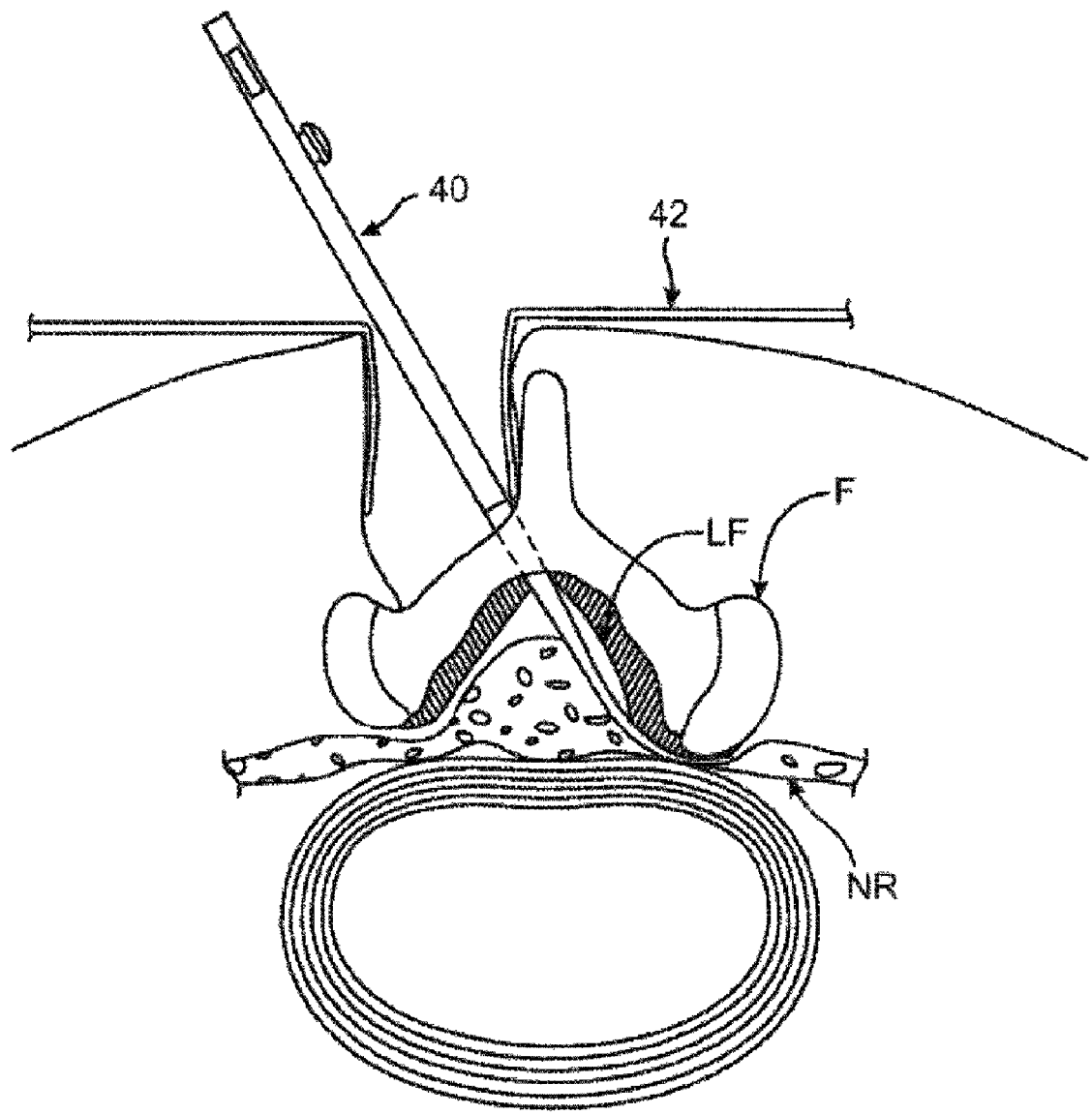
Figure 5C:
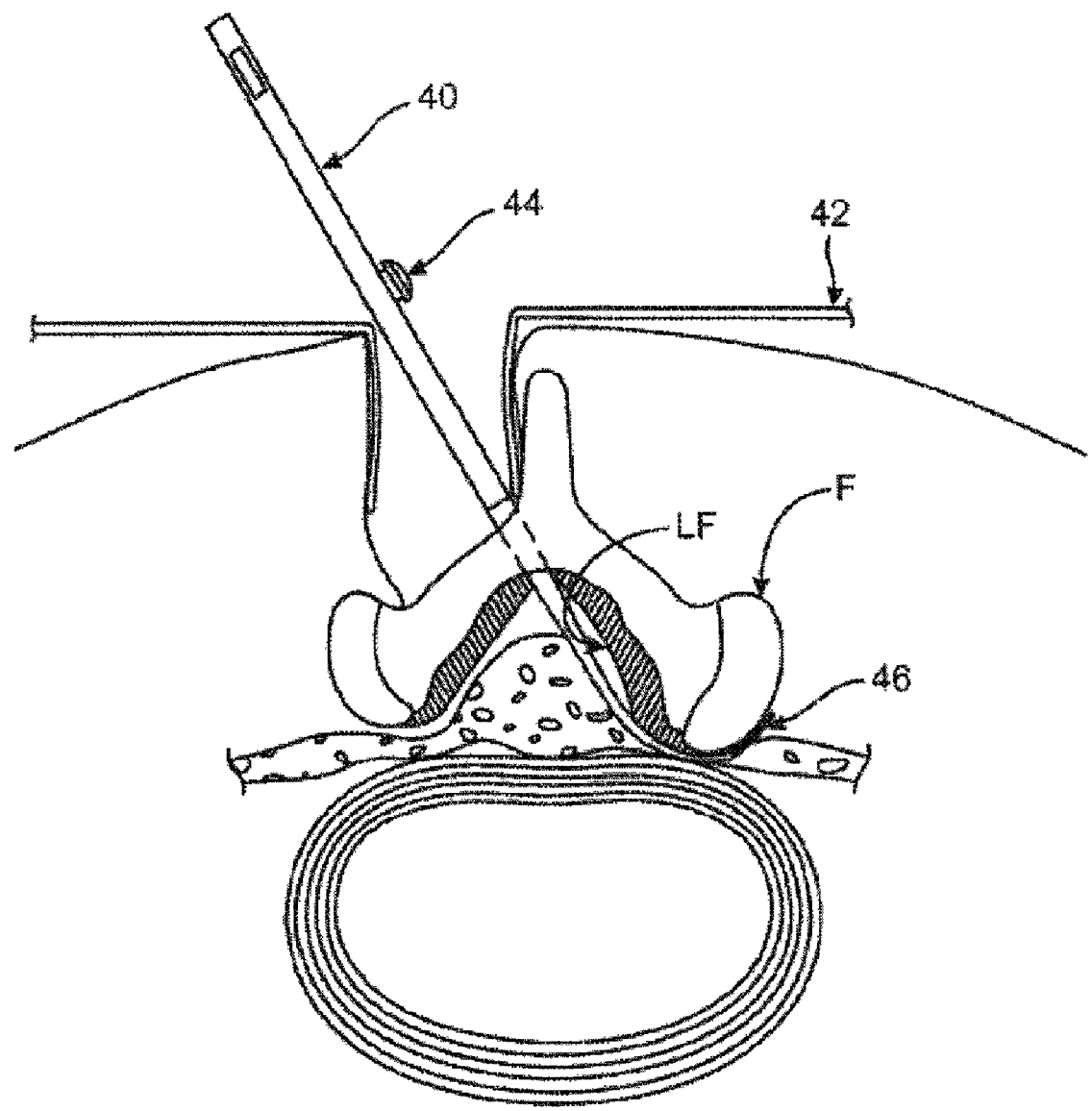
Figure 5D:
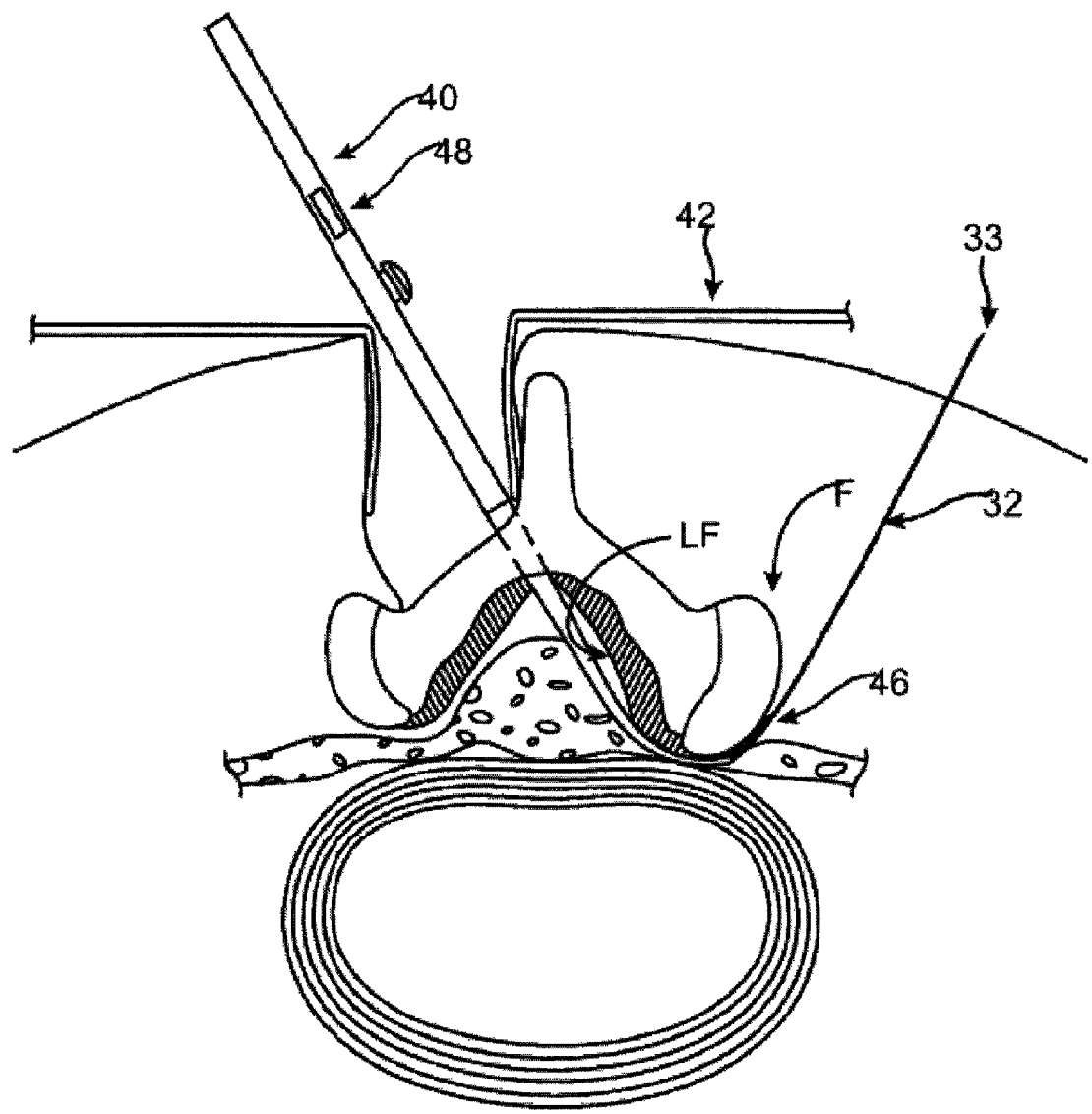
Figure 5E:
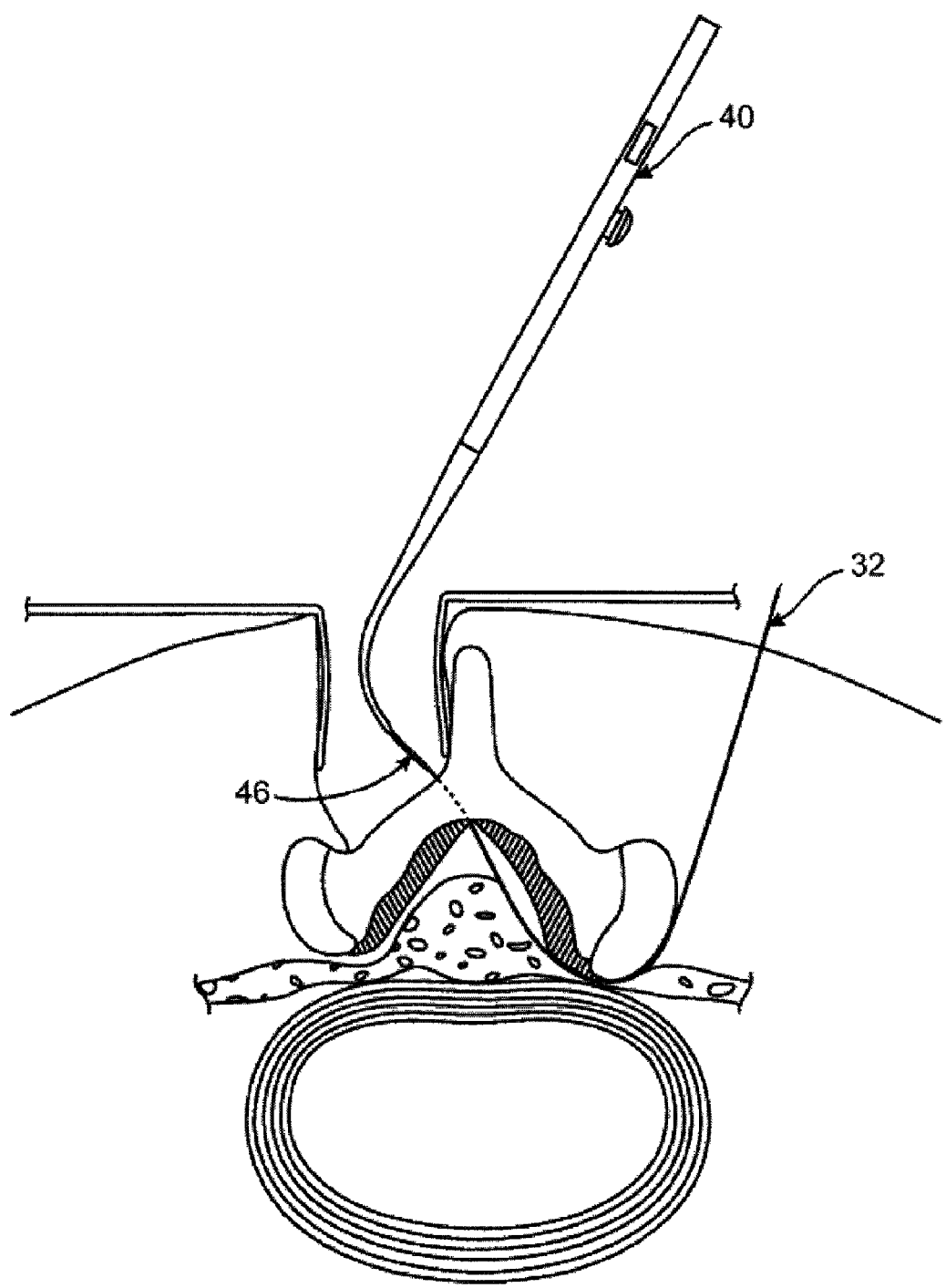
Figure 5F:
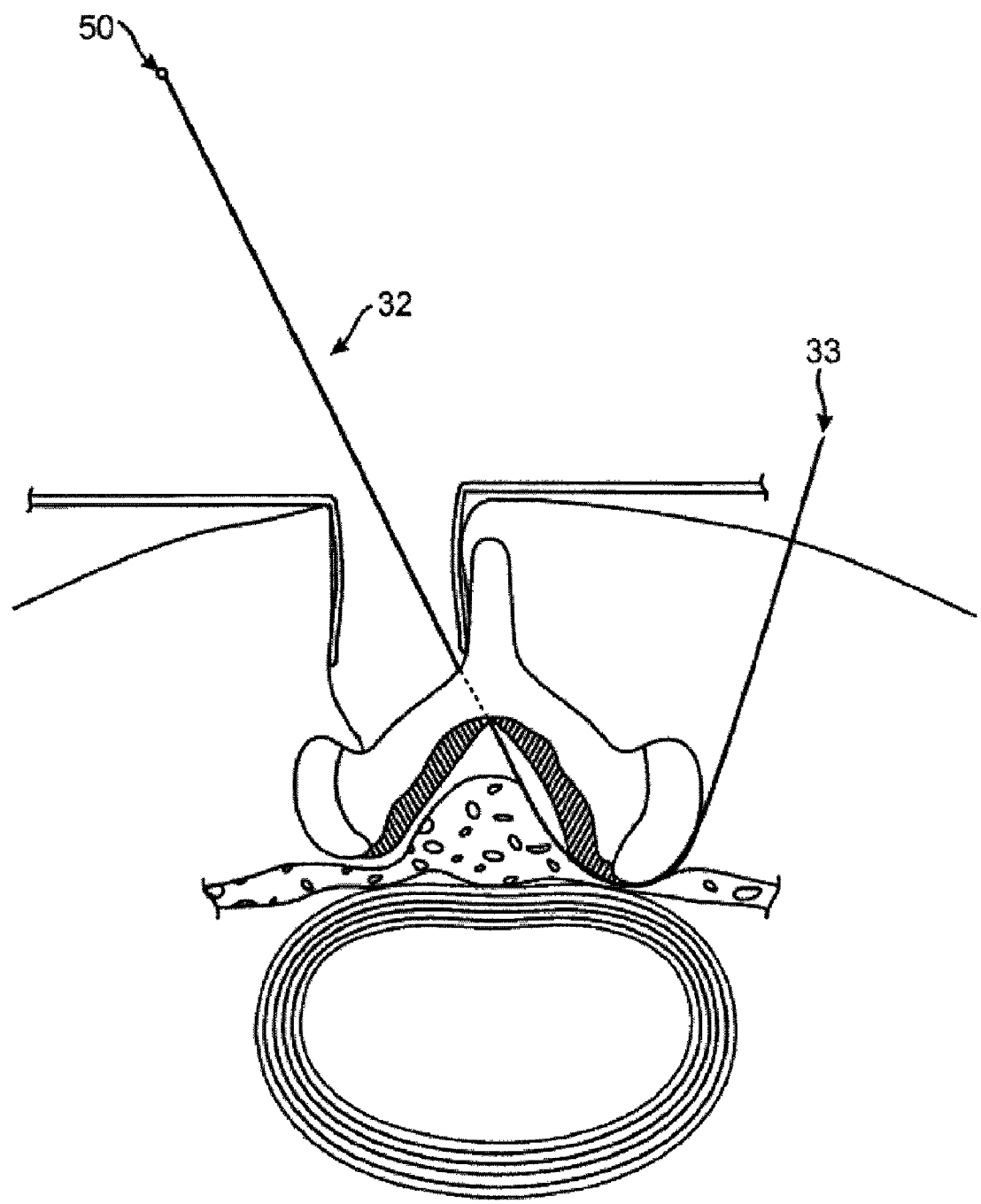

Referring to FIG. 5A, in one embodiment of a method for advancing a tissue modifying device, a probe 40 may be inserted into a patient's back using an open technique facilitated by retractors 42. Target tissues of a procedure, in this embodiment, may include ligamentum flavum (LF) and/or facet joint (F) tissue of a vertebra (V), which may impinge on non-target tissues, such as nerve root (NR) and/or cauda equina (CE), of the lumbar spine. Also depicted in FIG. 5A is an intervertebral disc (D). In FIG. 5B, a curved distal portion of probe 40 has been advanced to a position between target ligamentum flavum (LF) and non-target nerve root (NR) tissues. As depicted in FIG. 5C, in some embodiments, a curved guide member 46 may next be advanced out of an aperture on the curved distal portion of probe 40. In one embodiment, for example, guide member 46 may be housed within probe and advanced out of the distal aperture by advancing a slide member 44 on the shaft of probe 40. Next, as shown in FIG. 5D, guidewire 32 may be advanced through guide member 46 and out of the patient's back, using sharpened tip 33 to facilitate passage through the patient's back tissue. Probe 40 may then be removed, as shown in FIG. 5E, leaving guidewire 32 in place between the target and non-target tissues, as shown in FIG. 5F. Also shown in FIG. 5F is a shaped member 50 (in this embodiment, a ball) on the proximal end of guidewire 32.

Further description of methods, devices and systems for advancing a guidewire between tissues using a probe are provided in U.S. patent application Ser. No. 11/429,377, entitled "Spinal Access and Neural Localization" and filed on Jul. 13, 2006, the full disclosure of which is hereby incorporated by reference. As described in that reference, in some embodiments, the curved distal portion of probe 40, curved guide member 46, or both may include one, two or more electrodes to help locate nerve tissue before placing guidewire 32. Such neural localization helps ensure that guidewire 32 is positioned between target and non-target tissue, which in turn helps ensure that a tissue modification device (or devices) placed using guidewire 32 are oriented so that a tissue modifying portion (or portions) of the device face and act on target tissue and not on non-target tissue such as neural tissue.

Figure 5G:
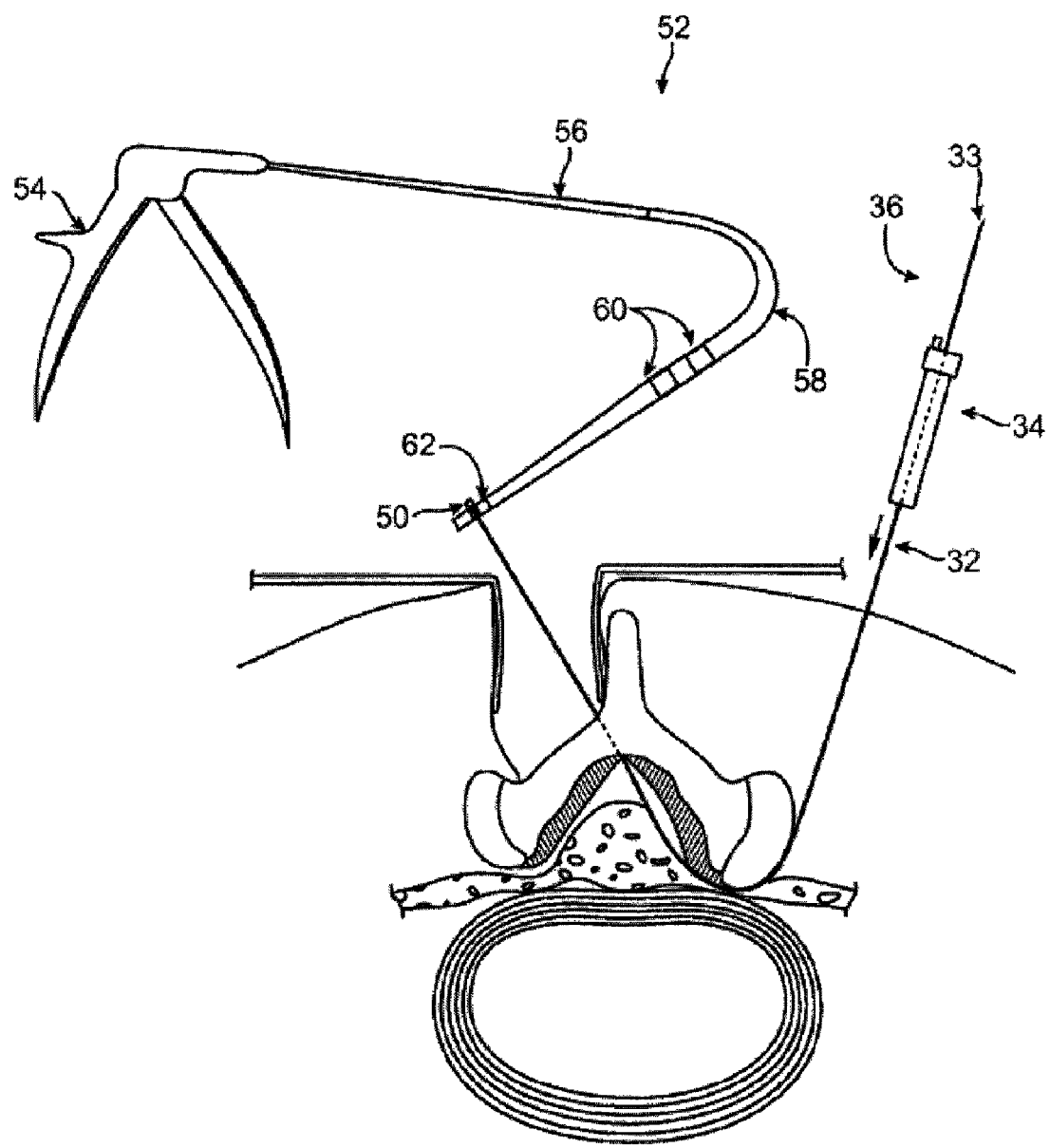

Referring now to FIG. 5G, once guidewire 32 is positioned between tissues, its proximal end with shaped member 50 may be coupled with a coupling member (i.e., guidewire coupling member 62) on a distal end of a tissue modification device 52. Tissue modification device 52, in one embodiment, may include a proximal handle 54, a rigid proximal shaft portion 56, a flexible distal shaft portion 58, tissue cutting blades 60, and coupling member 62. Coupling member 62, various embodiments of which are described in greater detail below, may be either attached to or formed in distal shaft portion 58. In some embodiments, such as the one depicted in FIG. 5G, to attach guidewire 32 to coupling member 62, guidewire 32 may be laid into a channel on coupling member 62, and guidewire 32 and/or distal portion 58 may be rotated, relative to one another, to lock shaped member 50 into coupling member. Various alternative embodiments for coupling guidewires 32 with coupling members 62 are described in greater detail below. Before, after or during coupling of guidewire 32 and tissue modification device 52, guidewire 32 may also be coupled with distal guidewire handle 34, such as by advancing distal handle 34 over guidewire 32 (solid-tipped arrow).

Figure 5H:
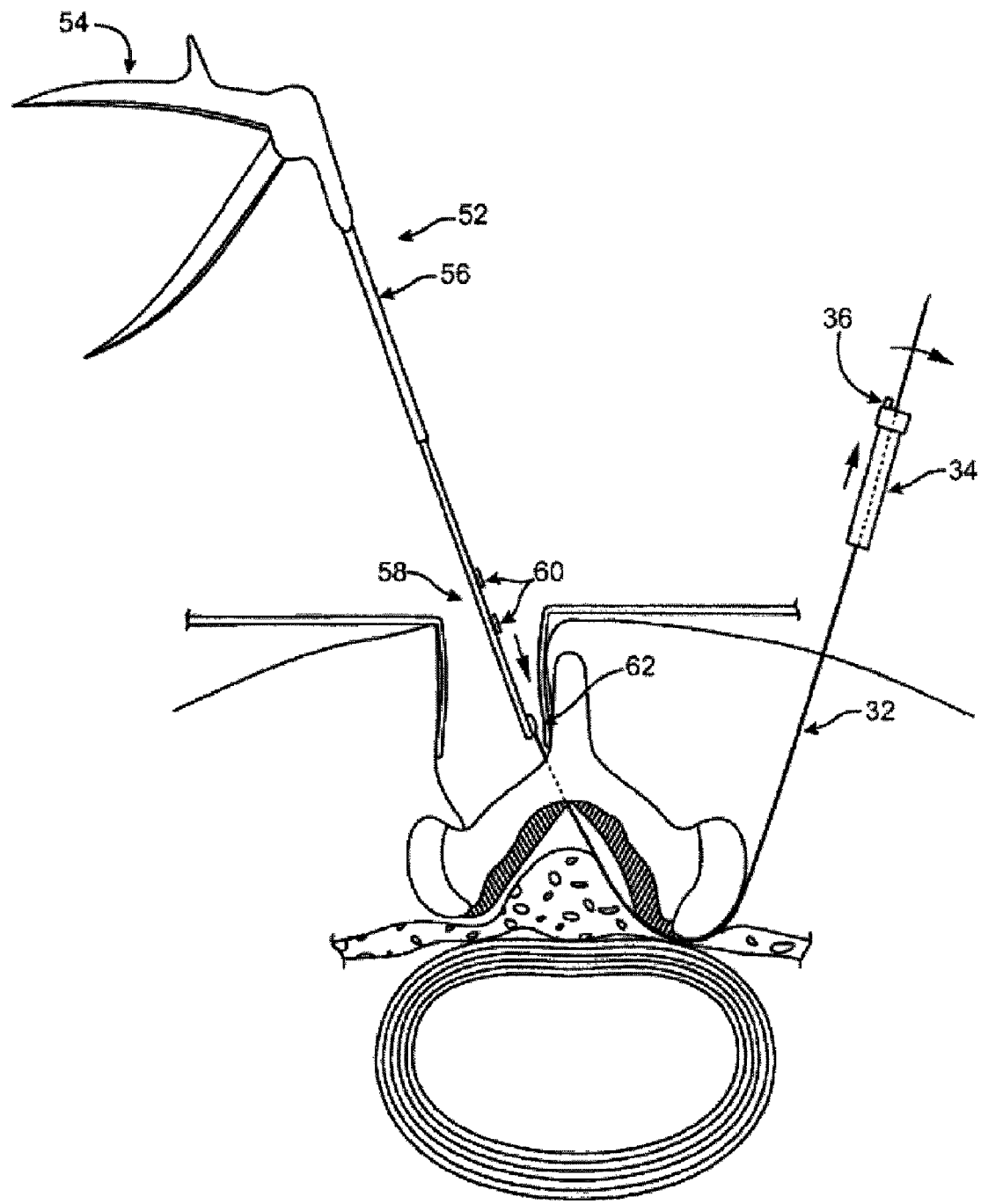
Figure 5I:
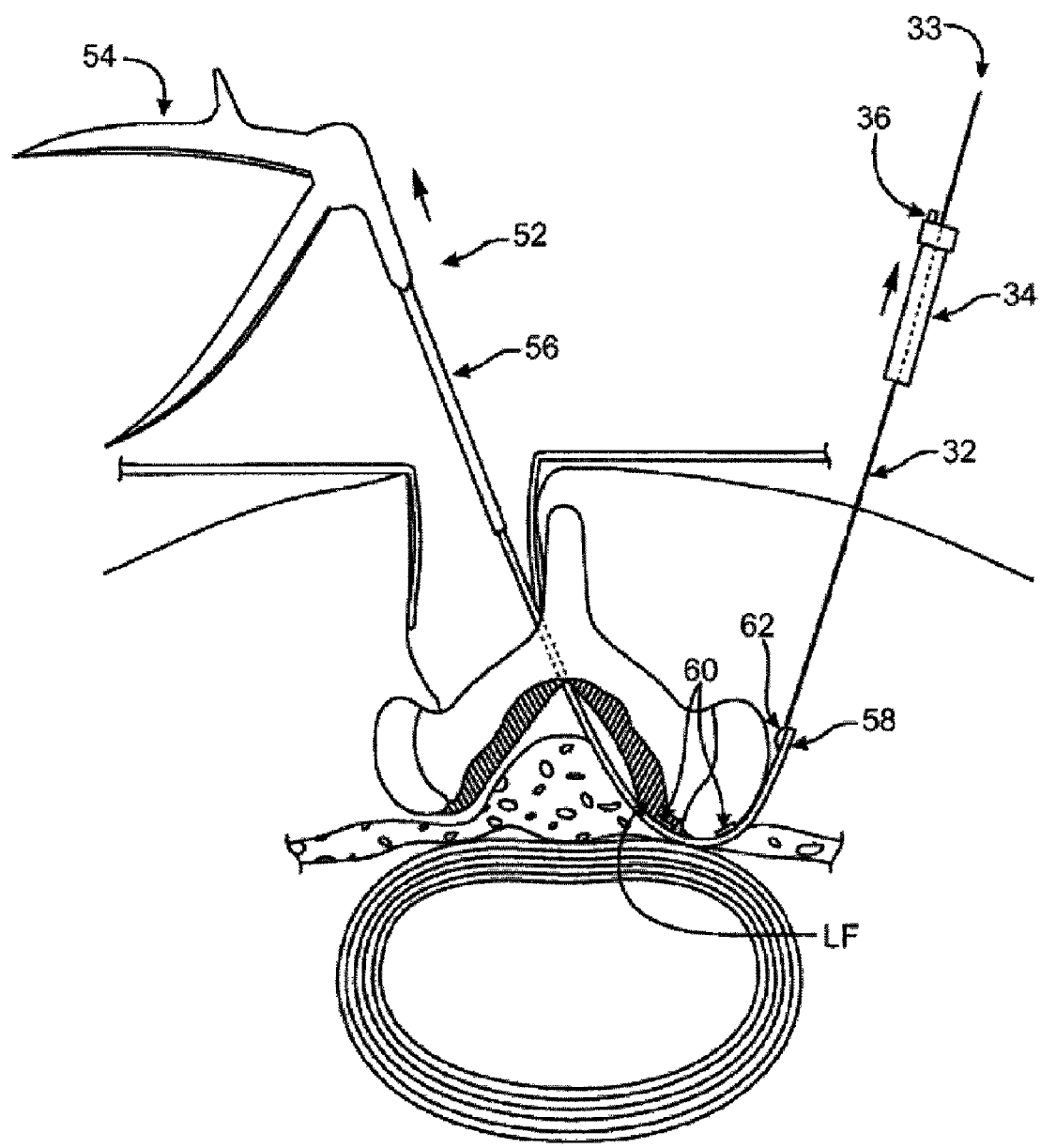

As depicted in FIG. 5H, tightening member 36 may next be moved (curved, solid-tipped arrow) to tighten distal handle 34 around guidewire 32. Distal handle 34 may then be pulled (straight, solid-tipped arrow) to pull guidewire 32 and thus advance distal shaft portion 58 of tissue modification device 52 into place between target and non-target tissues in the spine, as shown in FIG. 5I. Once device 52 is positioned as desired, as depicted in FIG. 5I, proximal handle 54 and distal handle 34 may be pulled (straight, solid-tipped arrows), to apply tensioning force to guidewire 32 and device 52 and thus urge flexible portion 58 and blades 60 against target tissue, such as ligamentum flavum (LF) and/or facet joint (F) tissue. Handle 54 may then be actuated (curved, double-tipped arrow) to cause blades 60 to cut target tissue. When a desired amount of tissue is cut, guidewire 32 may be released from distal handle 34, and tissue modification device 52 and guidewire 32 may be removed from the patient's back. Alternatively, the guidewire may be left at least partially in the body so that it can be used to position and/or actuate other surgical device. This method for advancing tissue modification device 52 using guidewire 32 is but one exemplary embodiment.

Various aspects of the method embodiment just described, such as the number or order of steps, may be changed without departing from the scope of the invention. Furthermore, a number of alternative embodiments of various devices and device elements are described below, which may be used in various embodiments of such a method. For example, in one alternative embodiment (not shown), probe 40 and tissue modification device 52 may be combined into one device. Such a device may include a guidewire lumen through which guidewire 32 may be passed. The combined device may be partially inserted into a patient, and guidewire 32 advanced between target and non-target tissues through the guidewire lumen. Shaped member 50 (device coupling member) of guidewire 32 may then catch on one or more coupling members 62 of the combined device (guidewire coupling member), to allow the device to be pulled into position between the target and non-target tissues. Guidewire 32 may then further be used to help apply tensioning force to the device to urge an active portion against target tissues. In another alternative embodiment, access to the intervertebral foramen may be achieved using a lateral approach, rather than a medial approach. These are but two examples of many alternative embodiments, and a number of other alternatives are contemplated.

Figure 6:
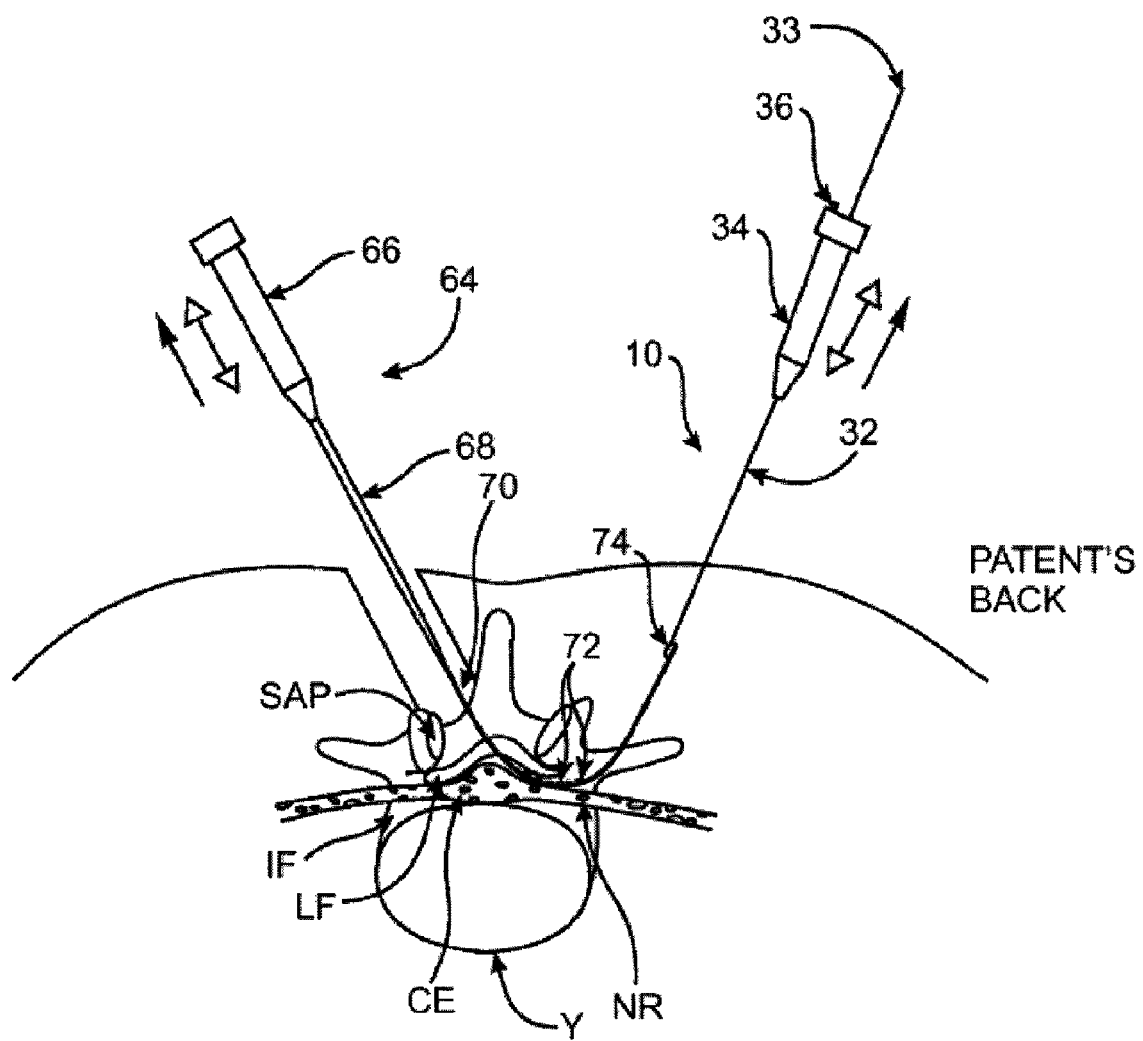
FIG. 6 is a cross-sectional view of a patient's back and spine and a side view of a rasp device and guidewire system.

With reference now to FIG. 6, guidewire system 10 is shown with an alternative embodiment including a tissue modification device 64, which may include a proximal handle 66, a rigid proximal shaft portion 68, and a distal flexible shaft portion 70. Multiple abrasive members 72 and a guidewire coupling member 74 may be coupled with one side of flexible shaft portion 70. In this embodiment, guidewire 32 may be coupled with coupling member 74 and used to pull distal shaft portion 70 of modification device 64 into place between target and non-target tissues. Proximal handle 66 and distal handle 34 may then be pulled/tensioned (solid-tipped arrows) to urge abrasive members 72 against the target tissue, and handles 66, 34 may further be used to reciprocate device 64 and guidewire 32 back and forth (hollow/double-tipped arrows) to modify the target tissue. Reciprocation and tensioning may be continued until a desired amount of tissue is removed, at which point guidewire 32 may be released from distal handle 34, and device 64 and guidewire 32 may be removed from the patient's back. In various embodiments, tissue modification device 64 may include any of a number of abrasive members 72, abrasive materials, or the like, which may be arrayed along distal shaft portion 70 for any desired length and in any desired configuration. Further examples of abrasive members 70, materials, surfaces and the like are described in U.S. patent application Ser. No. 11/429,377, which was previously incorporated by reference. In various alternative embodiments, shaft portions 68, 70 may both be rigid or may both be flexible and may have different cross-sectional shapes or the same shape.

Figure 7:
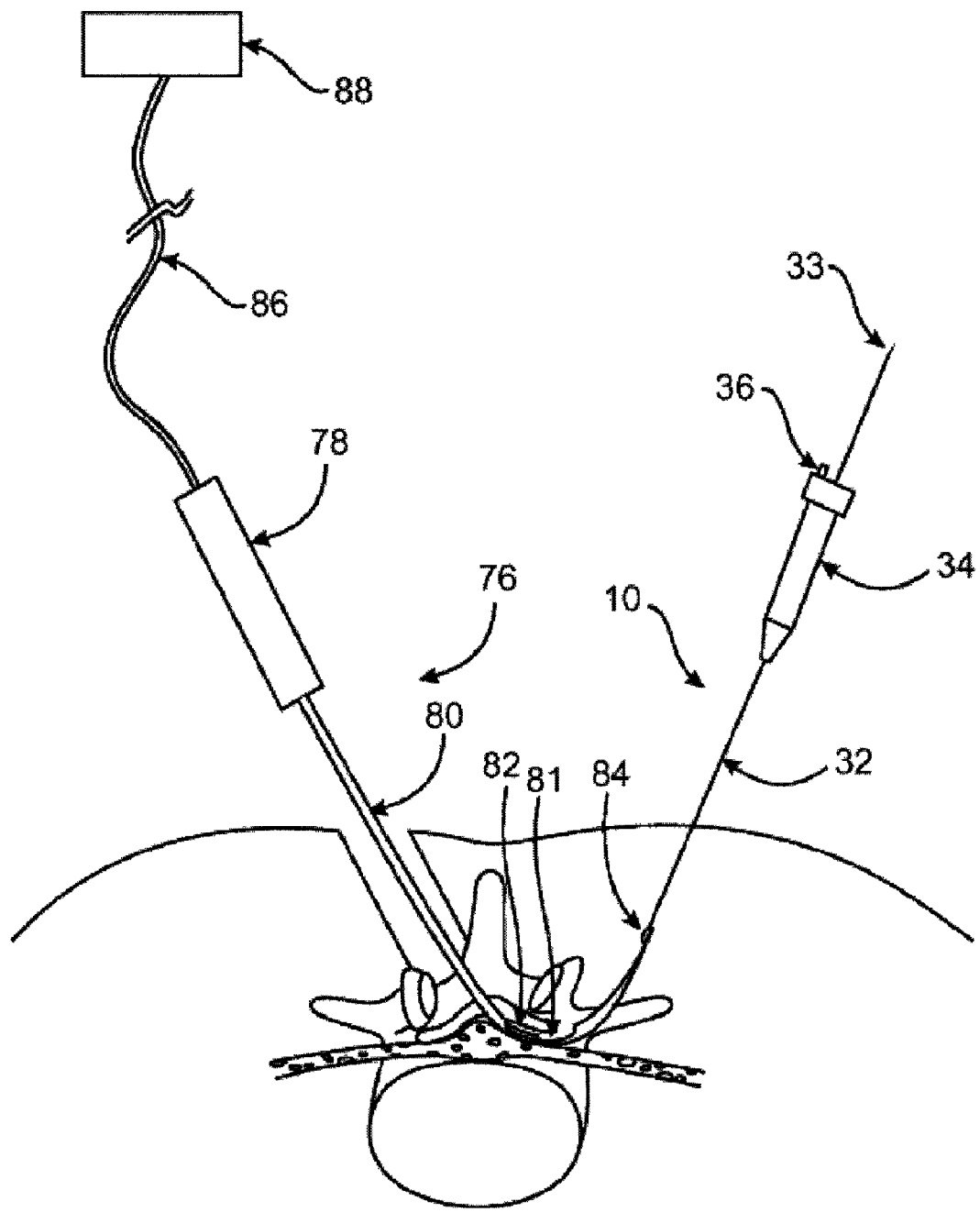
FIG. 7 is a cross-sectional view of a patient's back and spine and a side view of an ultrasound device and guidewire system.

Referring to FIG. 7, in another alternative embodiment, an ultrasound tissue modification device 76 may be advanced into position in a patient's back using guidewire system 10. In one embodiment, for example, ultrasound device 76 may include a proximal handle 78, a hollow shaft 80 having a distal window 81, multiple ultrasound wires 82 extending through shaft 80 and into window 81, a guidewire connector 84 coupled with a tapered distal end of shaft 80, an ultrasound generator 88, and a wire 86 coupling handle 78 with generator 88. Handle 78 may include, for example, an ultrasound transducer, horn and/or other ultrasound transmission components. Shaft 80 may be completely rigid, completely flexible, or part rigid/part flexible, according to various embodiments. Ultrasound energy provided by generator 88 may be converted in handle 78 to reciprocating motion of wires 82, and reciprocating wires 82 may be used to cut, chisel or otherwise modify soft and/or hard tissues. Further description of such an embodiment is provided in U.S. patent application Ser. No. 11/461,740, which was previously incorporated by reference. Guidewire connector 84 may comprise one of a number of different connectors, various embodiments of which are described in further detail below.

Figure 8A:
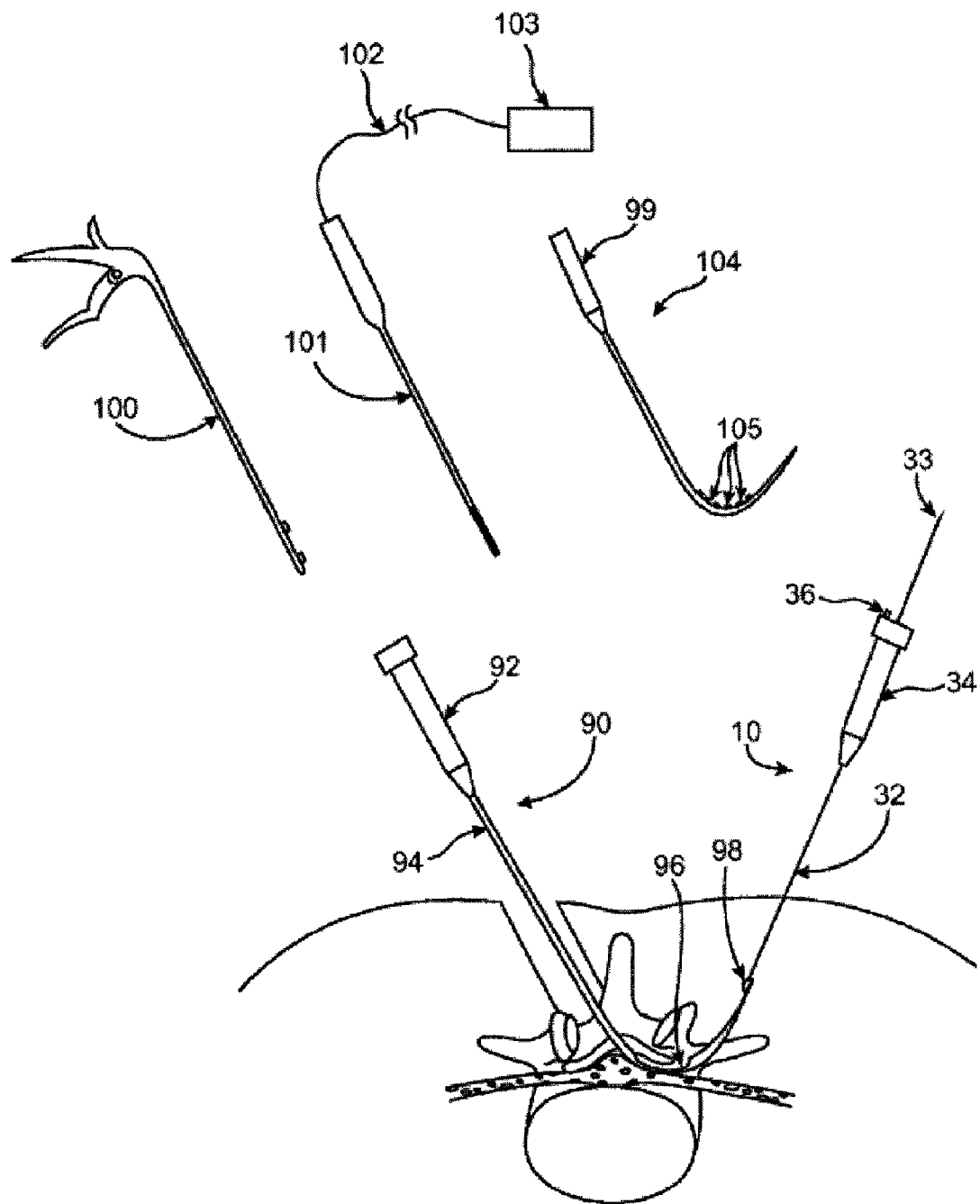
FIG. 8A is a cross-sectional view of a patient's back and spine and a side view of a tissue access device with swappable tissue modification devices and a guidewire system.

In another embodiment, and with reference now to FIG. 8A, guidewire system 10 may be used to pull/advance a tissue access device 90 into place between target and non-target tissues. Tissue access device 90, for example, may include a proximal handle 92, a hollow shaft 94 having a distal curved portion with a distal window 96, and a guidewire connector 98 coupled with a tapered distal end of shaft 94. As with previously described embodiments, shaft 94 may be flexible along its entire length, rigid along its entire length, or rigid in part and flexible in part, and may be made of any suitable material or combination of materials. In some embodiments, shaft 94 may also be steerable, such as with one or more pull wires or other steering mechanisms, for example to steer or curve a distal portion of shaft 94.

Once access device 90 is in a desired position, with window 96 facing target tissue (such as ligamentum flavum and/or facet joint bone in the spine) and an atraumatic surface of shaft 94 facing non-target tissue, any of a number of compatible tissue modification devices 100, 101, 104 or other devices may be advanced through access device 90 to perform a tissue modification procedure or other functions. Such devices may be swappable in and out of access device 90 and may be in the form of cartridges, so that various cartridges may be inserted and removed as desired, over the course of a procedure. Examples of several tissue modification devices are shown in FIG. 8A, including a rongeur device 100, an ultrasound device 101 (including wire 102 and ultrasound generator 103), and an abrasive, reciprocating device 104. Further examples of tissue modification and other devices are described below with reference to FIGS. 8B-8M.

In one embodiment, for example, at least a distal portion of each tissue modification device 100, 101, 104 may be flexible, and a proximal portion of each modification device 100, 101, 104 may have a locking feature for locking into proximal handle 92 of access device 90. Thus, a given modification device, such as abrasive device 104, may be advanced into handle 92 and shaft 94, so that abrasive members 105 of device 104 are exposed through window 96 and locking feature 99 of device couples and locks within handle 92. A user may then grasp handles 34 and 92, pull up to urge abrasive members 105 against target tissue, and reciprocate access device 90 and guidewire system 10 back and forth to remove target tissue. The user may then choose to remove abrasive device 104 and insert one of the other devices 100, 101 to further modify target tissues.

In various embodiments, any of a number of tissue modification devices and/or other devices may be provided (for example as cartridges) for used with access device 90. In some embodiments, one or more of such devices may be provided with access device 90 and guidewire device 10 as a system or kit. Any given tissue modification device may act on tissue in a number of different ways, such as by cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting target tissue. Non-tissue-modifying devices or cartridges may additionally or alternatively be provided, such as but not limited to devices for: capturing, storing and/or removing tissue; delivering a material such as bone wax or a pharmacologic agent such as thrombin, NSAID, local anesthetic or opioid; delivering an implant; placing a rivet, staple or similar device for retracting tissue; delivering a tissue dressing; cooling or freezing tissue for analgesia or to change the tissue's modulus of elasticity to facilitate tissue modification; visualizing tissue; and/or diagnosing, such as by using ultrasound, MRI, reflectance spectroscopy or the like. In given method, system or kit, any combination of tissue modification and/or non-tissue-modifying devices may be used with access device 90.

Although the example provided above describes the use of any of a number of tissue modification devices and/or other devices for used with an access device 90, these devices (also referred to as surgical devices) may also be used without an access device 90. For example, as illustrated in FIGS. 5 and 6, a surgical device may be coupled to a guidewire and inserted (via a percuateous or open route) into a patient using the guidewire without the use of an additional access device 90. In some variations, particularly those in which the internal spacing between target and non-target tissues is narrow or small, it may be better to use such devices without the additional thickness of an access device 90. Thus, in some variations, the surgical devices used as part of the guidewire systems have a relatively flat and flexible distal end region.

Figure 8B:
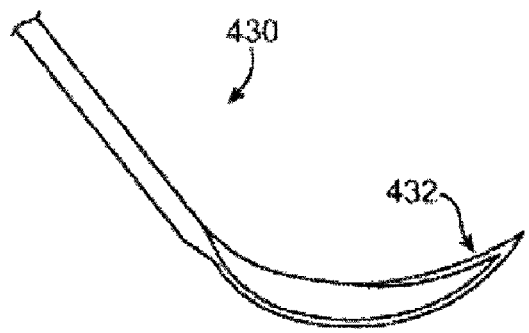
FIGS. 8B-8M are side/perspective views of distal portions of a number of different devices which may be placed through/used with a tissue access device such as that shown in FIG. 8A.
Figure 8C:
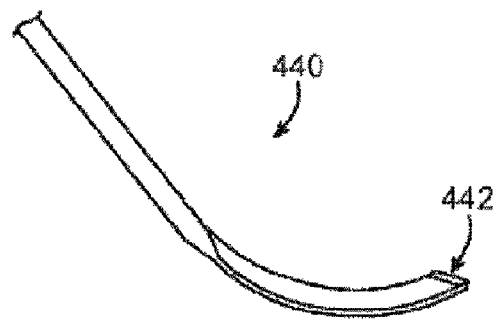
Figure 8D:
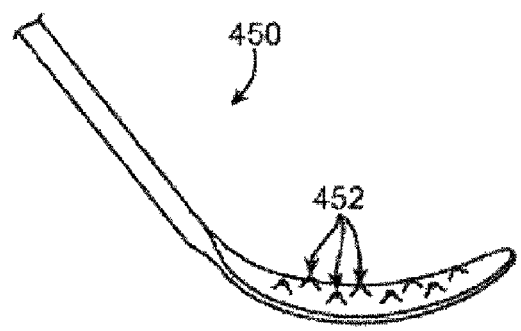
Figure 8E:
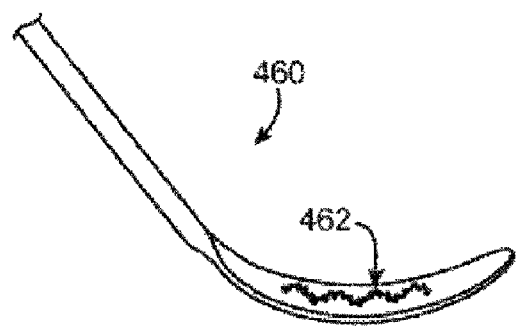
Figure 8F:
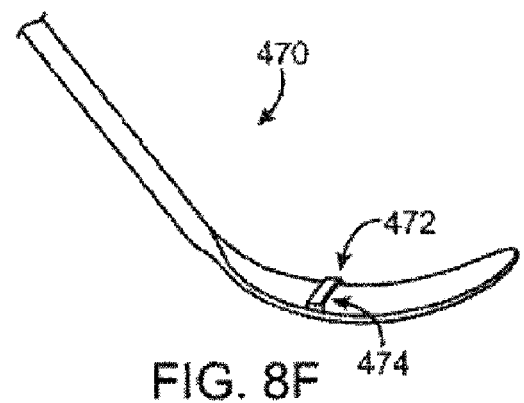
Figure 8G:
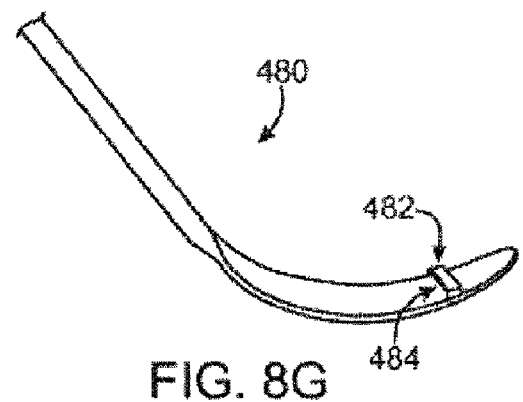
Figure 8H:
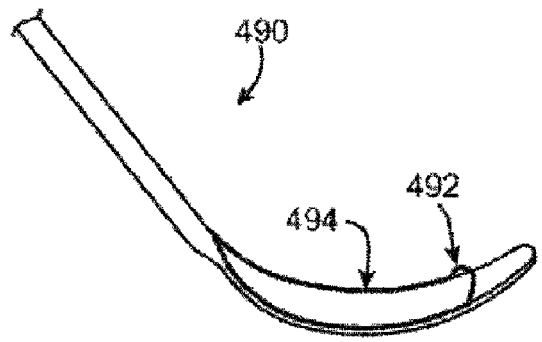

With reference now to FIGS. 8B-8M, distal portions of a number of exemplary embodiments of surgical devices (which may be in cartridge form in some embodiments and may be used with access device 90) are shown. FIG. 8B shows a device 430 including a sharpened, pointed, double-beveled distal tip 432. Tip 432 may be advanced across window 96 of access device 90 to cut tissue. FIG. 8C shows a device 440 including a diagonal-edge distal cutting tip 442, which may be used in a similar manner to cut tissue. FIG. 8D shows a device 450 including multiple volcano-shaped abrasive members 452. In alternative embodiments of abrasive devices, any suitable abrasive members or surfaces may be used. FIG. 8E, for example, shows a device 460 including a portion of a Gigli saw 462 attached to the device's upper surface, such as by welding. Any of a number of blades may alternatively be attached to a device, such as in the device 470 shown in FIG. 8F. Here, device 470 includes a proximally placed blade 472 having a cutting edge 474, which may be advanced across window 96 to cut tissue. FIG. 8G shows an alternative embodiment in which a device 480 includes a distally placed blade 482 with a cutting edge 484 that may be drawn back/retracted across window 96 to cut tissue. In another tissue-modifying embodiment, FIG. 8H shows a device 490 including a radiofrequency (RF) loop electrode 492 for cutting tissue and extending proximally via two insulated wires 494.

Figure 8I:
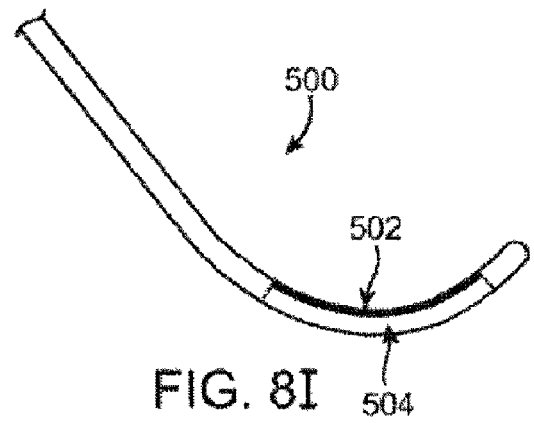
Figure 8J:
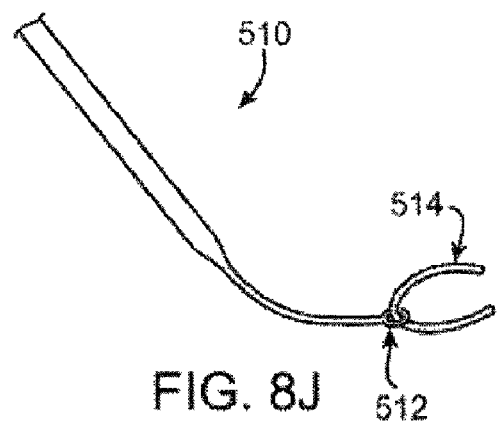
Figure 8K:
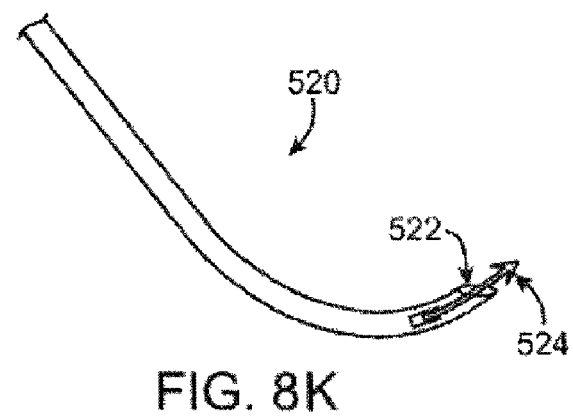

With reference to FIG. 8I, in an alternative embodiment, a device 500 may include a side-facing aperture 502 and a chamber 504. Device 500 may be advanced into access device 90 to align aperture 502 with window 96 and may then be used to collect tissue in chamber 504. Device 500 may then be removed (in some variations through access device 90) to remove the tissue from the patient. This may be repeated as many times as desired, to remove cut tissue from the patient. FIG. 8J shows a device 510 having a clamp 512 for delivering an implant 514. Implant 514, for example, may be a posterior decompression implant such as the "X-STOP" Interspinous Process Decompression™ devices offered by St. Francis Medical Technologies, Inc. (Alameda, Calif.), a foraminal implant such as that described in PCT Patent Application Pub. No. WO 2006/042206A2, or any other suitable implant for the spine or other area of the body. FIG. 8K shows an embodiment of a device 520 used for delivering a rivet (or "tissue anchor") 524 through a distal aperture 522. In one embodiment, for example, tissue anchor 524 may be anchored to bone and used to retract ligamentum flavum tissue to increase the area of a space in the spine. Such a device is described in more detail, for example in U.S. patent application Ser. No. 11/250,332, entitled "Devices and Methods for Selective Surgical Removal of Tissue," and filed Oct. 15, 2004, the full disclosure of which is hereby incorporated by reference.

Figure 8L:
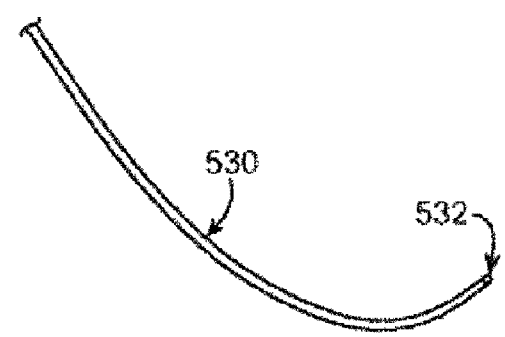
Figure 8M:
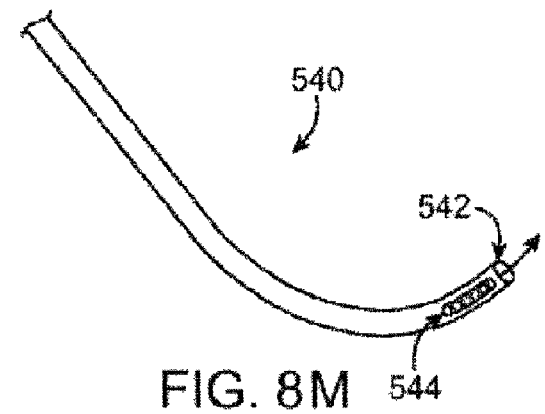

In another embodiment, and with reference to FIG. 8L, a visualization device 530 having a visualization element 532 may be used with access device 90. Such a device may include, for example, an endoscope, fiber optics, a camera coupled with a catheter or the like. In other embodiments, ultrasound, MRI, spectroscopy or other diagnostic or visualization devices may be used. FIG. 8M shows an alternative embodiment of a device 540, which includes a distal aperture 542 through which a tissue dressing 544 may be delivered. Tissue dressing 544, for example, may include one or more fabrics, gel foam or the like. In some embodiments, one or more pharmacologic agents may be delivered through device 540. Alternatively or additionally, irrigation and/or suction may be provided through device 540. As should be apparent from the foregoing description, any suitable device, cartridge or combination of devices/cartridges may be used either with access device 90 or without a separate access device. These devices may be positioned and/or manipulated (e.g., urged against a target tissue) using the guidewire systems described herein. In addition, multiple devices may be exchanged during a procedure using the same guidewire.

Figure 9:
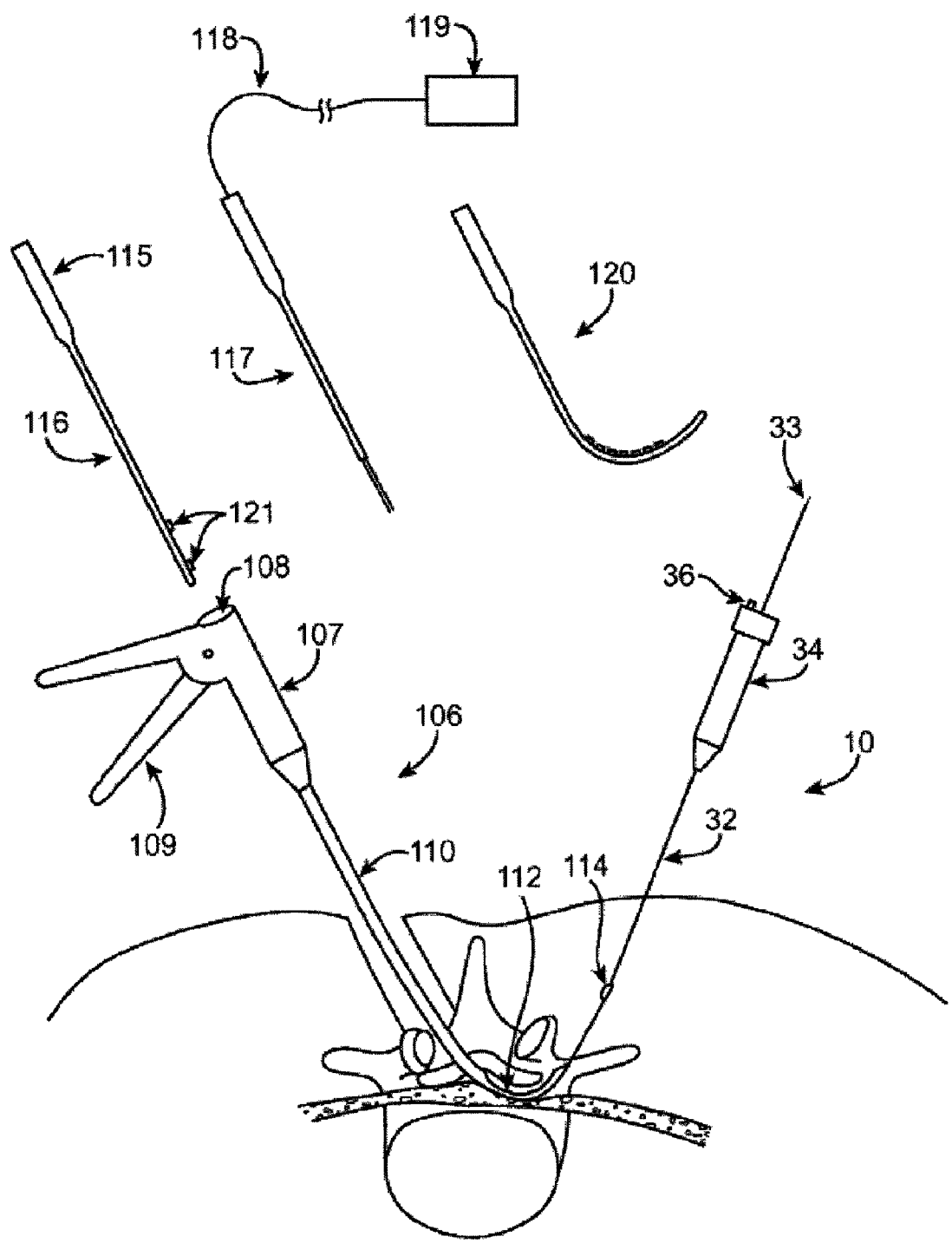
FIG. 9 is a cross-sectional view of a patient's back and spine and a side view of a tissue access device with swappable tissue modification devices and a guidewire system.

Referring now to FIG. 9, another embodiment of a tissue access device 106, which may be advanced to a position in a patient's back using guidewire system 10, is shown. Tissue access device 106 may include, for example, a proximal handle 107 having a hollow bore 108 and an actuator 109, a hollow shaft 110 extending from proximal handle 107 and having a distal curved portion and a distal window 112, and a guidewire coupling member 114 coupled with a tapered distal end of shaft 110. As with the previously described embodiment, a number of different tissue modification devices 116, 117, 120 may be inserted and removed from access device 106 to perform a tissue modification procedure, such as a rongeur 116, an ultrasound device 117 (including a wire 118 and generator 119), and an abrasive device 120. In the embodiment of FIG. 9, however, handle 107 includes the additional feature of actuator 109, which may be used to activate one or more tissue modifying members of various tissue modification devices. For example, rongeur 116 may be advanced into hollow bore 108 and shaft 110, to position blades 121 of rongeur 116 so as to be exposed through window 112, and to lock a locking member 115 of rongeur 116 within handle 107. Actuator 109 may then be moved back and forth (by squeezing and releasing, in the embodiment shown) to move one or both blades 121 back and forth to cut target tissue. Optionally, rongeur 116 may then be removed from access device 106 and a different modification device 117, 120 inserted to further modify target tissue. Actuator 109 may be used with some modification devices and not others. Again, in some embodiments, access device 106, guidewire system 10 and one or more modification devices 116, 117, 120 may be provided as a system or kit.

Figure 10:
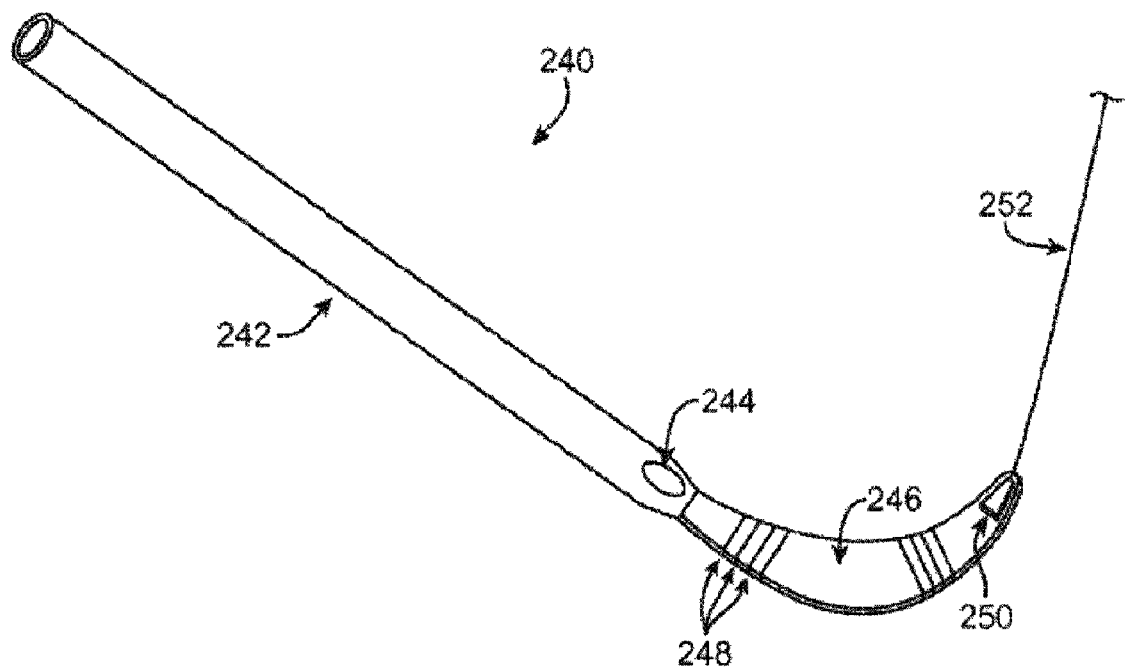
FIG. 10 is a perspective view of a tissue access device coupled with a guidewire.

With reference now to FIG. 10, a perspective view of one embodiment of a tissue access device 240 is shown. Device 240 may include an elongate, hollow shaft 242 having a distal aperture 244, a distal extension 246 (or "platform" or "tissue shield") extending beyond shaft 242, and a guidewire coupling member 250 attached to distal extension 246 for coupling with a guidewire 252. Both shaft 242 and distal extension 246 may be either rigid or flexible, in various embodiments. In the embodiment shown, distal extension 246 includes multiple flexibility slits 248 to enhance flexibility of that portion of device 240. Shaft 242, distal extension 246 and guidewire coupling member 250 may be made of any suitable material (or materials), and may be made from one piece of material as a single extrusion or from separate pieces attached together, in alternative embodiments. Suitable materials include, for example, metals, polymers, ceramics, or composites thereof. Suitable metals may include, but are not limited to, stainless steel (303, 304, 316, 316L), nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France). Suitable polymers include, but are not limited to, nylon, polyester, Dacron™, polyethylene, acetal, Delrin™ (DuPont, Wilmington, Del.), polycarbonate, nylon, polyetheretherketone (PEEK), and polyetherketoneketone (PEKK). Ceramics may include, but are not limited to, aluminas, zirconias, and carbides.

In addition to various materials, tissue access device 240 may have any desired combination of dimensions and shapes. In some embodiments, for example, shaft 242 and distal extension 246 have different cross-sectional shapes, while in other embodiments, they may have the same cross-sectional shape. Some embodiments may include additional features, such as a mechanism for changing distal extension 246 from a straight configuration to a curved configuration (such as with one or more pull wires).

Any of a number of different surgical/tissue modification devices, such as but not limited to those described in reference to FIGS. 8 and 9, may be used in conjunction with tissue access device 240. Such a tissue modification device may be used, for example, by passing the device through shaft 242, such that a portion of the device extends out of aperture 244 to perform a procedure, while distal extension 246 protects non-target tissue from harm. In various embodiments, multiple surgical devices may be passed through and used with tissue access device 240, either serially or simultaneously, depending on the configuration of access device 240 and the constraints of the operating field and anatomy.

Figure 11:
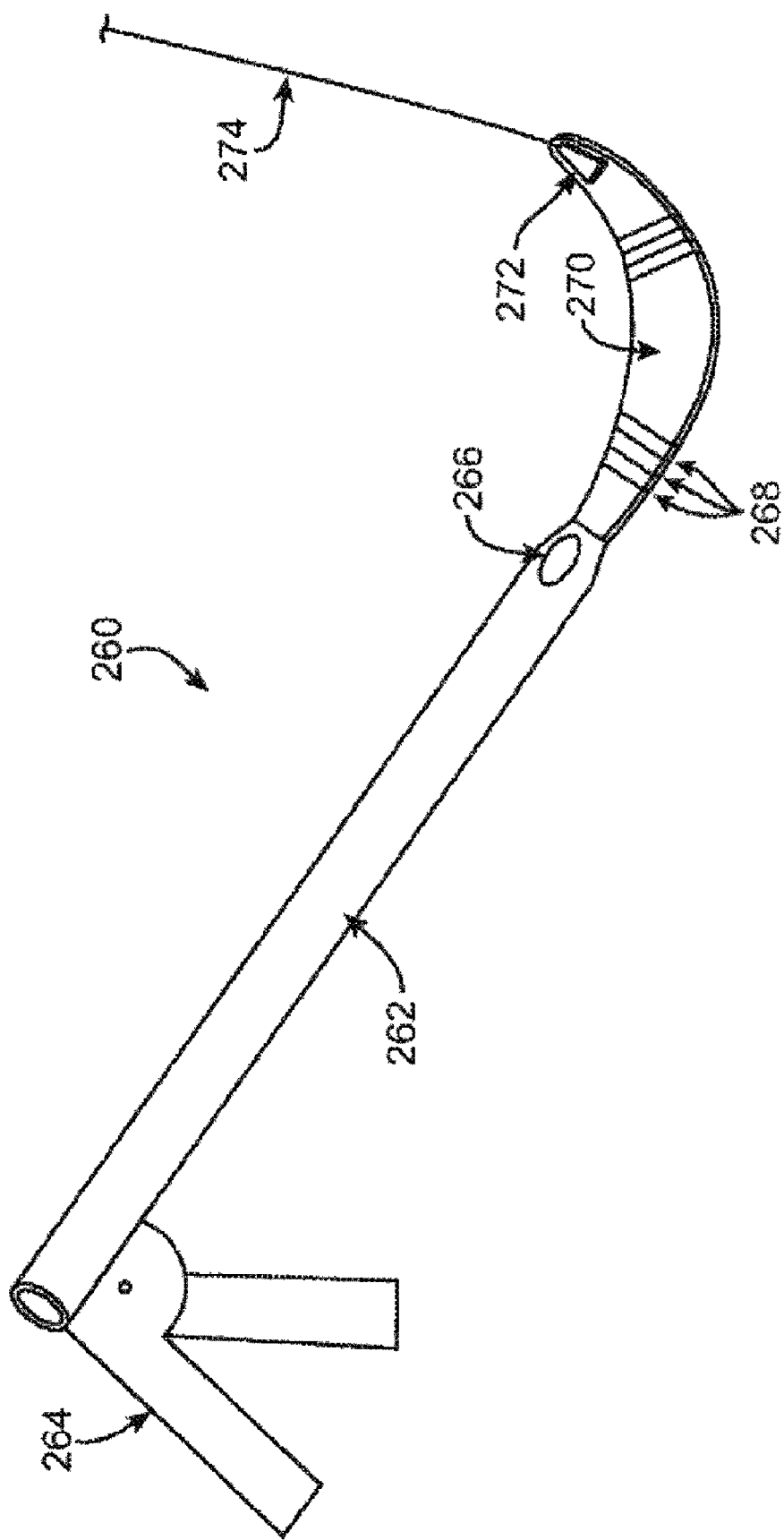
FIG. 11 is a perspective view of a tissue access device coupled with a guidewire.

Referring to FIG. 11, in another embodiment, a tissue access device 260 includes an elongate, hollow shaft 262, a handle 264, a distal aperture 266, and a distal extension 270 having flexibility slits 268 and coupled with a guidewire coupling member 272, which may be coupled with a guidewire 274. This embodiment of tissue access device 260 is similar to the one described immediately above but includes the additional feature of handle 264, which in some embodiments may be used to actuate one or more surgical/tissue modification devices passed through access device 260.

Figure 12:
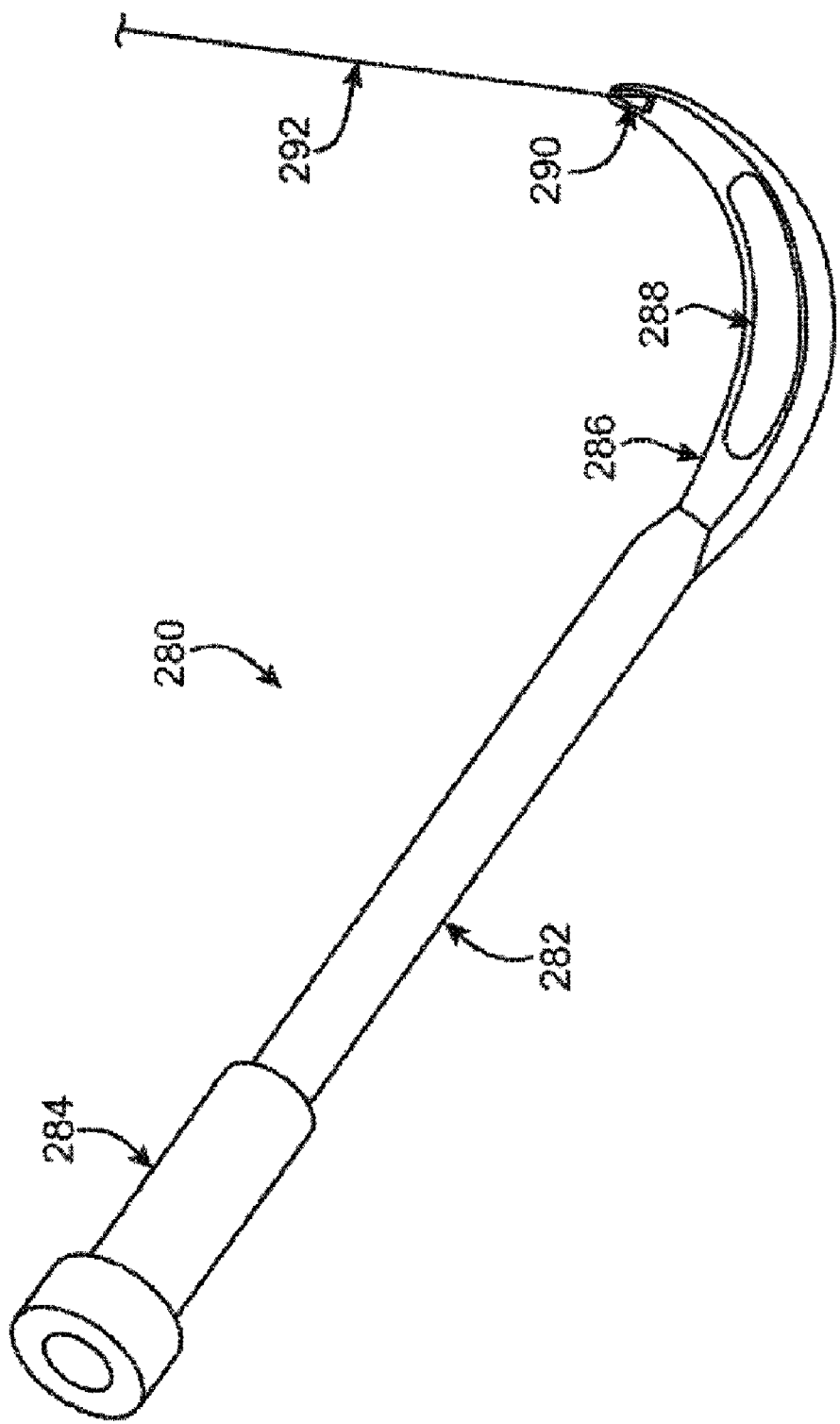
FIG. 12 is a perspective view of a tissue access device coupled with a guidewire.

FIG. 12 depicts another alternative embodiment of a tissue access device 280, including a proximal shaft portion 282, a distal shaft portion 286, and a handle 284. Distal shaft portion 286 includes a window 288, through which a portion of a surgical/tissue modification device may be exposed to perform a procedure, and a guidewire coupling member 290, which may be coupled with a guidewire 292. As with the previously described embodiments, any of a number of surgical devices may be passed through and used with tissue access device 280, according to various embodiments. Tissue modifying portions of such devices may be exposed through or may even extend out of window 288 to perform any of a number of procedures, while distal shaft portion 286 otherwise protects non-target tissue from damage. In various embodiments, shaft portions 282, 286 may both be flexible, both be rigid, or one may be flexible and the other rigid. In one embodiment, for example, shaft 282, 286 may comprise a flexible catheter, while in an alternative embodiment, shaft 282, 286 may comprise a rigid, probe-like structure.

Any of the embodiments described in FIGS. 10-12 may further optionally include one or more external support devices, which removably attach to shaft 242, 262, 282 and one or more stabilizing structures outside the patient, such as a retractor, bed rail, or the like. Such support devices, such as detachable support arms, may be provided with a tissue access device 240, 260, 280 as part of a system or kit and may be used to help support/stabilize the access device during use.

Coupling Members

As mentioned, in general, a coupling member on (or near) the proximal end of a guidewire mates with the coupling member on (or near) the distal end of a surgical device. The coupling members may be complimentary; for example, the device coupling member on the guidewire may be received by a guidewire coupling member on the device. Coupling members may be configured to lock securely together. Coupling members may be configured so that reasonably high pulling forces (e.g., pulling on the distal end of the guidewire and/or the proximal end of the surgical device) can be handled without breaking or de-coupling the coupling members. In some variations the coupling members are configured to lock together permanently or temporarily. For example, a coupling member may be configured to secure together until adequate force is applied to separate them.

With reference now to FIGS. 13A-13D, one embodiment of a surgical device distal portion 138 with a guidewire coupling member 130 is shown in conjunction with a shaped guidewire 134. Guidewire coupling member 130 may generally include a slit 131 and a bore 132. Guidewire 134 may include a device coupling member formed as a shaped member 136 at one end, which is shown as a ball-shaped member 136 but may have any of a number of suitable shapes in alternative embodiments. Generally, guidewire 134 and shaped member 136 may be made of any suitable material, such as but not limited to any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France). Suitable polymers include but are not limited to nylon, polyester, Dacron™, polyethylene, acetal, Delrin™ (DuPont, Wilmington, Del.), polycarbonate, nylon, polyetheretherketone (PEEK), and polyetherketoneketone (PEKK). Ceramics may include but are not limited to aluminas, zirconias, and carbides. Shaped member 136 may be formed by attaching a separate member to one end of guidewire 134, such as by welding, or may be formed out of the guidewire material itself.

Figure 13A:
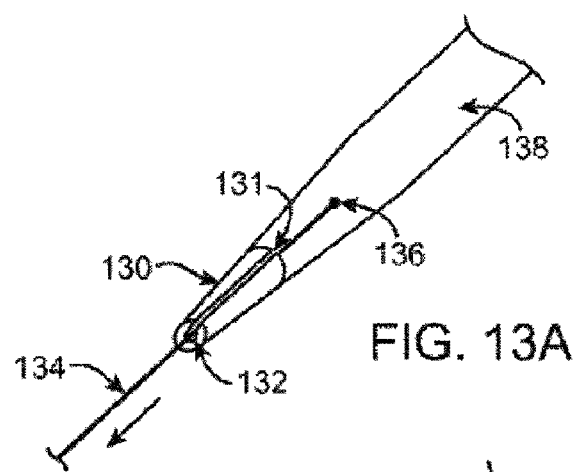
FIGS. 13A and 13C are perspective views.
Figure 13C:
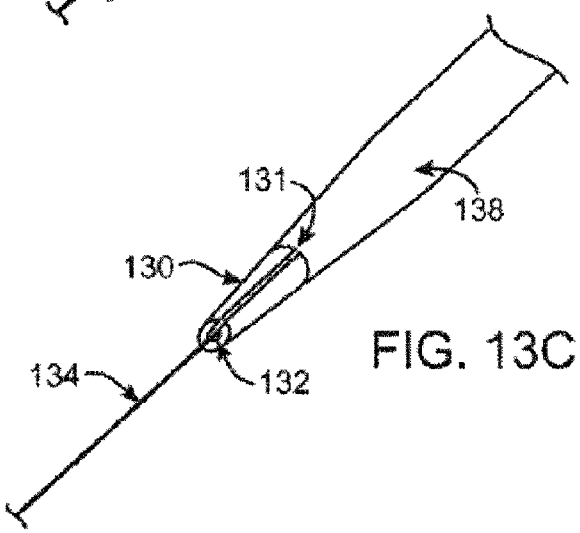
Figure 13B:
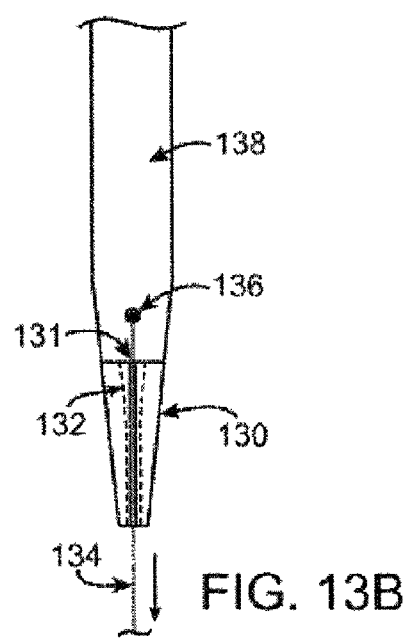
FIGS. 13B and 13D are top views, of a distal end of a tissue modification device with guidewire coupling member and a shaped guidewire.
Figure 13D:
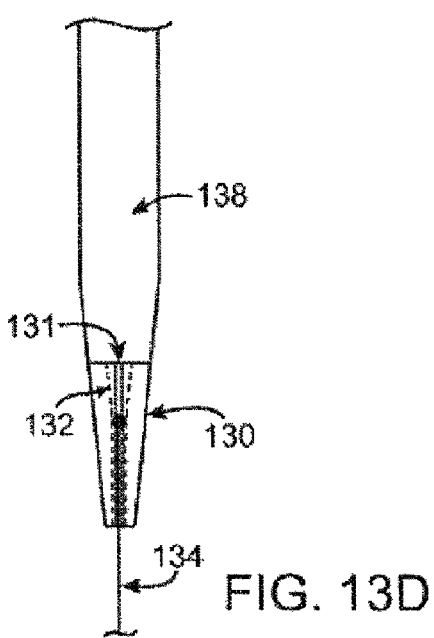

In the embodiment shown, guidewire 134 may be coupled with coupling member 130 by first placing guidewire 134 through slit 131 into bore 132, as shown in perspective view FIG. 13A and top view FIG. 13C. Guidewire 134 may then be pulled through bore 132 (solid-tipped arrows in FIGS. 13A and 13C), to pull shaped member 136 into bore 132, as shown in perspective view FIG. 13B and top view FIG. 13D. As visible in FIGS. 13B and 13D, bore 132 may be tapered, so that shaped member 136 may enter bore 132 but may only travel partway through before reaching a diameter of bore 132 through which it cannot pass. In an alternative embodiment, bore 132 may include a hard stop rather than a taper. In any case, shaped member 136 may be pulled into bore 132 to cause it to lodge there, and additional pulling or tensioning force may be applied to guidewire 134 without risk of pulling shaped member 136 farther through bore 132. Guidewire 134 may thus be used to pull surgical device 138 through tissue and into a desired position for performing a procedure, and may further be used to apply tensioning/pulling force to surgical device 138 to help urge a tissue modifying portion of device 138 against target tissues.

As with many of the embodiments described previously and hereafter, guidewire coupling member 130 may be either attached to or formed as an integral part of surgical device distal portion 138, according to various embodiments. Coupling member 130 may be made of any suitable material, as has been mentioned previously, and may have any desired dimensions and any of a number of different configurations, some of which are described in further detail below. In various embodiments, coupling member 130 may be attached to an extreme distal end of surgical device 138 or may be positioned at or near the extreme distal end. Although coupling member 130 is typically attached to or extending from a top or upper surface of surgical device 138, in some embodiments it may alternatively be positioned on a bottom/lower surface or other surface.

In another embodiment, and with reference now to FIGS. 14A and 14B, a guidewire coupling member 140 including a slit 142 with one or more curves 144 and a bore 143 may be attached to a surgical device distal portion 148. A guidewire 146 having a cylindrical shaped member 147 at one end may be placed through slit 142 into bore 143 and pulled distally (solid-tipped arrow), as shown in FIG. 14A. When shaped member 147 is pulled into bore 143, it is stopped by, and cannot pass through, curves 144, thus allowing guidewire 146 to be used to pull device 148 into place between target and non-target tissues and apply tensioning force.

Referring to FIGS. 15A-15F, an alternative embodiment of a guidewire coupling member 150 is shown with a shaped guidewire 158. Guidewire coupling member 150 may include a transverse slit 152, an axial channel 154 and a transverse bore 156. FIG. 15E shows a front perspective view of coupling member 150, where member 150 would be mounted on a surgical device such that a front side 151 would face distally and a back side 153 would face proximally. FIG. 15F shows a rear perspective view of coupling member 150 with back side 153 and front side 151.

FIG. 15A is a rear/left perspective view, and FIG. 15B is a top view, both showing guidewire 158 with a ball-shaped member 159 being placed through transverse slit 152 into channel 154. Channel 154 is generally an open portion within coupling member 150, having a diameter similar to or the same as that of slit 152, to allow guidewire 158 to be rotated through coupling member 150, as depicted by the solid-tipped, curved arrow in FIGS. 15A and 15B. Bore 159 is sized to allow ball-shaped member 159 (forming the device coupling member of the guidewire) to travel into it to rest within coupling member 150, as shown in FIGS. 15C and 15D. Ball-shaped member 159 is sized such that, when shaped guidewire 158 is rotated into position within coupling member 150, it cannot travel through channel 154, and is thus trapped within bore 156. Guidewire 158 may thus be pulled, to pull a device into position and/or to apply tension to the device, without guidewire 158 pulling out of coupling member 150. Guidewire 158 may be disengaged from coupling member 150 by rotating guidewire 158, coupling member 150 or both, to release shaped member 159 from bore 156. In one embodiment, coupling member 150 may be attached to a top surface of a distal portion of a surgical device, such as by welding, adhesive or other attachment means.

An alternative embodiment of a guidewire coupling member 160 is depicted in FIGS. 16A-16E. In this embodiment, guidewire coupling member 160 includes a channel 162, a central bore 164 and a side channel, as shown in perspective view FIG. 16A, top view FIG. 16B and side view FIG. 16C. Channel 162 is generally shaped and sized to allow a shaped member 169 of a guidewire 168 to pass longitudinally therethrough. Central bore 164 is shaped and sized to allow shaped member 169 to rotate within bore 164. Side channel 166 is shaped and sized to allow guidewire 168 to pass therethrough when guidewire 168 is rotated about an axis through shaped member 169. An angle 165 formed by channel 162 and an opposite end of side channel 166 may be any desired angle, in various embodiments. For example, the angle in the embodiment shown (best seen in FIGS. 16B, 16D and 16E) is approximately 90 degrees. In alternative embodiments, the angle could instead be less than 90 degrees or greater than 90 degrees. In one embodiment, for example, an angle of about 135 degrees may be used, while in another embodiment, an angle of about 180 degrees may be used.

Figure 16B:
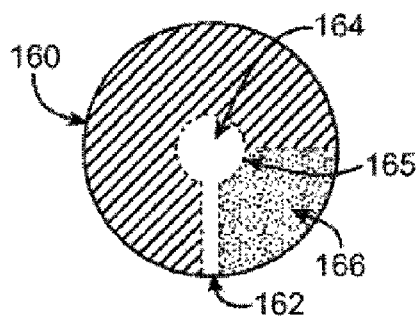
FIGS. 16A-16C are perspective, top and side views, respectively, of a guidewire coupling member.
Figure 16C:
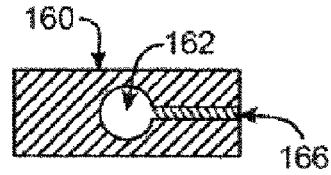
Figure 16D:
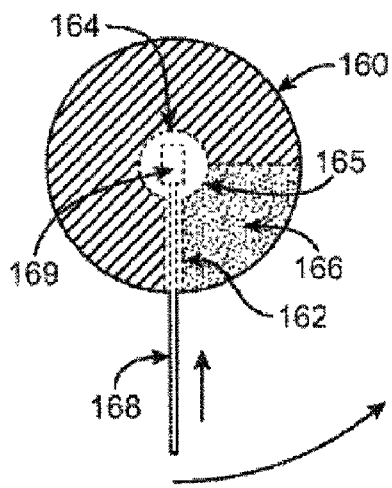
FIGS. 16D and 16E are top views of the guidewire coupling member of FIGS. 16A-16C and a shaped guidewire, demonstrating a method for coupling the coupling member with a shaped guidewire.
Figure 16E:
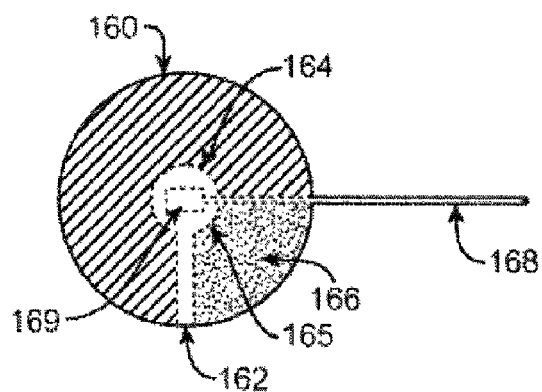
Figure 16A:
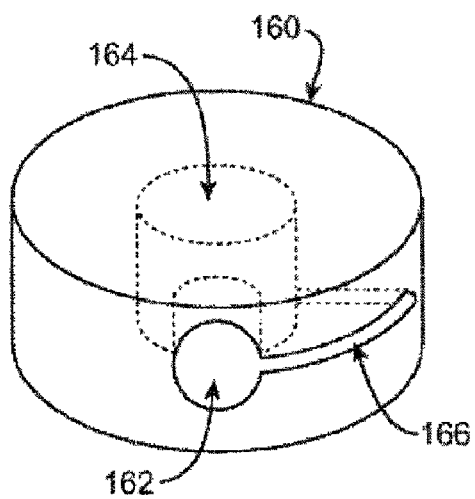

As depicted in FIG. 16D, shaped member 169 of guidewire 168 may be passed through channel 162 and into central bore 164 (hollow-tipped arrow). Guidewire 168 may then be rotated about an axis approximately through shaped member 169 (solid-tipped, curved arrow). When rotated, guidewire 168 passes through side channel 166 to its end, as shown in FIG. 16E. Guidewire 168 may then be pulled, to pull a device attached to coupling member 160 to a desired position in a patient's body, such as between target and non-target tissues. Rotated shaped member 169 is trapped within central bore 164, due to its shape and size, and cannot pass into either side channel 166 or channel 162. To remove guidewire 168 from coupling member 160, guidewire 168 may be rotated back to the position shown in FIG. 16D and withdrawn from coupling member 160 through channel 162.

Figure 17A:
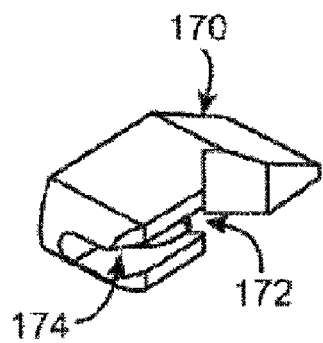
FIGS. 17A and 17B are perspective views of a guidewire coupling member.
Figure 17B:
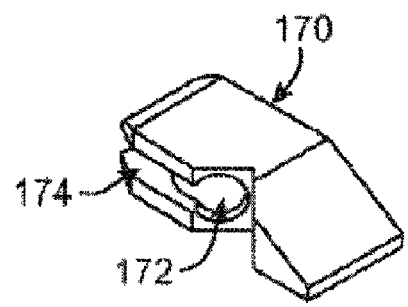
Figure 17C:
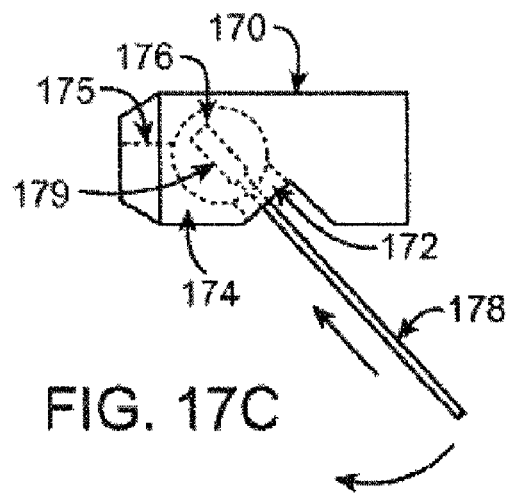
FIGS. 17C and 17D are top views of the guidewire coupling member of FIGS. 17A and 17B and a shaped guidewire, demonstrating a method for coupling the coupling member with the guidewire.
Figure 17D:
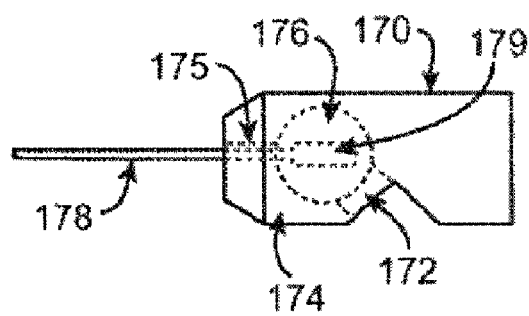

Referring now to FIGS. 17A-17D, another alternative embodiment of a guidewire coupling member 170 is shown. FIGS. 17A and 17B are front perspective and rear perspective views, respectively, in which a channel 172 and a side channel 174 of coupling member 170 may be seen. FIGS. 17C and 17D are top views, showing coupling member 170 with an inserted guidewire 178. As seen in FIG. 17C, guidewire 178 with a shaped distal member 179 may be advanced through channel 172 (hollow-tipped arrow), to position shaped member 179 in a central bore 176 of coupling member 170. Guidewire 178 may then be rotated through side channel 174 about an axis approximately about shaped member 179 (solid-tipped, curved arrow). As shown in FIG. 17D, guidewire 178 may be rotated until it hits an end 175 of side channel 174. Guidewire 178 may then be pulled to pull a device attached to coupling member 170, as shaped member 179 will be trapped within central bore 176, due to its shape and size. When desired, guidewire 178 may be removed from coupling member 170 by rotating guidewire 178 back to the position shown in FIG. 17C and withdrawing it through channel 172. Channel 172 may be located at any desired angle, relative to end 175 of side channel 174. In the embodiment shown, for example, the angle is approximately 135 degrees. As in the embodiment described immediately above, channel 172 is generally shaped and sized to allow shaped member 179 to pass longitudinally therethrough, central bore 176 is shaped and sized to allow shaped member 179 to rotate within bore 176, and side channel 174 is shaped and sized to allow guidewire 178 to pass therethrough when guidewire 178 is rotated.

Turning to FIGS. 18A and 18B, in another alternative embodiment, a guidewire coupling member may include a cam 300 and a stationary portion 306 (only a part of which is shown). Cam may 300 rotate about an axis 302 from an open position (FIG. 18A), which allows a guidewire 304 to pass through, to a closed position (FIG. 18B), which traps guidewire 304 against stationary portion 306. In one embodiment, cam 300 may automatically move from open to closed positions as guidewire 304 is advanced (arrow in FIG. 18A) and may move from closed to open positions as guidewire 304 is retracted. Some embodiments of a coupling member, such as that shown in FIGS. 18A and 18B, may be used with a guidewire 304 that does not have a shaped member on its proximal end. Alternatively, such a coupling member may also be used with a guidewire including a coupling member, such as a shaped region.

FIG. 19 shows an alternative embodiment of a guidewire coupling member, which includes two opposing cams 310 that rotate toward one another (curved arrows) to grip and hold a guidewire 312. As with the previous embodiment, this coupling member may be used, in various embodiments, either with a guidewire having shaped proximal end or an unshaped guidewire 312.

In the variations illustrated in FIGS. 18 and 19 only one coupling member may be used. For example, a guidewire coupling member on the surgical device may couple with the proximal end of the guidewire, even if the guidewire does not include an additional coupling member (e.g., a shaped region or other coupling member).

Referring now to FIGS. 20A-20C, in another embodiment, a guidewire coupling member 320 (shown in top view) may include three movable rollers 322. In an open position, as in FIG. 20A, rollers 322 may be arrayed to allow a guidewire 324 to pass through them. Rollers 322 may be moved, relative to one another (solid-tipped arrows), to partially constrain guidewire 324 (FIG. 20B) or to completely constrain guidewire 324 (FIG. 20C). Rollers 322 may be moved back to the open position (FIG. 20A) to release guidewire 324.

Figure 21C:
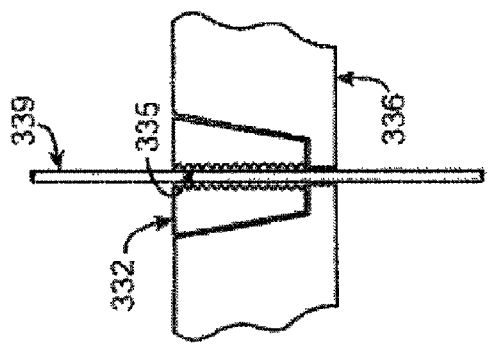
FIGS. 21B and 21C are side cross-sectional views, of a split-cone guidewire coupling member.
Figure 21B:
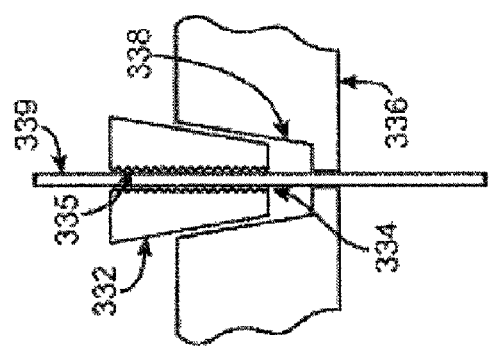
Figure 21A:
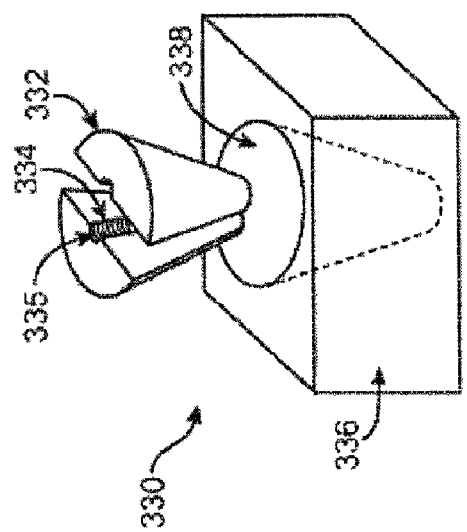
FIG. 21A is a perspective view.

In an alternative embodiment, and referring now to FIGS. 21A-21C, a guidewire coupling member 330 may include a multi-piece cone 332 having a core 334 with a textured inner surface 335, and a stationary portion 336 having a receptacle 338 for receiving cone 332. In an open position, as in FIG. 21B, the two halves of cone 332 are separated and not wedged into receptacle 338, so that a guidewire 339 may be passed through core 334. Cone 332 may be moved to a closed position, as in FIG. 21C, to grip guidewire 339 with textured surface 335 and prevent guidewire 339 from moving further through core 334. In one embodiment, for example, as guidewire 339 moves through core 334, it may generate friction with textured surface 335 and thus pull cone 332 into receptacle. As with several previous embodiments, guidewire 339 may either include a proximal shaped member or may not include such a member, in various embodiments.

Figure 22:
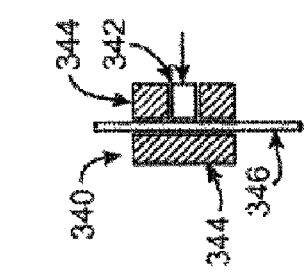
FIG. 22 is a top view of a flat anvil guidewire coupling member.

With reference now to FIG. 22, in another embodiment, a guidewire coupling member 340 may include a flat anvil 342 and one or more stationary portions 344. Anvil may be moved (hollow-tipped arrow) to pinch a guidewire 344 between itself and stationary portion 344.

Figure 23:
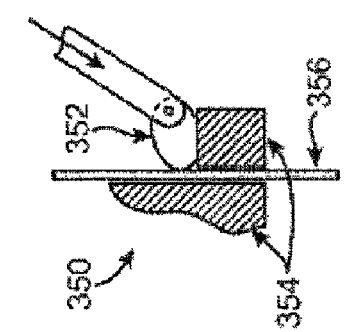
FIG. 23 is a top view of a corner pinch guidewire coupling member.

In an alternative embodiment, shown in FIG. 23, a guidewire coupling member 350 may include a corner-pinch mechanism 352 and one or more stationary portion 354. Mechanism 352 may be advanced (hollow-tipped arrow) to pinch guidewire 356 against stationary member 354 and thus prevent it from moving further through coupling device 350.

Figure 24:
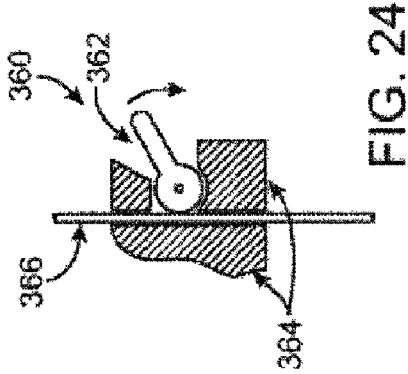
FIG. 24 is a top view of an eccentric cam guidewire coupling member.

Referring to FIG. 24, another embodiment of a guidewire coupling member 360 is shown, which includes an eccentric cam 362 that rotates (hollow-tipped arrow) to pinch a guidewire 366 between itself and a stationary portion 364.

In another embodiment, with reference to FIGS. 27A and 27B, a guidewire coupling member 390 may include multiple spools 392, through which a guidewire 394 may pass, until a shaped member 396 on one end of guidewire 394 gets caught. FIG. 27B shows coupling member 390 attached with an upper surface of a surgical device distal end 391.

Figure 28A:
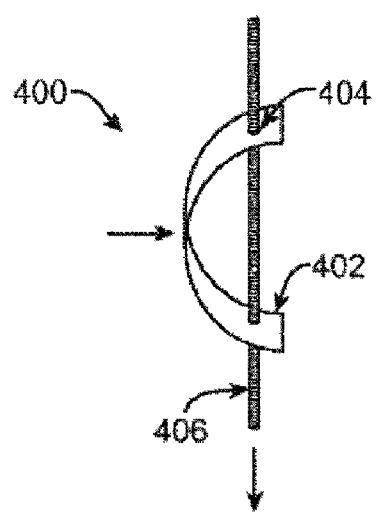
FIGS. 28A and 28B are side views of a semicircular ribbon guidewire coupling member with textured guidewire.
Figure 28B:
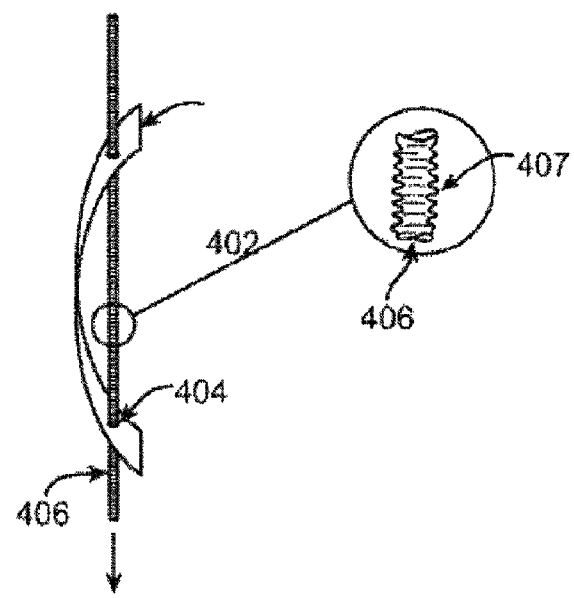

In yet another embodiment, and with reference now to FIGS. 28A and 28B, a guidewire coupling member 400 may include a semi-circular ribbon 402 having two apertures 404. With this embodiment of coupling member 400 (as well as other embodiment described herein), a textured guidewire 406 may be used. As textured guidewire 406 passes through apertures 404, friction caused by the textured surface 407 causes ribbon 402 to flatten (FIG. 28B), thus trapping guidewire 406 in apertures 404. Ribbon 402 may be made of metal or any other suitable material, examples of which have been listed previously.

Figure 29:
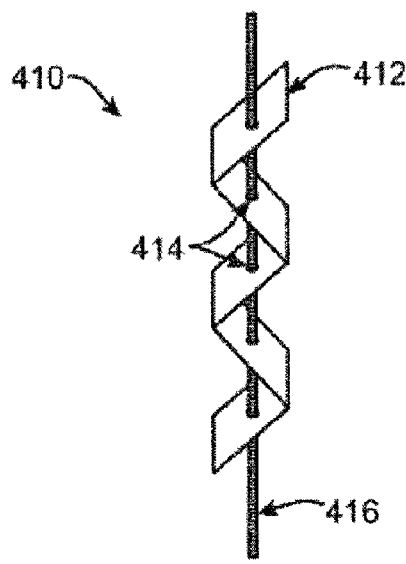
FIG. 29 is a side view of a folded ribbon guidewire coupling member with textured guidewire.

Referring to FIG. 29, another alternative embodiment is shown, in which a guidewire coupling member 410 includes a folded ribbon 412 having multiple apertures 414. Ribbon 412 may flatten as a textured guidewire 416 passes through it, thus causing apertures to trap guidewire 416.

Figure 30:
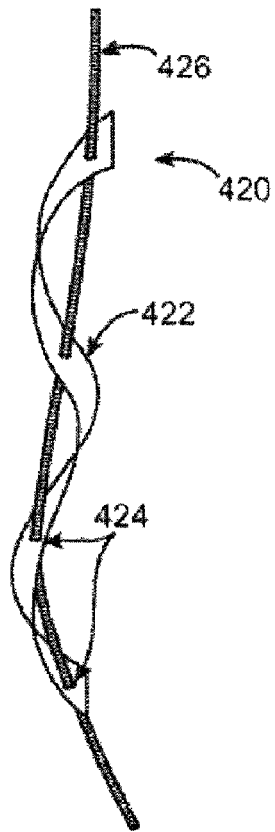
FIG. 30 is a side view of a ribbon guidewire coupling member.

Another embodiment of a guidewire coupling member 420 is shown in FIG. 30. In this embodiment, coupling member 420 includes a curved ribbon 422 with multiple apertures 424. Ribbon 422 may flatten to constrain a guidewire 426 in apertures 424, as with the previously described embodiments. Some embodiments of such ribbon-shaped coupling members 400, 410, 420 may function with a non-textured guidewire as well as, or in place of, a textured guidewire.

Figure 31:
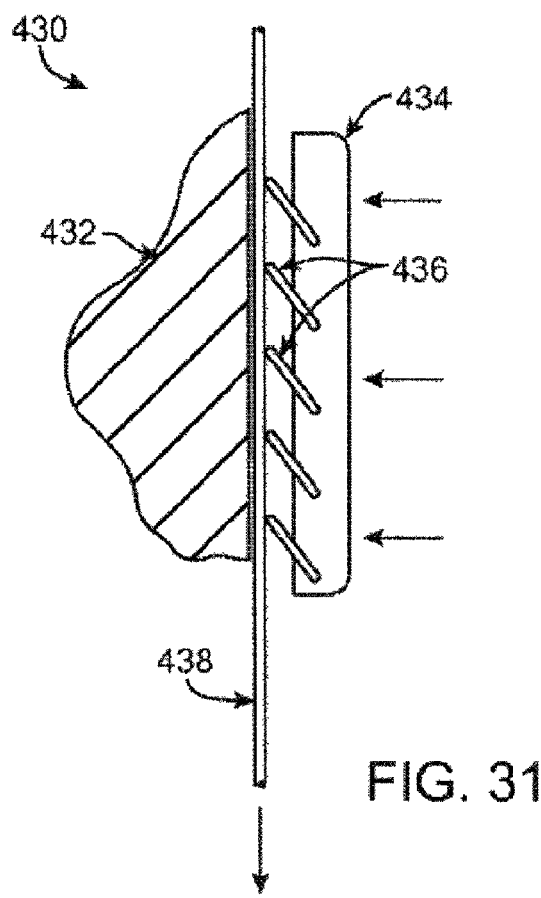
FIG. 31 is a side view of a multi-point guidewire coupling member.

Referring to FIG. 31, in another embodiment, a guidewire coupling member 430 for removably coupling with a guidewire 438 may include a stationary portion 432 and a movable portion 434. Movable portion 434 may include multiple contact members 436 or locking edges, configured to hold guidewire 438 when movable portion 434 is pushed against it (hollow-tipped arrows). Movable portion 434 may be moved using any suitable technique or means in various embodiments. Contact members 436 generally press guidewire 438 against stationary portion 432 such that it will not move through coupling member 430 when pulled (solid-tipped arrow), thus allowing a device coupled with coupling member 430 to be pulled using guidewire 438.

Figure 32:
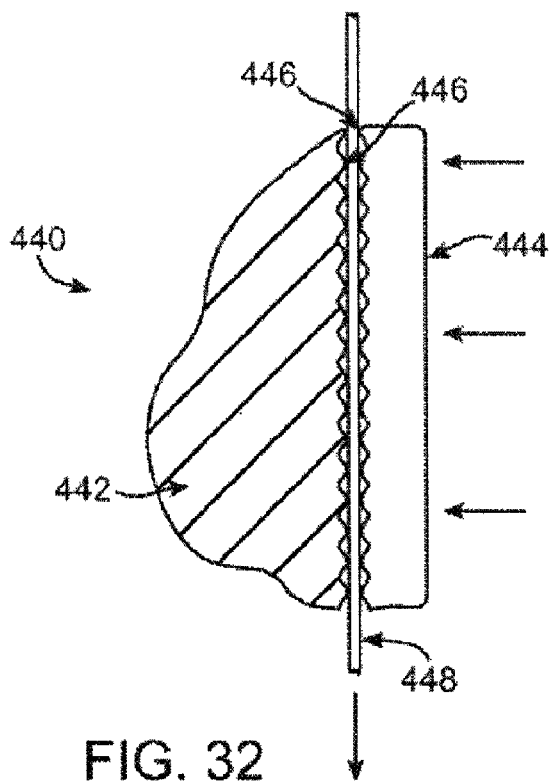
FIG. 32 is a side view of a rough-surface guidewire coupling member.

In another embodiment, and with reference now to FIG. 32, a guidewire coupling member 440 may include a stationary portion 442 and a movable portion 444, each of which has a roughened surface 446 facing one another. Movable portion 444 may be moved toward stationary portion 442 (hollow-tipped arrows) to trap guidewire 446 in between, thus preventing guidewire 446 from moving through coupling member 440 and thus allowing a device coupled with coupling member 440 to be pulled via guidewire 448.

Turning to FIGS. 33A-33D, several alternative embodiments of a guidewire for use with various embodiments of a guidewire coupling member and guidewire system are shown. In some embodiments of a guidewire system, any of a number of currently available guidewires may be used. In other embodiments, a textured guidewire without a shaped member on either end may be used. Each of the embodiments shown in FIGS. 33A-33D, by contrast, has some kind of shaped member on a proximal end of the guidewire for coupling with a guidewire coupling member and some kind of sharpened or otherwise shaped distal tip for facilitating passage of the guidewire through tissue.

In various embodiments, guidewires may comprise a solid wire, a braided wire, a core with an outer covering or the like, and may be made of any suitable material. For example, in one embodiment, a guidewire may be made of Nitinol. In various alternative embodiments, guidewires may be made from any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France). In some embodiments, materials for guidewires or for portions or coatings of guidewires may be chosen for their electrically conductive or thermally resistive properties. Suitable polymers include but are not limited to nylon, polyester, Dacron™, polyethylene, acetal, Delrin™ (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides.

Figure 33A:
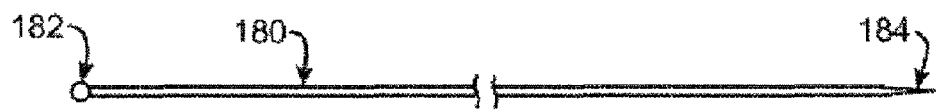
FIGS. 33A-33D are side views of proximal and distal ends of various guidewires.
Figure 33B:
Figure 33C:
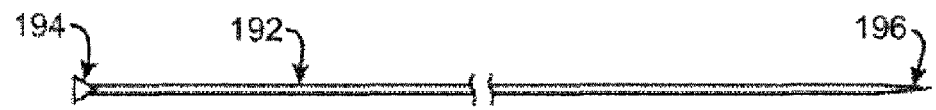
Figure 33D:

In the embodiment shown in FIG. 33A, the guidewire 180 includes a device coupling member that is configured as a ball-like shaped member 182 at the proximal end and a pointed distal tip 184. As with all the following exemplary embodiments, shaped member 182 may be either a separate piece attached to guidewire 180 by welding or other means or may be a proximal end of guidewire 180, formed into shaped member 182. FIG. 33B shows a guidewire 186 with a cylindrical shaped member 188 and a beveled distal tip 190. FIG. 33C shows a guidewire 192 with a pyramidal shaped member 194 and a double-beveled distal tip 196. FIG. 33D shows a guidewire 198 with a cubic shaped member 200 and a threaded distal tip 202. In other variations (e.g., refer to FIGS. 25A-25B) the proximal end of the guidewire may include a hook for coupling with a guidewire couple.

In alternative embodiments, any of the shaped members 182, 188, 194, 200 may be combined with any of the distal tips 184, 190, 196, 202. In yet other alternative embodiments, the shaped members and/or distal tips may have other shapes and/or sizes. Thus, the embodiments shown in FIGS. 33A-33D are provided primarily for exemplary purposes.

Figure 34A:
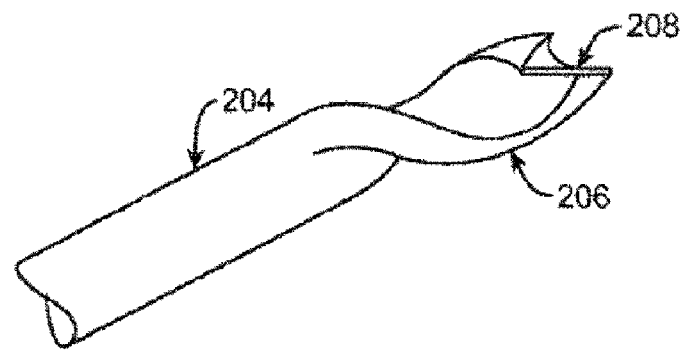
FIG. 34A is a perspective view of a drill-shaped distal end of a guidewire.
Figure 34B:
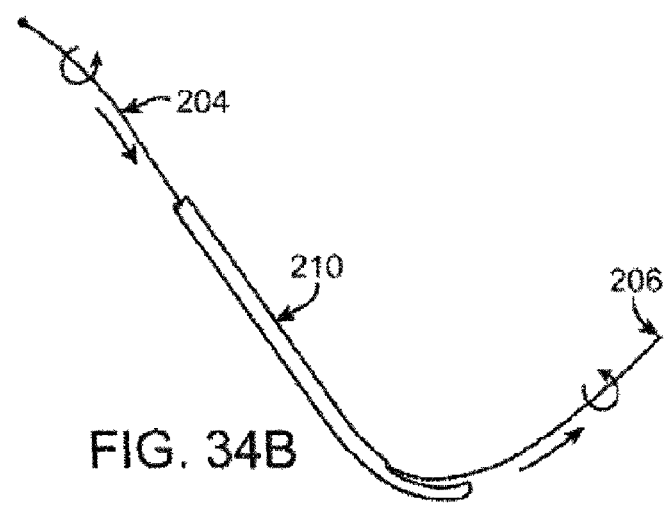
FIG. 34B is a side view of a guidewire as in FIG. 34A, being passed through a probe device.

Referring now to FIGS. 34A and 34B, another embodiment of a guidewire 204 may include a drill-shaped distal tip 206 with a cutting edge 208. Such a drill-shaped tip 206 may facilitate passage of guidewire 204 through tissue, as shown in FIG. 34B. Guidewire 204 may be advanced through a probe 210 and through tissue (not shown) by simultaneously pushing (solid-tipped, straight arrows) and twisting (hollow-tipped, curved arrows) guidewire 204 from its proximal end. Drill-shaped tip 206 may facilitate passage of guidewire 204 through tissue by acting as a drill.

Figure 38A:
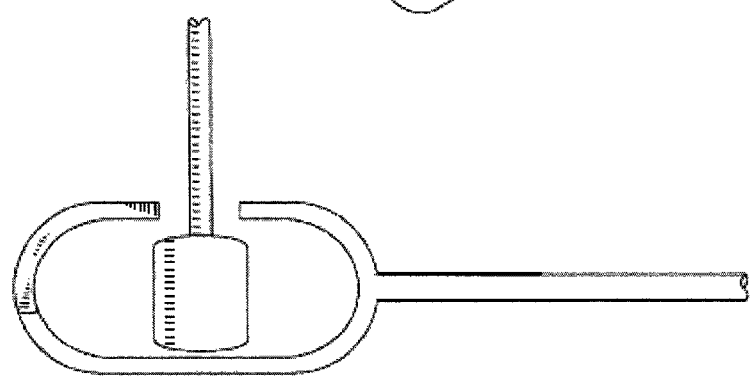
FIGS. 38A and 38B illustrate locking of the exchange system of FIG. 37.
Figure 38B:
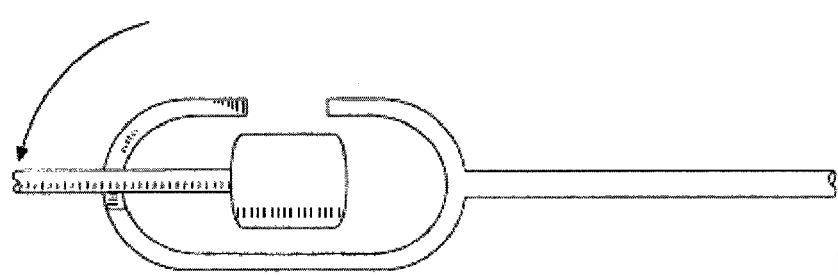
Figure 38C:
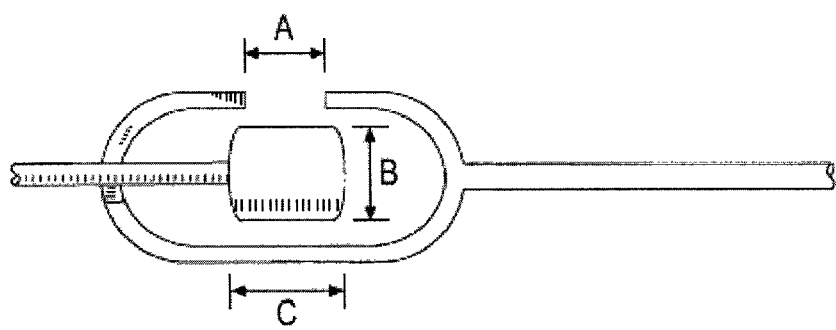
FIG. 38C is a cross-section through the system shown in FIG. 37, showing exemplary dimensions.

FIGS. 37 and 38A-38C illustrate another variation of an exchange system including a guidewire and a surgical device having a distal guidewire coupling exchange tip ("Rx" or exchange tip). In this variation the guidewire coupling member is configured to engage the proximal end of the guidewire, which is configured as a device coupling member having a cylindrical-shaped member. FIGS. 38A and 38B illustrate the coupling of the proximal end of the guidewire and the distal end of the device. In this variation, the two coupling regions are configured to lock when engaged, so that they may not be separated without the proper orientation and/or application of force. As illustrated in FIG. 38C, the opening in the guidewire coupling member has a diameter "A" that is greater than the diameter of the short axis ("B") of the distal end of the coupling member on the guidewire, but smaller than the longitudinal axis ("C") of the device coupling member on the guidewire. When the device coupling member of the guidewire is inserted in the opening in the guidewire coupling member of the device, and tension is applied (pulling the guidewire distal to the coupling member so that it extends in the slot of the guidewire coupling member), the guidewire and the device are locked together, and cannot be separated (even when tension is removed) without properly orienting the two so that the small diameter ("B") of the coupling member can exit the opening of the guidewire coupling member.

Figure 39A:
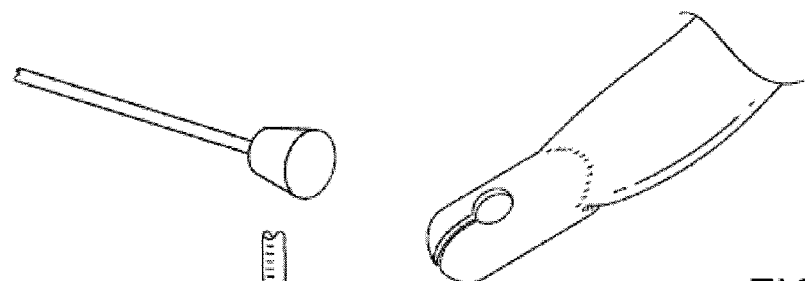
FIG. 39A is a perspective view of another variation of an exchange system.
Figure 39B:
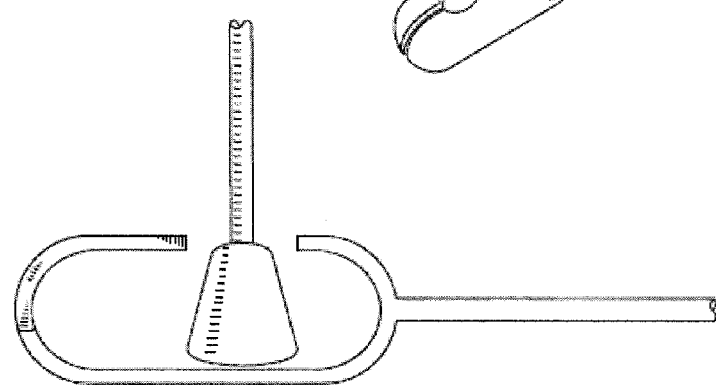
FIGS. 39B and 39C illustrate locking of the exchange system of FIG. 39A.
Figure 39C:
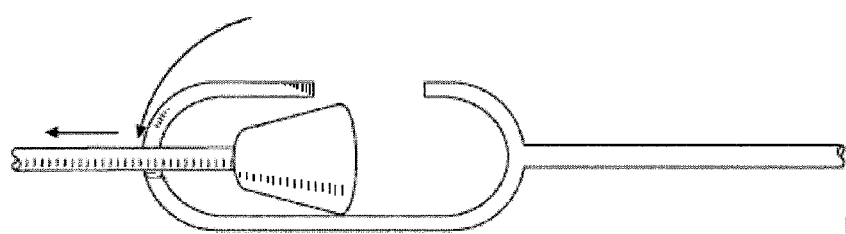
Figure 39D:
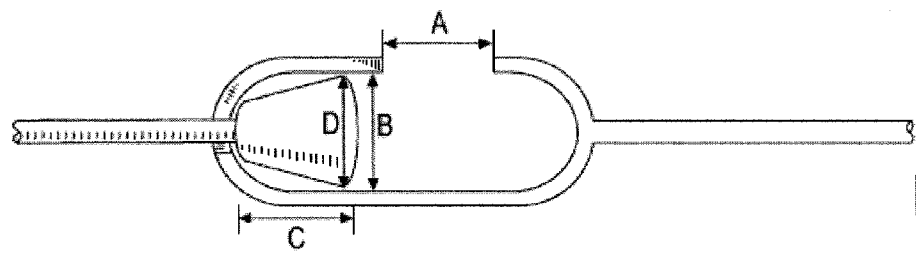
FIG. 39D is a cross-section through the system shown in FIG. 39A, showing exemplary dimensions.

FIGS. 39A-39D illustrate a very similar variation, in which the device coupling member on the proximal end of the guidewire may be permanently secured in the guidewire coupling member. In this example, the device coupling member of the guidewire has a conical, triangular or pyramidal shape in which the proximal end tapers distally so that as the proximal end of the guidewire is pulled into the guidewire coupling member of the surgical device, it become wedged and locked into the coupling member, as illustrated in FIG. 39D. Other variations of locking coupling members may be used, including releasably and permanently locking members.

Figure 40A:
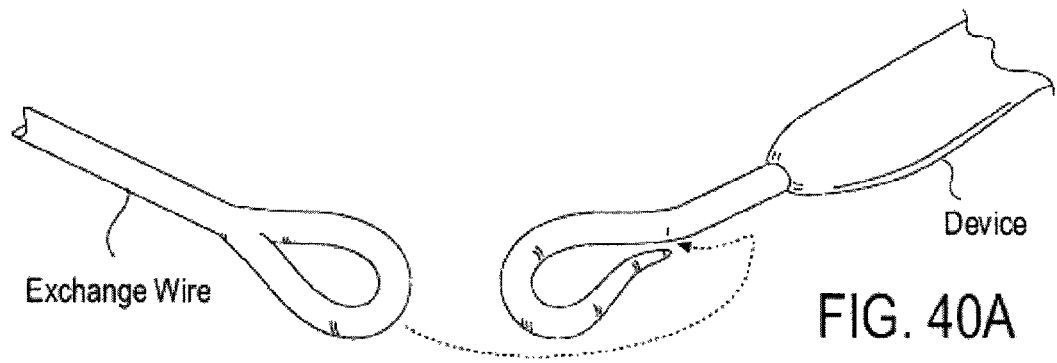
FIG. 40A is a perspective view of another variation of an exchange system.
Figure 40B:
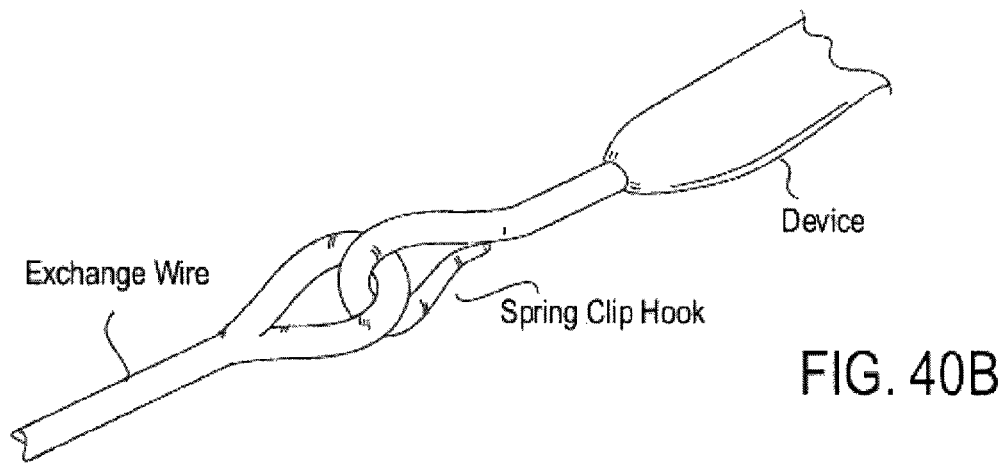
FIG. 40B illustrates locking of the exchange system of FIG. 40A.
Figure 40C:
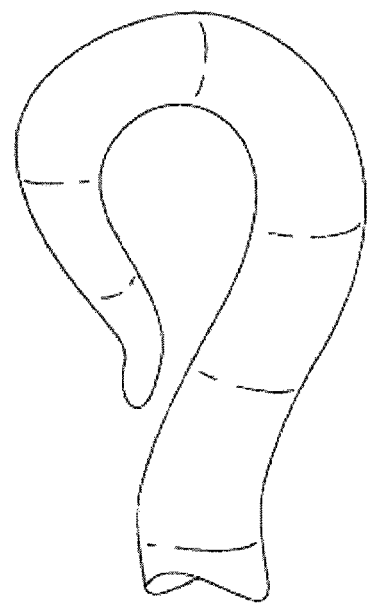
FIG. 40C shows a perspective view of one of the coupling members shown in FIG. 40A.

FIGS. 40A-40C illustrate another variation of a locking guidewire exchange system. In this variation the proximal end of the guidewire is configured as a loop or eyelet, and the distal end of the surgical device is configured as a hook having a progressively thicker cross-section. The very proximal end of the hook may be flanged away from the body slightly, allowing the loop or eyelet to more easily engage the hook. The thinner region at the proximal end may be more flexible, so that the look or eyelet can be pulled into the hook region by deflecting the thinner portion away from the longitudinal axis sufficiently to allow the loop to pass into the hook region. Thus, the hook may be referred to as a "spring clip" hook. The guidewire may be released from the device by applying appropriate force to pull the loop out of the spring clip hook.

Figure 41A:
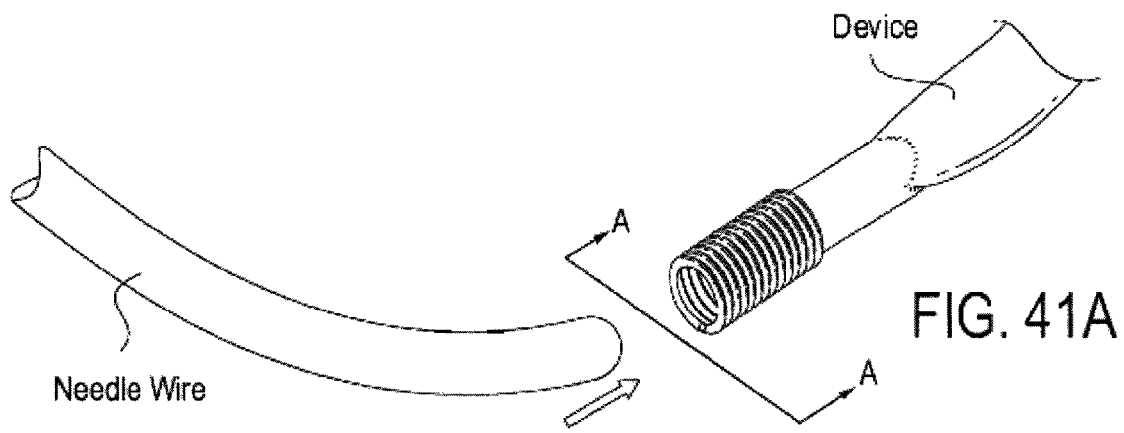
FIG. 41A is perspective view of a locking exchange system.
Figure 41B:
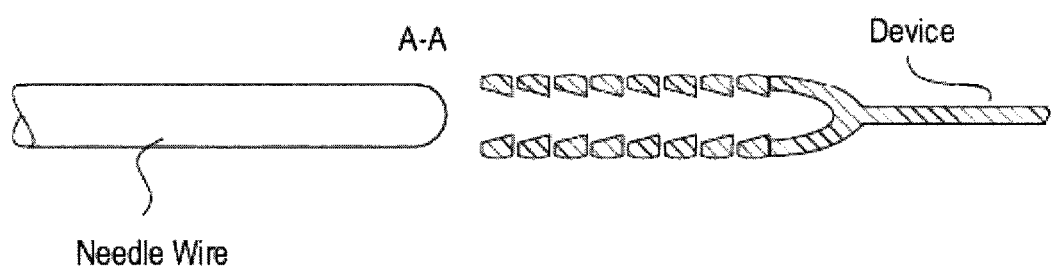
FIGS. 41B and 41C are cross-sectional views illustrating the operation of the exchange system shown in FIG. 41A.
Figure 41C:
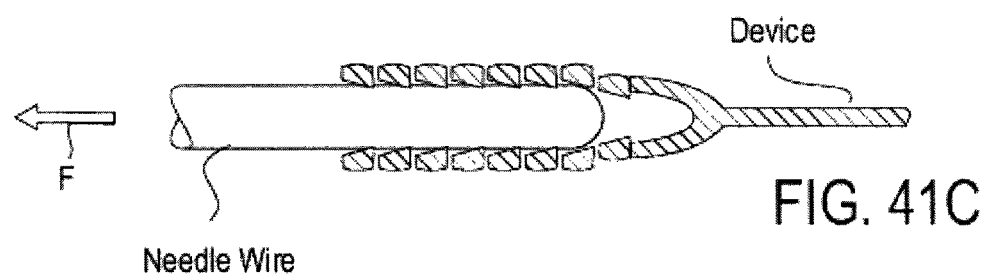

Another locking variation of a guidewire exchange system is shown in FIGS. 41A-41C. In this example, the guidewire coupling member on the device is configured as a coil or spring into which the guidewire may be inserted. The walls of the spring region may be tapered slightly to guide insertion. Pushing the guidewire into the coupling member may expand the spring slightly, whereas applying a tensioning force (e.g., by pulling on either or both the proximal end of the device and distal end of the guidewire) will tighten the connection between the guidewire and the device. In some variations the guidewire also include a coupling member which may be one or more regions (e.g., rings, ridges, bumps, etc.) that can fit between the loops or coils of the guidewire coupling member on the device.

FIGS. 42A-42C, 43A-43B, and 44A-44C illustrate other variations of locking or lockable guidewire exchange systems. In all of these exchange systems the guidewire may be secured to a first surgical device, and tension may be applied (e.g., to pull the device into position using the guidewire, and/or to urge the device against the target tissue). The devices may then be de-coupled from the guidewire (e.g., after the devices have been removed from the subject while leaving the guidewire in place), and another device may be coupled to the guidewire and positioned by pulling the guidewire and/or used to urge the device against the target tissue.

Figure 42A:
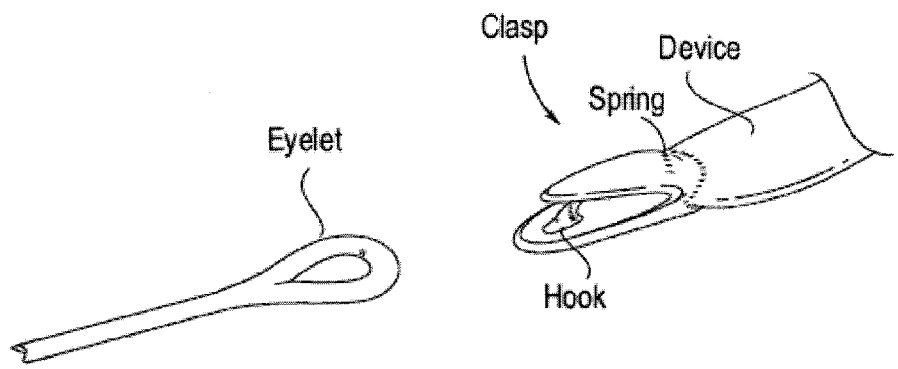
FIGS. 42A-42C illustrate another locking exchange system.
Figure 42B:
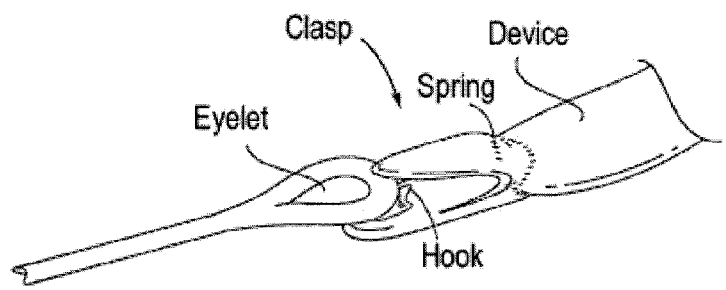
Figure 42C:
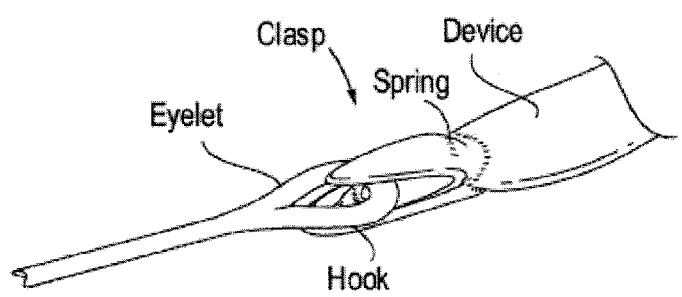
Figure 43A:
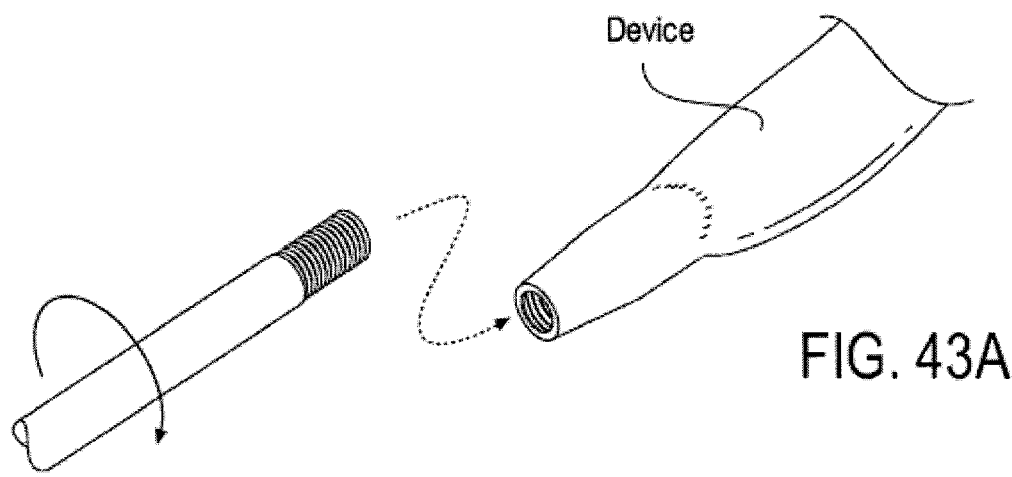
FIGS. 43A-43B illustrate an exchange system including a threaded coupling region.
Figure 43B:
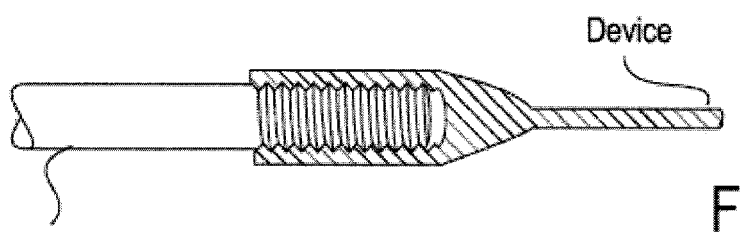
Figure 44A:
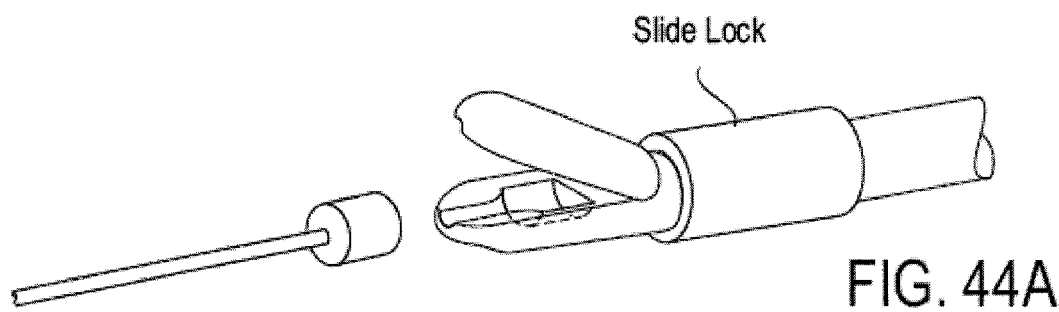
FIGS. 44A-44C illustrate operation of a locking exchange system.
Figure 44B:
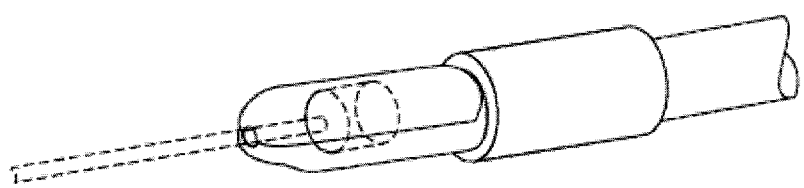
Figure 44C:
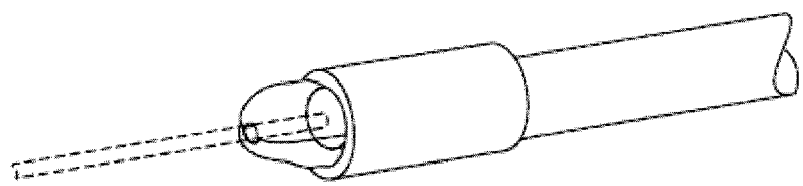

For example, FIG. 42A-42C illustrate a guidewire having a loop or eyelet at the proximal end coupling with a guidewire coupling region of a surgical device that is configured as a clasp. The clasp includes jaws that may move to close over the eyelet, securing it on a hook or post in the guidewire coupling region. In the example shown in FIGS. 43A and 43B, the proximal end of the guidewire is threaded and may be screwed into the guidewire coupling member of a surgical device, shown in cross section in FIG. 43B. Finally, in FIGS. 44A-44C the guidewire coupling member of a surgical device includes a sliding lock may be used to secure a hinged jaw closed over the proximal end of a guidewire. The lock may be slid proximally to unlock the hinged jaw and release the guidewire.

Figure 45A:
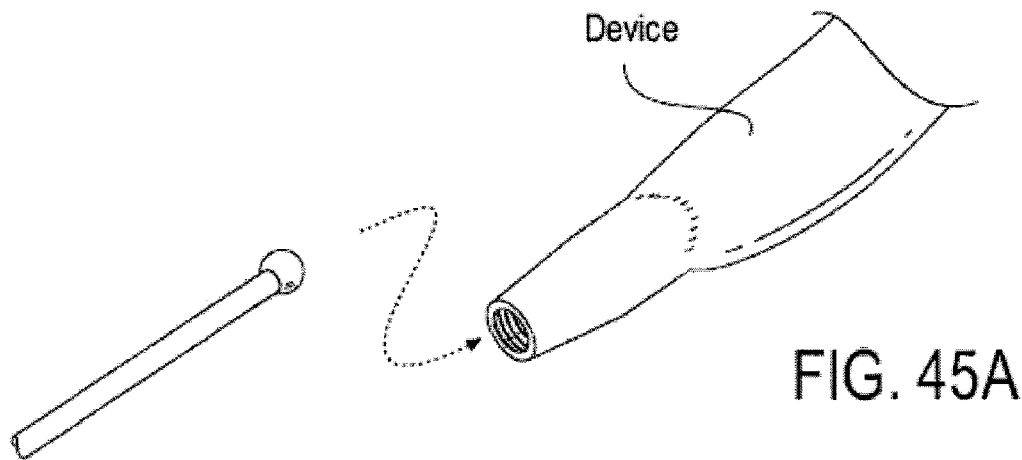
FIG. 45A is a perspective view of an exchange system.
Figure 45B:
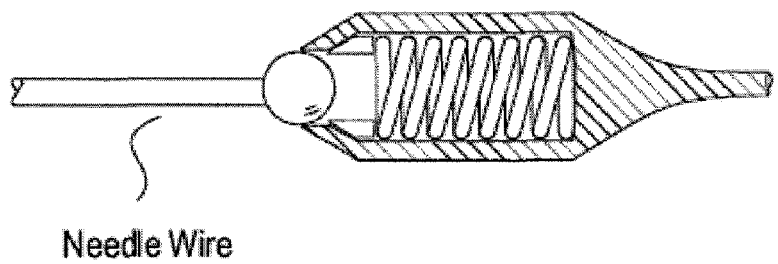
FIG. 45B is a cross-section of the exchange system shown in FIG. 45A.
Figure 45C:
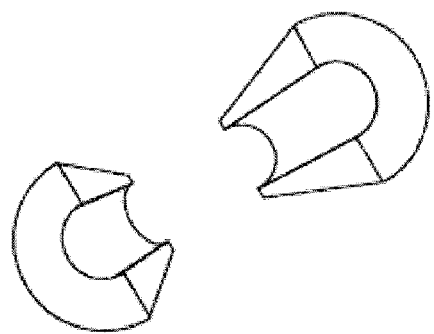
FIG. 45C shows one variation of a locking portion in a coupling member of the exchange system shown in FIG. 45A.

FIGS. 45A and 45B illustrate another variation of a spring-locking guidewire coupling region on a surgical device that mates with the device coupling region on a guidewire. In this example, a spring in the guidewire coupling member pushes one or more wedge locks distally. The spring and wedge locks can be displaced by pushing the proximal end of the guidewire into the coupling member proximally, but pulling distally only provides additional force to lock the guidewire in the coupling member. A lock release mechanism (e.g., pulling the spring or wedge locks proximally) may be included to allow release of the guidewire.

Figure 35A:
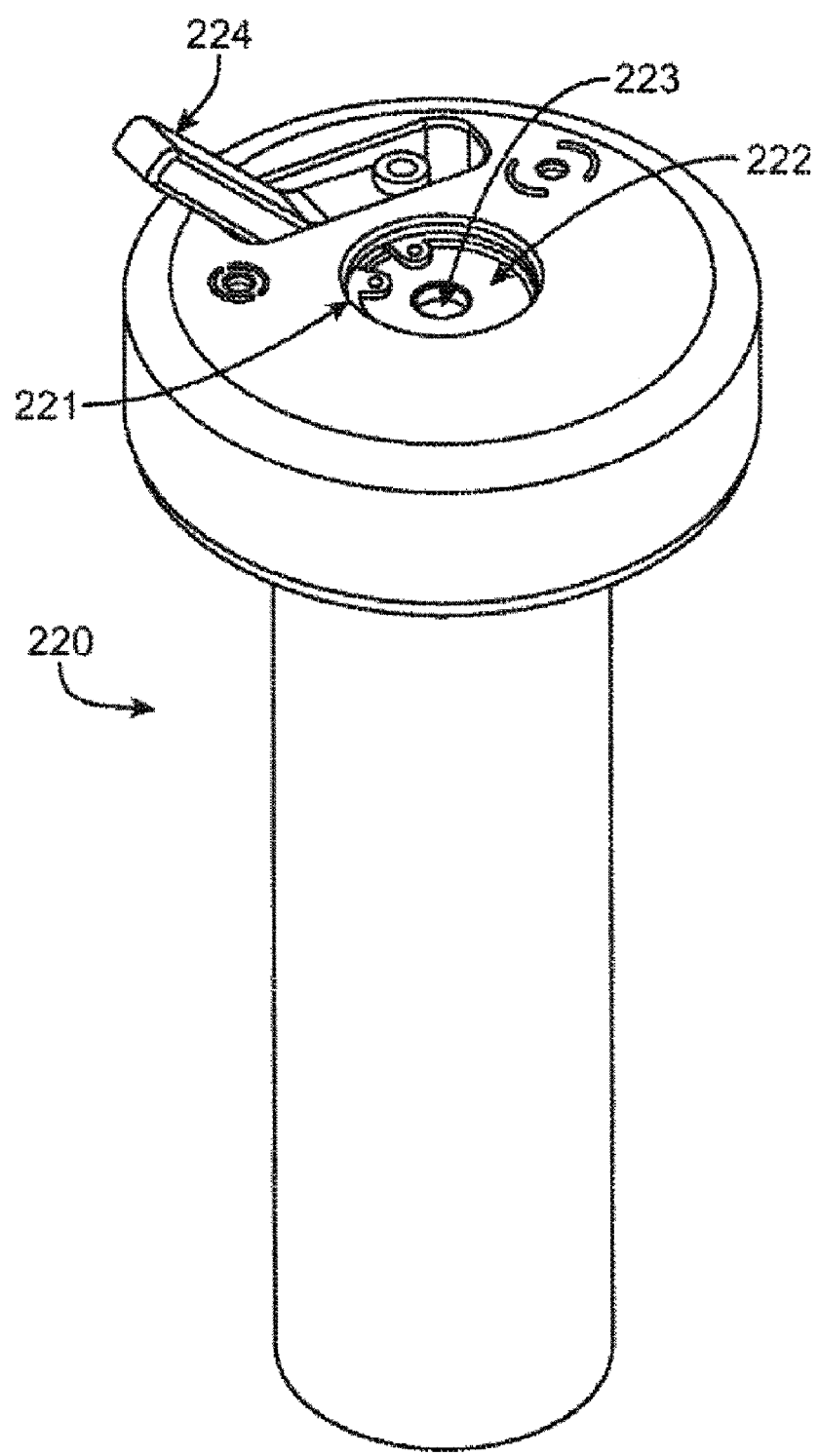
FIGS. 35A and 35B are perspective and exploded views of a handle for grasping a guidewire.

With reference to FIG. 35A, in some embodiments, a guidewire system may include a guidewire handle 220 for grasping a guidewire outside the patient. Such a guidewire handle 220 may include, for example, a guidewire clamping mechanism 222 housed in a central, longitudinal bore 221 of handle 220 and including a central guidewire aperture 223. Handle 220 may also include a lock lever 224 for tightening clamping mechanism 222 around a guidewire. At some points in the present application, handles similar to handle 220 are referred to as "distal handles," and handles coupled with various tissue modification devices are referred to as "proximal handles." These terms, "distal" and "proximal," are generally used to distinguish the two types of handles and to denote that one is more proximal than the other, during use, to a first incision or entry point into a patient, through which a guidewire system is placed and then used to pull a tissue modification device into position in the patient. "Distal" and "proximal," however, are used merely for clarification and do not refer to the relation of any device to specific anatomical structures, the position of a physician/user of the described devices/systems, or the like. Thus, in various embodiments, either type of handle may be "distal" or "proximal" relative to various structures, users or the like. For the purposes of FIGS. 35A and 35B, the embodiment is described as guidewire handle 220, denoting its function of holding a guidewire.

Figure 35B:
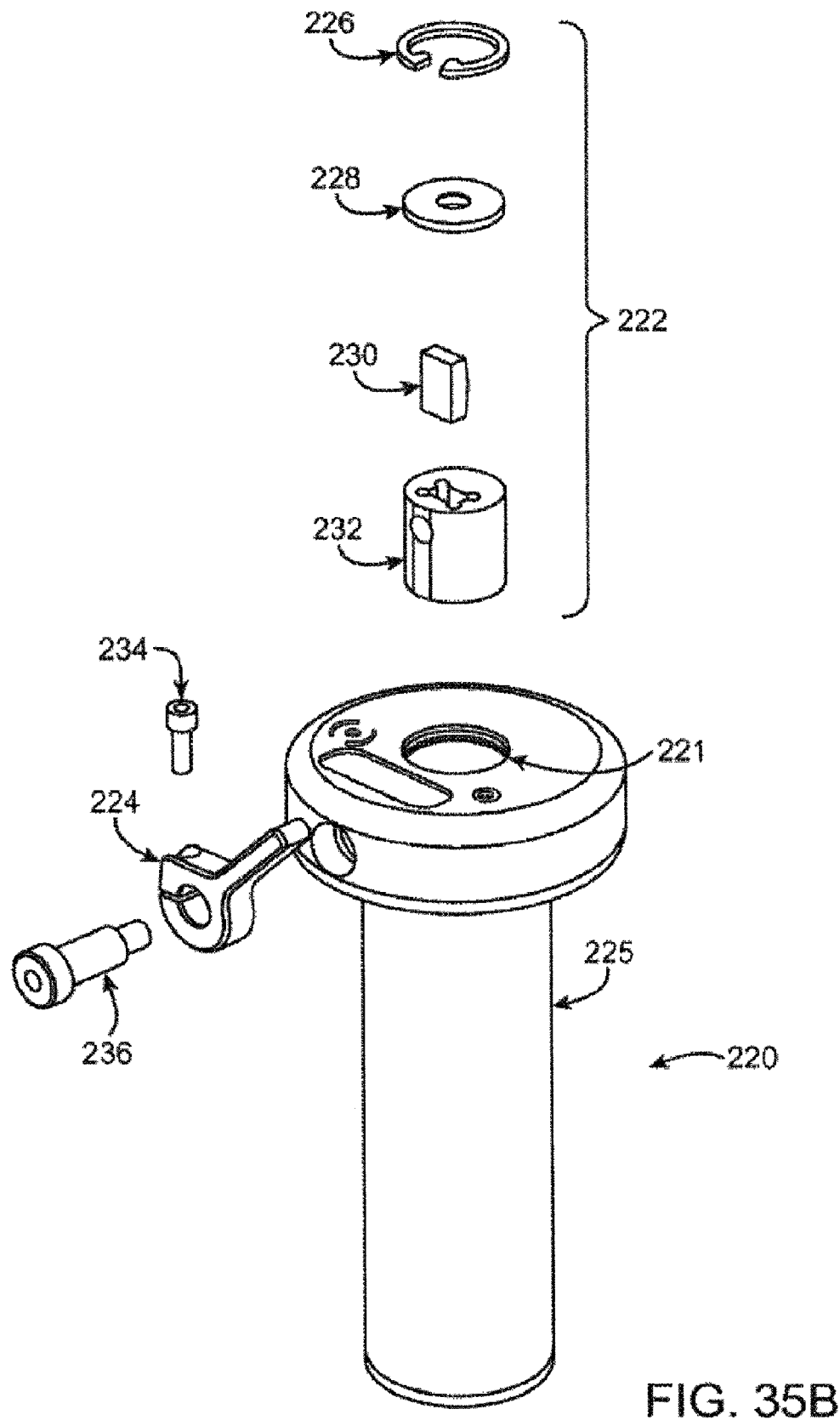

FIG. 35B provides an exploded view guidewire handle 220. A handle body 225 may be made of any suitable material and have any desired shape and size. In various alternative embodiments, for example, handle body 220 may be made from any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phyno (Imphy SA, Paris, France). Suitable polymers include but are not limited to nylon, polyester, Dacron™, polyethylene, acetal, Delrin™ (DuPont, Wilmington, Del.), polycarbonate, nylon, polyetheretherketone (PEEK), and polyetherketoneketone (PEKK). Ceramics may include but are not limited to aluminas, zirconias, and carbides.

Clamping mechanism 222 may include, for example, a snap ring 226, a keeper washer 228, a flat anvil 230, and a cage barrel 232, all of which fit within central bore 221 of handle body 225. Lock lever 224 may be coupled with a pinch screw 234 and a shoulder screw 236. When lock lever 224 is turned in one direction, it pushes shoulder screw 236 against clamping mechanism 222 to cause mechanism 222 to clamp down on a guidewire. Lock lever 224 may be turned in an opposite direction to loosen clamping mechanism 222, thus allowing a guidewire to be introduced into or release from central guidewire aperture 223.

Figure 36A:
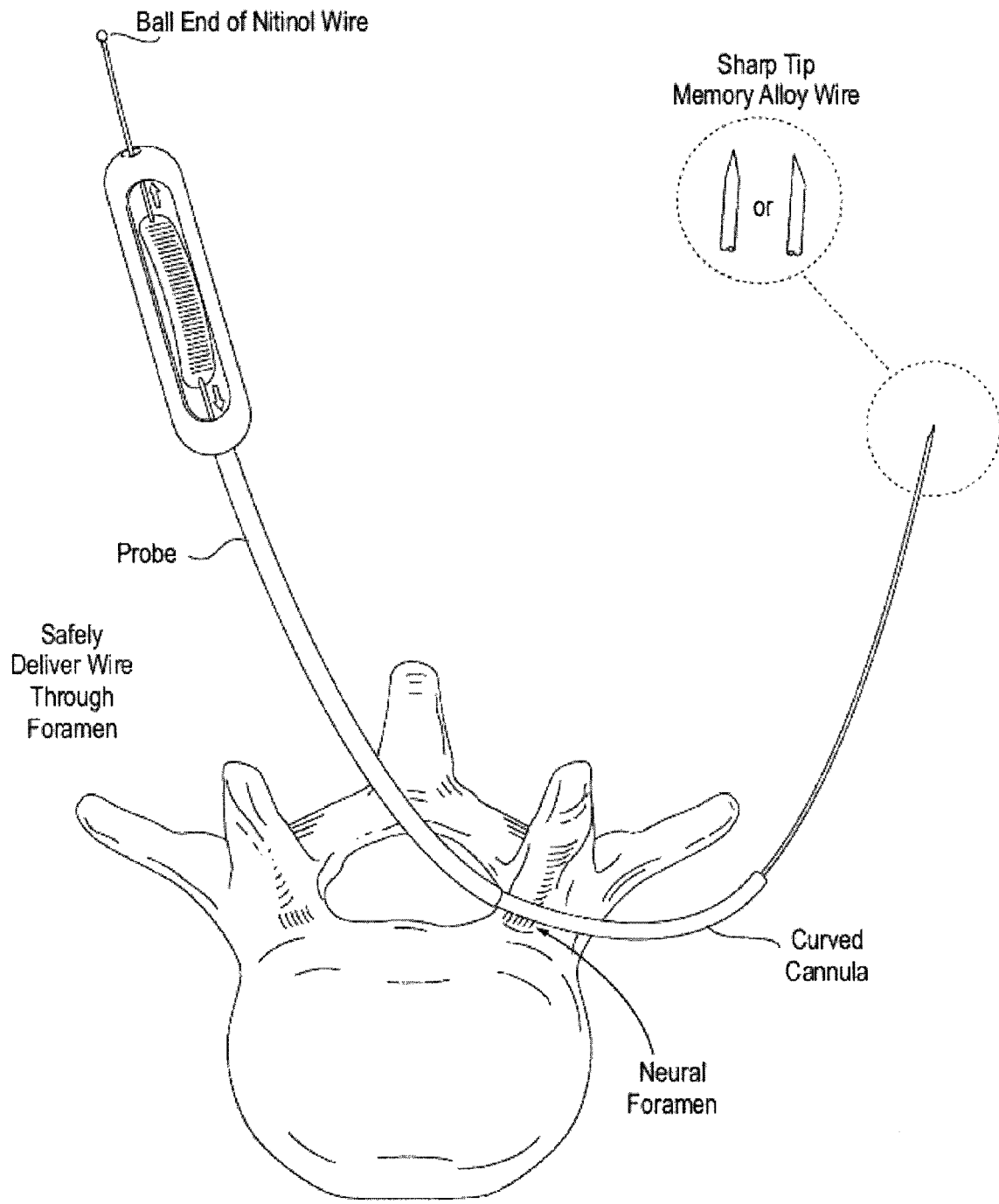
FIGS. 36A to 36C illustrate one method of exchanging a device using a positioned guidewire.
Figure 36B:
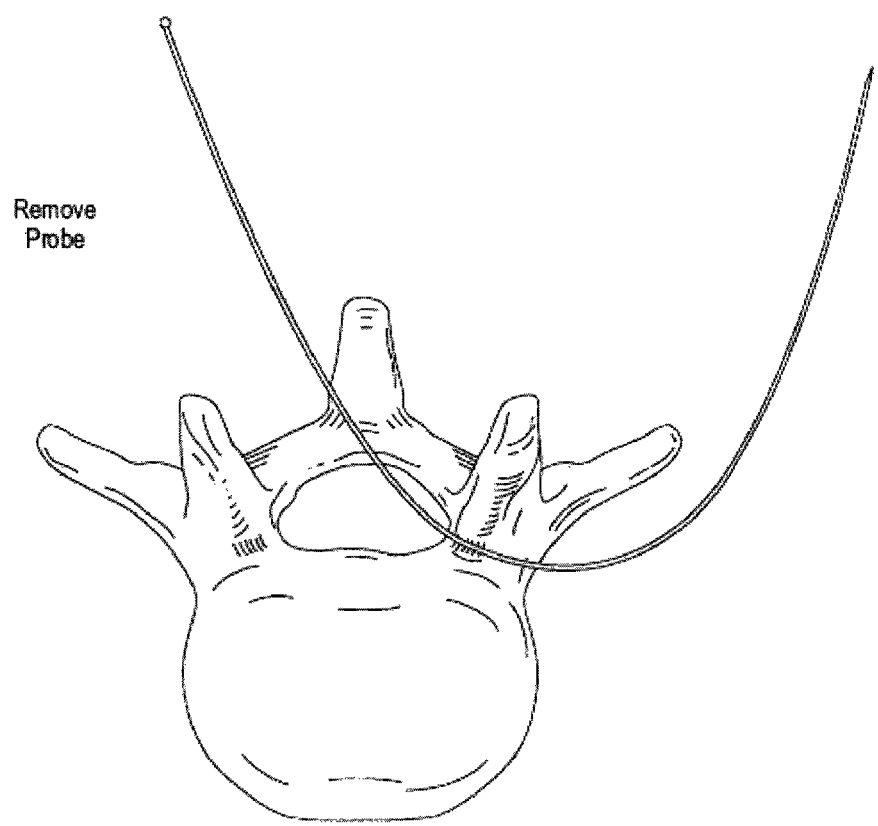
Figure 36C:
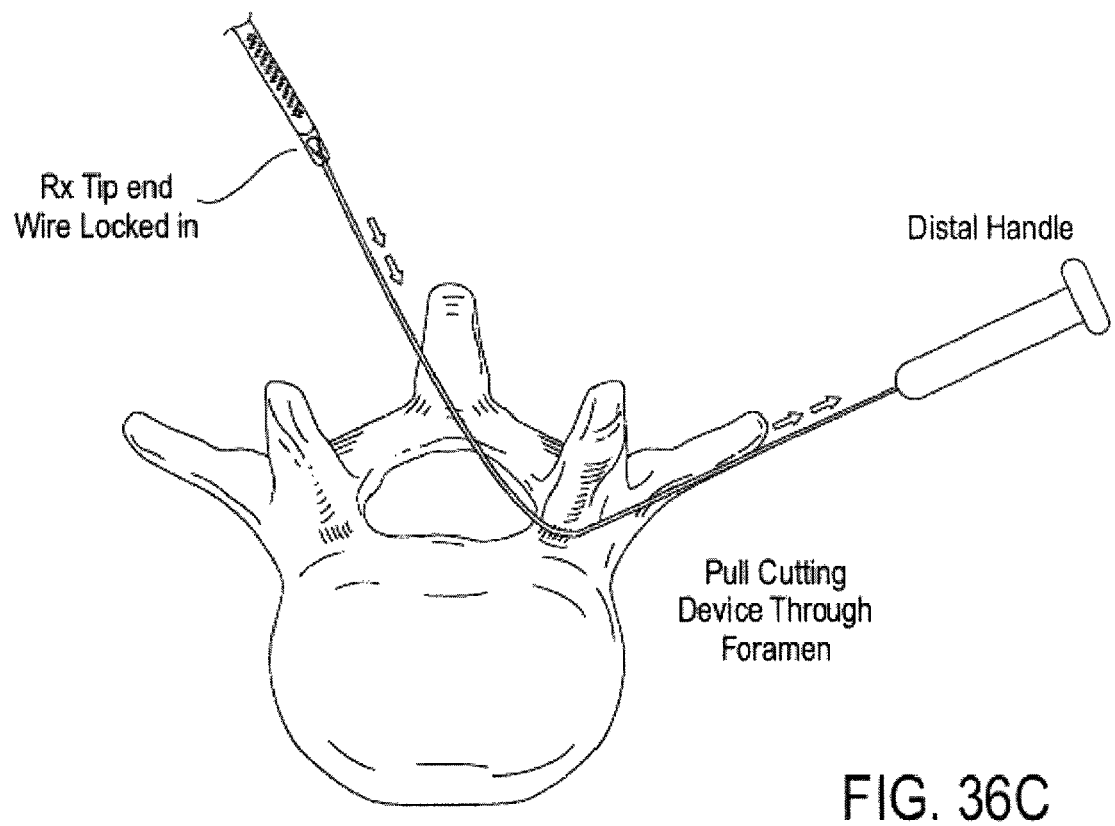
Figure 37:
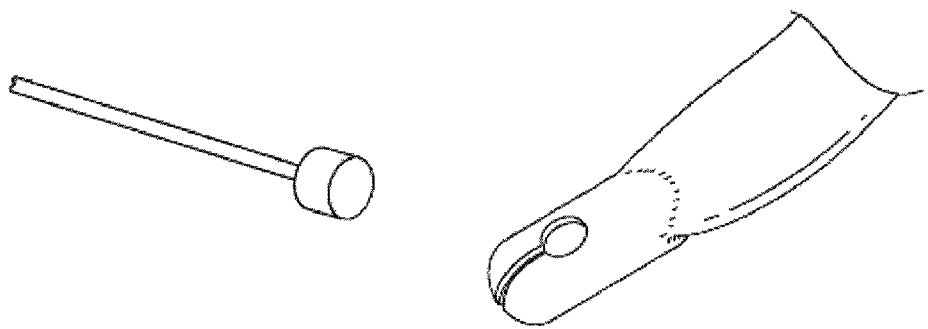
FIG. 37 shows a perspective view of one variation of an exchange system.

FIGS. 36A-36B illustrate one method of using an exchange system as described. For example, FIG. 36A shows a spinal region including a neural foramen into which a cannulated probe (curve cannula) has been inserted. In general, the guidewire is inserted into the tissue (e.g., through a neural foramen) so that the pathway through the tissue includes at least one (or only one) bend or curve in which the target tissue is positioned within the radius of the curve. The guidewire may be positioned by one or more access devices. For example, FIG. 36A shows positioning of a guidewire using an access cannula having an integrated curved inner cannula slidably disposed within the outer cannula. The inner curved member is extended from the distal end of the access cannula into the foramen and around the target tissue, as shown. A guidewire may then be inserted through it, so that a distal end of the guidewire (which may be sharp) extends from the patient. Either or both the cannula and the curved inner member may also include a neural localization electrode or electrodes so that the guidewire can be positioned away from the nerve. The access cannula can then be retracted and removed from the patient, leaving the guidewire behind. As illustrated in FIGS. 36B and 36C, the guidewire may then be used (as described in detail above) to pull a surgical device (e.g., a cutting device, etc.) through the body so that it is positioned relative to the target tissue. For example, the proximal end of the cannula, initially protruding from the patient, may be coupled to a surgical device, as described above. As shown in FIG. 36C, the distal end of the guidewire can then be pulled to draw the surgical device through the patient until it is positioned as desired relative to the target tissue. In some variations the positioning may be confirmed. Positioning may be confirmed by one or more of a direct visualization technique, feel (e.g., tactile feedback on the guidewire and/or surgical device), sensors on the surgical device or guidewire, depth markers on the guidewire or surgical device, or the like.

Once in position, tension may be applied to the surgical device. For example, in some variations the guidewire remains at least partially in the patient and attached to the surgical device. Tension may be applied by pulling distally on the guidewire and proximally on the surgical device, to urge the surgical device against the target tissue. The surgical device may then be moved (e.g., back and forth across the target tissue) to mechanically actuate the surgical device, or it may be otherwise actuated, as described previously. After treatment of the tissue with this first surgical device, the device may be withdrawn from the patient. For example, the device may be withdrawn by pulling it proximally out of the patient, until the proximal end of the guidewire is again outside of the patient.

The surgical device can then be exchanged on the guidewire. For example, the proximal end of the guidewire may then be de-coupled from the surgical device, and another surgical device may be coupled, as previously described. The surgical device can again be positioned adjacent to the target tissue, and the device can be urged against the target tissue. This procedure may be repeated as often as necessary until the target tissue has been treated to the desired level. As mentioned above, any appropriate surgical device may be used an applied in this way, including (but not limited to) decompression devices, measuring devices (balloons, sounds, etc.), catheters or other devices for suction and irrigation, and devices for delivering active agents (i.e., hemostatic agents such as Thrombin, steroids, or other drugs), bone wax, etc. Implants may also be positioned by pulling then through the subject using the guidewire.

Once the procedure is complete, the guidewire may be removed from the subject.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What is claimed is:

1. A method of treating a patient, the method comprising:
advancing a distal end of a guidewire into the patient's body from a first site, advancing adjacent to a target tissue, and out of the body from a second site, while maintaining a proximal end of the guidewire outside the body at the first site;
coupling an end of the guidewire on or near a distal end of a surgical device outside of the body by inserting the end of the guidewire at an angle relative to the distal end of the surgical device into a channel at or near the distal end of the surgical device and rotating one or both of the end of the guidewire and the distal end of the surgical device to lock the guidewire and the surgical device together;
pulling the guidewire to guide the surgical device adjacent to the target tissue; and
withdrawing the surgical device and end of the guidewire from the patient while maintaining the guidewire within the body and de-coupling the end of the guidewire from the surgical device and coupling the end of the guidewire on or near a distal end of a second surgical device outside of the body by inserting the end of the guidewire at an angle relative to the distal end of the second surgical device into a channel at or near the distal end of the second surgical device and rotating one or both of the end of the guidewire and the distal end of the second surgical device to lock the guidewire and the second surgical device together,
wherein at least one of the surgical device and the second surgical device comprises an abrasive surface.

2. The method of claim 1, wherein the step of coupling the end of the guidewire on or near the distal end of the surgical device comprises coupling the end of the guidewire to the first or second surgical device with at least one coupling member.

3. The method of claim 1, wherein the step of coupling the end of the guidewire on or near the distal end of the surgical device comprises engaging a guidewire coupling member on the surgical device with the end of the guidewire.

4. The method of claim 1, wherein de-coupling the end of the guidewire from the surgical device further comprises rotating the end of the guidewire, the distal end of the surgical device, or both, to release a shaped member from the channel.

5. The method of claim 1, further comprising urging the surgical device against the target tissue by applying tension to either or both of the surgical device extending from the first site and the guidewire extending from the second site.

6. The method of claim 1, further comprising performing a surgical procedure on the target tissue using the surgical device.

7. The method of claim 6, wherein the step of performing a surgical procedure comprises reciprocating the surgical device by pulling on either or both of the surgical device extending from the first site and the guidewire extending from the second site.

8. A method for guiding at least a portion of a surgical device to a desired position between two tissues in a patient's body, the method comprising:
advancing a distal end of a guidewire into the patient's body, between two tissues, and out of the body, while maintaining a proximal end of the guidewire outside the body;
coupling the proximal end of the guidewire with at least one coupling member on or near a distal end of a surgical device outside of the body by inserting the proximal end of the guidewire at an angle relative to the distal end of the surgical device into a channel at or near the distal end of the surgical device and rotating one or both the proximal end of the guidewire and the distal end of the surgical device to lock the guidewire and the surgical device together;
pulling the distal end of the guidewire to guide at least a portion of the surgical device to a desired position adjacent to the target tissue;
withdrawing the surgical device and distal end of the guidewire proximally from the patient while maintaining the guidewire within the body and de-coupling the proximal end of the guidewire from the surgical device and coupling the proximal end of the guidewire with at least one coupling member on or near a distal end of a second surgical device outside of the body by inserting the proximal end of the guidewire at an angle relative to the distal end of the second surgical device into a channel of the coupling member and rotating one or both the proximal end of the guidewire and the distal end of the second surgical device to lock the guidewire and the second surgical device together;

pulling the distal end of the guidewire to guide at least a portion of an abrasive surface of the second surgical device to a desired position adjacent to the target tissue.

9. The method of claim 8, further comprising coupling the proximal end of the guidewire on or near the distal end of the first surgical device by coupling the proximal end of the guidewire to the first surgical device with at least one coupling member.

10. The method of claim 8, further comprising coupling the proximal end of the guidewire on or near the distal end of the first surgical device by engaging a guidewire coupling member on the first surgical device with the proximal end of the guidewire.

11. The method of claim 8, wherein de-coupling the end of the guidewire from the surgical device further comprises rotating the end of the guidewire, the distal end of the surgical device, or both, to release a shaped member from the channel.

12. A method for performing a procedure on a target tissue in a patient's body, the method comprising:

coupling a proximal end of a guidewire with at least one coupling member on or near a distal end of a surgical device outside of the body by inserting the proximal end of the guidewire at an angle relative to the distal end of the surgical device into a channel at or near the distal end of the surgical device;

pulling a distal end of the guidewire to guide at least a portion of the surgical device to a desired position between two tissues, such that an abrasive portion of the surgical device faces the target tissue and an atraumatic portion of the surgical device faces non-target tissue;

performing a procedure on the target tissue by reciprocating the surgical device by applying tension to both a portion of the guidewire outside of the body and a proximal portion of the surgical device; and withdrawing the surgical device and proximal end of the guidewire from the patient while maintaining the guidewire within the body and de-coupling the proximal end of the guidewire from the surgical device, and coupling the proximal end of the guidewire on or near a distal end of a second surgical device outside of the body by inserting the proximal end of the guidewire at an angle relative to the distal end of the second surgical device into a channel at or near the distal end of the second surgical device.

* * * * *